US008057998B1

(12) United States Patent
Ryan

(10) Patent No.: US 8,057,998 B1
(45) Date of Patent: Nov. 15, 2011

(54) ISOLATED GENOMIC POLYNUCLEOTIDE FRAGMENTS FROM CHROMOSOME 19 THAT ENCODE HUMAN SYNTAXIN

(75) Inventor: James W Ryan, Augusta, GA (US)

(73) Assignee: Ryogen LLC, Suffern, NY (US)

( * ) Notice: Subject to any disclaimer, the term of this patent is extended or adjusted under 35 U.S.C. 154(b) by 258 days.

(21) Appl. No.: 12/276,550

(22) Filed: Nov. 24, 2008

Related U.S. Application Data

(63) Continuation of application No. 11/483,373, filed on Jul. 7, 2006, now Pat. No. 7,470,522.

(60) Provisional application No. 60/697,815, filed on Jul. 9, 2005.

(51) Int. Cl.
*C12Q 1/68* (2006.01)
*C12N 15/00* (2006.01)
*C12P 21/06* (2006.01)
*C07H 21/02* (2006.01)

(52) U.S. Cl. ........ 435/6; 435/69.1; 435/320.1; 536/23.1

(58) Field of Classification Search .................. 536/23.1; 435/320.1, 6, 69.1
See application file for complete search history.

(56) References Cited

OTHER PUBLICATIONS

Notice of Allowance Aug. 5, 2008 (U.S. Appl. No. 11/483,373).
Non-Final Rejection Jan. 16, 2008 (U.S. Appl. No. 11/483,373).
Altschul et al. "Gapped BLAST and PSI-BLAST: a new generation of protein database search programs." Nucl. Acids. Res. 25: 3389-3402. 1997.
Burge et al. "Prediction of complete genome structures in human genomic DNA." J. Mol. Biol. 268: 78-94. 1997.
Chumakov et al. "C/EBP regulation of XCP/FIZZ/resistin genes." RH PubMed Accession No. AF352730, sumbitted Feb. 23, 2001, bases 1-4922.
Darnell et al. Molecular Cell Biology W. H. Freeman and Company, New York. p. 373. 1986.
DOE Joint Genome Institute and Stanfod Human Genome Center. "*Homo sapiens* chromosome 19 clone CTD-3214H19" PubMed Accession No. AC008763, submitted Aug. 3, 1999. bases 1 to 177062.
Holcomb et al. "*Homo sapiens* cysteine-rich secreted protein (FIZZ3) mRNA, complete cds." PubMed Accession No. AF205952, submitted Aug. 28, 2000, bases 1 to 457.
"*Homo sapiens* syntaxin binding proten 2 (STXBP2) mRNA" PubMed Accession No. NM_006949 (multiple submissions- earliest submission 1995), bases 1 to 1815.
Katagiri et al. "A novel isoform of syntaxin-binding protein homologous to yeast Sec1 expressed ubiquitously in mammalian cells" J. Biol. Chem. 270: 4963-4966. 1995.
McTernan et al. "Increased resistin gene and protein expression in human abdominal adipose tissue." J. Clinical Endocrinology & Metabolism 87: 2407-2410. 2002.
Steppan et al. "The hormone resistin links obesity to diabetes" Nature 409: 307-312. 2001.
Waterston et al. "*Homo sapiens* chromosome 19 clone RP11-492L14" PubMed Accession No. AC021153, submitted Jan. 14, 2000, bases 1 to 155645.
Ziegler et al. "Molecular Characterization of a nonneuronal human UNC16 homolog" Genomics 37: 19-23. 1996.
U.S. Appl. No. 12/276,467 Non-Final Office Action, Dec. 21, 2010.

*Primary Examiner* — Karen Carlson
(74) *Attorney, Agent, or Firm* — Cheryl H. Agris

(57) ABSTRACT

The invention is directed to isolated genomic polynucleotide fragments that encode human resistin and human syntaxin binding protein 2, vectors and hosts containing these fragments and fragments hybridizing to noncoding regions as well as antisense oligonucleotides to these fragments. The invention is further directed to methods of using these fragments to obtain human resistin and human syntaxin binding protein 2 and to diagnose, treat, prevent and/or ameliorate a pathological disorder.

19 Claims, No Drawings

US 8,057,998 B1

ISOLATED GENOMIC POLYNUCLEOTIDE FRAGMENTS FROM CHROMOSOME 19 THAT ENCODE HUMAN SYNTAXIN

PRIORITY CLAIM

This application claims priority to application Ser. No. 60/697,815, filed Jul. 9, 2005 under 35 USC 119(e), the contents of which are herein incorporated by reference. This application is a divisional application Ser. No. 11/483,373, filed Jul. 7, 2006, the contents of which are also herein incorporated by reference.

FIELD OF THE INVENTION

The invention is directed to isolated genomic polynucleotide fragments that encode human resistin and human syntaxin binding protein 2, vectors and hosts containing these fragments and fragments hybridizing to noncoding regions as well as antisense oligonucleotides to these fragments. The invention is further directed to methods of using these fragments to obtain human resistin and human syntaxin binding protein and to diagnose, treat, prevent and/or ameliorate a pathological disorder.

BACKGROUND OF THE INVENTION

Chromosome 19p13.3-p13.2 contains genes encoding, for example, zinc-finger protein 14, oncogene VAV1, tartrate-resistant acid phosphatase, bone marrow stromal cell antigen, calponin 1 and syntaxin binding protein 2; the last of which is discussed in detail below. The gene that encodes resistin, is known to be disposed on chromosome 19.

Human Resistin

Human resistin is a protein that interferes with the actions of insulin on liver and muscle. It is disposed largely in white adipose tissue and in crypt epithelium of the intestine. Given its disposition in fatty tissue and its inhibition of insulin effects, resistin is believed to link obesity to type 2 diabetes (Steppan et al., Nature 409: 307-312, 2001). Consistent with this view, antibodies to resistin improve blood sugar levels and insulin actions in mice with diet-induced obesity. Conversely, administration of recombinant resistin impairs glucose tolerance and insulin actions. The resistin cDNA is identical to the cDNAs for entities called FIZZ3, accession number AF205952, and C/EBP-epsilon regulated myeloid-specific secreted cysteine-rich protein precursor, accession number AF352730. The latter sequence contains the intron sequences and some 5'- and 3'-sequences.

Human Syntaxin Binding Protein 2

Human syntaxin binding protein, a member of the STXBP/unc-18/Sec1 protein family, is disposed largely in placenta, lung, liver, kidney, peripheral lymphocytes and pancreas. It is believed to play a role in vesicular transport between the golgi apparatus and the cell membrane in non-neuronal tissues. Mouse syntaxin binding protein 2=binds to syntaxins 1A, 2 and 3 but not to syntaxin 4 (Katagiri et al., J. Biol. Chem. 270: 4963-6, 1995). The human gene is upregulated in interleukin-2 activated natural killer cells (Ziegler et al., Genomics 37: 19-23, 1996). The cDNA has been determined (see accession number NM_006949).

OBJECTS OF THE INVENTION

Although cDNAs encoding the above-disclosed proteins have been isolated, their locations on chromosome 19 have not been determined. Furthermore, genomic nucleic acids encoding these polypeptides have not been isolated. Noncoding sequences play a significant role in regulating the expression of polypeptides as well as the processing of RNA encoding these polypeptides.

There is clearly a need for obtaining genomic polynucleotide sequences encoding these polypeptides. Therefore, it is an object of the invention to isolate such genomic polynucleotide sequences.

SUMMARY OF THE INVENTION

The invention is directed to isolated genomic nucleic acid molecules or polynucleotides, said polynucleotides obtainable from human chromosome 19 comprising a naturally occurring polynucleotide sequence at least 95% identical to a sequence selected from the group consisting of:

(a) a forward or reverse strand of a nucleic acid molecule encoding a polypeptide selected from the group consisting of human resistin depicted in SEQ ID NO:1 and/or human syntaxin binding protein 2 depicted in SEQ ID NO:2 or variant of SEQ ID NO:1 or SEQ ID NO:2;

(b) a forward or reverse strand of a nucleic acid molecule containing SEQ ID NO:3 which encodes human resistin depicted in SEQ ID NO:1 and/or SEQ ID NO:4 which encodes human syntaxin binding protein 2 depicted in SEQ ID NO:2 or variant of SEQ ID NO:3 and/or SEQ ID NO:4;

(c) a forward or reverse strand of a nucleic acid molecule at least 20 nucleotides in length unique to a noncoding region(s) of SEQ ID NO: 3 or 4, preferably about 20-35,000 in length;

(d) a forward or reverse strand of a nucleic acid molecule at least 60 nucleotides in length unique to a contiguous coding and noncoding nucleic acid sequence(s) of SEQ ID NO:3 or 4, preferably about 60-35,000 nucleotides in length;

(e) a nucleic acid molecule or its reverse strand that extends from the 5'-end of SEQ ID NO:3 through the 3'-end of SEQ ID NO:4 as depicted in SEQ ID NO:5;

(f) a nucleic acid molecule which hybridizes to any one of the nucleic acid molecules specified in (a)-(b) and as well as nucleic acid constructs, expression vectors and host cells containing these polynucleotide sequences.

The polynucleotides of the present invention may be used for the manufacture of a gene therapy for the prevention, treatment or amelioration of a medical condition by adding an amount of a composition comprising said polynucleotide effective to prevent, treat or ameliorate said medical condition.

The invention is further directed to obtaining these polypeptides by:

(a) culturing host cells comprising these sequences under conditions that provide for the expression of said polypeptide and (b) recovering said expressed polypeptide.

The polypeptides obtained may be used to produce antibodies by (a) optionally conjugating said polypeptide to a carrier protein;

(b) immunizing a host animal with said polypeptide or peptide-carrier protein conjugate of step (b) with an adjuvant and (c) obtaining antibody from said immunized host animal.

The nucleic acid molecules of the present invention may be used for the manufacture of a medicament for prevention, treatment or amelioration of a medical condition. In a specific embodiment, the noncoding regions are transcription regulatory regions. The transcription regulatory regions may be used to produce a heterologous peptide by expressing in a host cell, said transcription regulatory region operably linked to a polynucleotide encoding the heterologous polypeptide and recovering the expressed heterologous polypeptide.

The polynucleotides of the present invention may be used to diagnose a pathological condition in a subject comprising (a) determining the presence or absence of a mutation in the polynucleotides of the present invention and (b) diagnosing a pathological condition or a susceptibility to a pathological condition based on the presence or absence of said mutation.

The invention is further directed to kits and/or microarrays comprising the nucleic acids of the present invention. The kits may comprise microarrays. Furthermore, the kits of the present invention may comprise other sequences, e.g., cDNA sequences.

DEFINITIONS

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984,"Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise. The terms "polynucleotide(s)", "nucleic acid molecule(s)" and "nucleic acids" will be used interchangeably.

Furthermore, the following terms shall have the definitions set out below.

As defined herein "isolated" refers to material removed from its original environment and is thus altered "by the hand of man" from its natural state.

The amino acid residues described herein are preferred to be in the "L" isomeric form. However, residues in the "D" isomeric form can be substituted for any L-amino acid residue, as long as the desired functional is retained by the polypeptide. $NH_2$ refers to the free amino group present at the amino terminus of a polypeptide. COOH refers to the free carboxy group present at the carboxy terminus of a polypeptide.

"Nucleic acid construct" is defined herein, is a nucleic acid molecule, either single- or double-stranded, which is isolated from a naturally occurring gene or which has been modified to contain segments of nucleic acid which are combined and juxtaposed in a manner which would not otherwise exist in nature.

The term nucleic acid construct is synonymous with the term "expression cassette" when the nucleic acid construct contains all the control sequences required for expression of a coding sequence of the present invention.

The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) of the first open reading frame at the 5'-end of the mRNA and a transcription terminator sequence located just downstream of the open reading frame at the 3'-end of the mRNA. A coding sequence can include, but is not limited to, DNA, cDNA, and recombinant nucleic acid sequences.

A "heterologous" region of a recombinant cell is an identifiable segment of nucleic acid within a larger nucleic acid molecule that is not found in association with the larger molecule in nature.

An "expression vector" may be any vector (e.g., a plasmid or virus) which can be conveniently subjected to recombinant DNA procedures and can bring about the expression of the nucleic acid sequence.

An "origin of replication" refers to those DNA sequences that participate in DNA synthesis.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence. Transcriptional and translational control sequences are DNA regulatory sequences, such as promoters, enhancers, polyadenylation signals, terminators, and the like, that provide for the expression of a coding sequence in a host cell.

A "signal sequence" can be included before the coding sequence of the mature polypeptide. This sequence encodes a signal peptide, N-terminal to the mature polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

It should be appreciated that also within the scope of the present invention are nucleic acid sequences encoding the polypeptide(s) of the present invention, which code for a polypeptide having the same amino acid sequence as the sequences disclosed herein, but which are degenerate to the nucleic acids disclosed herein. By "degenerate to" is meant that a different three-letter codon is used to specify a particular amino acid.

The term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

A nucleic acid molecule is "operatively linked" to an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

The term "stringent hybridization conditions" are known to those skilled in the art and can be found in Current Protocols in Molecular Biology, John Wiley & Sons, N.Y. (1989), 6.3.1-6.3.6. A preferred, non-limiting example of stringent hybridization conditions is hybridization in 6× sodium chloride/sodium citrate (SSC) at about 45° C., followed by one or more washes in 0.2.× SSC, 0.1% SDS at 50° C., preferably at 55° C., and more preferably at 60° C. or 65° C.

As used herein, "Arrays" or "Microarrays" refers to an array of distinct polynucleotides or oligonucleotides deposited on a substrate, such as paper, nylon or other type of membrane, filter, chip, glass slide, or any other suitable solid support. In one embodiment, the microarray is prepared and used according to the methods described in U.S. Pat. No. 5,837,832, PCT application WO95/11995, Lockhart et al. (1996; Nat. Biotech. 14: 1675-1680) and Schena et al. (1996; Proc. Natl. Acad. Sci. 93: 10614-10619). In other embodiments, such arrays are produced by the methods described by Brown et al., U.S. Pat. No. 5,807,522.

As defined herein, a "gene" is the segment of DNA involved in producing a polypeptide chain; it includes regions preceding and following the coding region, as well as intervening sequences (introns) between individual coding segments (exons).

As defined herein, "unique to" means a sequence that only occurs once in a genome.

DETAILED DESCRIPTION OF THE INVENTION

The invention is directed to isolated genomic polynucleotide fragments that encode human resistin and human syntaxin binding protein 2, which in a specific embodiment are the human resistin and human syntaxin binding protein 2 genes, as well as vectors and hosts containing these fragments and polynucleotide fragments hybridizing to noncoding regions, as well as antisense oligonucleotides to these fragments. The genomic polynucleotide fragments of the present invention may contain both sequences encoding resistin and syntaxin binding protein 2 and specifically may contain SEQ ID NO:3 and/or 4 or portions of SEQ ID NO:3 and/or 4.

The polynucleotides of the present invention may be in the form of RNA or in the form of DNA, which DNA includes genomic DNA and synthetic DNA. The DNA may be double-stranded or single-stranded and if single stranded may be the coding strand or non-coding strand. The genes encoding human resistin and human syntaxin binding protein 2 are disposed in the chromosome 19 genomic clones of accession numbers AC008763, gi 13699420, last contig (nucleotides 141174-194036), and AC021153, gi 8570240, reverse complement of contig 17 (nucleotides 77433-94571). A composite of these two contigs, corrected for overlapping sequence, is prepared to yield a 64,700 base pair sequence. In the latter composite, the resistin gene is disposed in nucleotides 1-38587 (SEQ ID NO:3). The syntaxin binding protein 2 gene is disposed in the last 30943 nucleotides (SEQ ID NO:4).

The polynucleotides of the invention are naturally occurring polynucleotide sequences having at least a 95% identity and may have a 96%, 97%, 98%, 99%, 99.5% or 99.9% identity to the polynucleotides depicted in SEQ ID NOS:3, 4 or 5 as well as the polynucleotides in reverse sense orientation, or the polynucleotide sequences encoding the human resistin and human syntaxin binding protein 2 polypeptides depicted in SEQ ID NOS:1 or 2 respectively.

The comparison of sequences and determination of percent identity and similarity between two sequences can be accomplished using a mathematical algorithm. (Lesk, A. M., ed., 1988, Computational Molecular Biology, Oxford University Press, New York; Smith, D. W., ed., 1993, Biocomputing: Informatics and Genome Projects, Academic Press, New York; Griffin, A. M., and Griffin, H. G., eds , 1994, Computer Analysis of Sequence Data, Part 1, Humana Press, New Jersey; von Heinje, G., 1987, Sequence Analysis in Molecular Biology, Academic Press; and Gribskov, M. and Devereux, J., eds., 1991, Sequence Analysis Primer, M Stockton Press, New York). In a preferred embodiment, the percent identity between two amino acid sequences is determined using the Needleman and Wunsch (1970, J. Mol. Biol. 48:444-453) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux et al., 1984, Nucleic Acids Res. 12:387) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of Myers and Miller (1989, CABIOS, 4:11-17) which has been incorporated into the ALIGN program (version 2.0), using a PAM120 weight residue table, a gap length penalty of 12 and a gap penalty of 4.

The nucleic acid sequences of the present invention can further be used as a "query sequence" to perform a search against sequence databases to, for example, identify other family members or related sequences. Such searches can be performed using the BLASTN and BLASTX programs (version 2.0) of Altschul, et al. (1990, J. Mol. Biol. 215:403-410). BLAST nucleotide searches can be performed with the BLASTN program, score=100, wordlength=12 to obtain nucleotide sequences homologous to the nucleic acid molecules of the invention. BLASTN protein searches can be performed with the BLASTX program, score=50, wordlength=3 to obtain amino acid sequences homologous to the proteins of the invention. To obtain gapped alignments for comparison purposes, Gapped BLASTN can be utilized as described in Altschul et al. (1997, Nucleic Acids Res. 25:3389-3402). When utilizing BLAST and gapped BLAST programs, the default parameters of the respective programs (e.g., BLASTX and BLASTN) can be used.

The invention also encompasses polynucleotides that hybridize to the polynucleotides depicted in SEQ ID NOS: 3, 4 and/or 5. This polynucleotide may have a maximum length of SEQ ID NOS: 3, 4 and/or 5. A polynucleotide "hybridizes" to another polynucleotide, when a single-stranded form of the polynucleotide can anneal to the other polynucleotide under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a temperature of 42° C., can be used, e.g., 5×SSC, 0.1% SDS, 0.25% milk, and no formamide; or 40% formamide, 5×SSC, 0.5% SDS). "Stringent hybridization conditions" can be found in Current Protocols in Molecular Biology, John Wiley & Sons, N.Y. (1989), 6.3.1-6.3.6. A preferred, non-limiting example of stringent hybridization conditions is hybridization in 6× sodium chloride/sodium citrate (SSC) at about 45° C., followed by one or more washes in 0.2.X SSC, 0.1% SDS at 50° C., preferably at 55° C., and more preferably at 60° C. or 65° C.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or complementarity between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA.

The invention is further directed to a nucleic acid construct comprising the nucleic acid molecules of the present invention. The nucleic acid sequence encoding the desired polypeptide, whether in fused or mature form, and whether or not containing a signal sequence to permit secretion, may be ligated into expression vectors suitable for any convenient host. The vector includes a plasmid, single or double stranded phage, a single or double stranded RNA or DNA viral vector, or artificial chromosome, such as a BAC, PAC, YAC, or MAC.

Polynucleotide and Polypeptide Variants

The invention is directed to both polynucleotide and polypeptide variants. A "variant" refers to a polynucleotide or polypeptide differing from the polynucleotide or polypeptide of the present invention, but retaining essential properties thereof. Generally, variants are overall closely similar and in many regions, identical to the polynucleotide or polypeptide of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5 or 1-2 amino acids are substituted, deleted, or added in any combination are also preferred.

The invention also encompasses allelic variants of said polynucleotides. An allelic variant denotes any of two or more alternative forms of a gene occupying the same chromosomal locus. Allelic variation arises naturally through mutation, and may result in polymorphism within populations and is thought to frequently occur. Gene mutations can be silent (no change in the encoded polypeptide) or may encode polypeptides having altered amino acid sequences. An allelic variant has a high homology to the original gene sequence. An allelic variant of a polypeptide is a polypeptide encoded by an allelic variant of a gene.

The amino acid sequences of the variant polypeptides may differ from the amino acid sequences depicted in SEQ ID NOS:1 or 2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine) Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

Noncoding Regions

The invention is further directed to polynucleotide fragments containing or hybridizing to noncoding regions of the human resistin and human syntaxin binding protein 2 genes. These include but are not limited to an intron, a 5'-non-coding region, a 3'-non-coding region (see Tables 1-2), as well as transcription factor binding sites (see Table 3).

The invention is further directed to polynucleotide fragments or nucleic acid molecules containing or hybridizing to contiguous exon/intron and intron/exon sequences of human resistin or human syntaxin binding protein 2 genes. These sequences encompass each splice site, where the intron is removed, the exon-intron junction and additionally includes the consensus sequence spanning the exon and intron sequences immediately adjacent to the splice site: The fragments are at least 20 nucleotides in length and in one embodiment contain at least 10 nucleotides of intron sequences. Thus, the invention would encompass a nucleic acid molecule that contains or hybridizes to a polynucleotide fragment that combines contiguous coding and noncoding nucleic acid sequences of SEQ ID NO:3 or 4. Further, the polynucleotide fragments of the present invention may contain more than one exon-intron and/or intron-exon regions.

The polynucleotide fragment may be a short polynucleotide fragment which is between about 8 nucleotides to about 20 or 40 nucleotides in length. Such shorter fragments may be useful for diagnostic purposes. Such short polynucleotide fragments are also preferred with respect to polynucleotides or nucleic acid molecules containing or hybridizing to polynucleotides or nucleic acid molecules containing noncoding regions including but not limited to 5' and 3' noncoding region, intron regions, contiguous exon-intron and intron-exon regions. Alternatively larger fragments, e.g., of about 50,60,100,150,200,300, 400,500,600,750,800,900,1000,1,500,2000,3000,4000,5000 or about 10000 nucleotides in length may be used.

TABLE 1

Exon/Intron Organization of the Resistin Gene in Genomic SEQ ID NO: 3 (Reverse Strand Coding).

| EXON | Nucleotide No. | Amino Acid No. |
|---|---|---|
| Stop Codon | 19611-19613 | |
| 3 | 19614-19742 | 108-66 |
| 2 | 20063-20140 | 65-40 |
| 1 | 20517-20633 | 39-1 |

TABLE 2

Exon/Intron Organization of the Syntaxin Binding Protein 2 Gene in Genomic SEQ ID NO: 4 (Reverse Strand Coding).

| Exon | Nucleotide No. | Amino Acid No. |
|---|---|---|
| Stop Codon | 8391-8393 | |
| 19 | 8394-8477 | 593-566 |
| 18 | 8691-8849 | 565-513 |
| 17 | 8956-9039 | 512-485 |
| 16 | 9857-9952 | 484-453 |
| 15 | 10895-11005 | 452-416 |
| 14 | 11450-11590 | 415-369 |
| 13 | 12959-13036 | 368-343 |
| 12 | 13153-13221 | 342-320 |
| 11 | 13378-13434 | 319-301 |
| 10 | 13667-13774 | 300-265 |
| 9 | 13870-13998 | 264-222 |
| 8 | 14083-14166 | 221-194 |
| 7 | 14347-14502 | 193-142 |
| 6 | 15204-15302 | 141-109 |
| 5 | 15393-15470 | 108-83 |
| 4 | 16394-16471 | 82-57 |
| 3 | 17102-17182 | 56-30 |
| 2 | 17426-17476 | 29-13 |
| 1 | 19016-19051 | 12-1 |

TABLE 3

NUMBERS OF TRANSCRIPTION FACTOR BINDING SITES ON GENES THAT ENCODE RESISTIN AND SYNTAXIN BINDING PROTEIN 2 (STXBP2).

| BINDING SITES | RESISTIN | STXBP2 |
|---|---|---|
| AP1_C | 6 | 2 |
| AP4_Q5 | 3 | 4 |
| AP4_Q6 | 3 | 4 |
| CAAT_01 | 7 | 4 |
| CREBP1CJUN_01 | 3 | |
| CREB_01 | 2 | |
| DELTAEF1_01 | 12 | 7 |
| GATA_C | | 2 |
| GC_01 | | 2 |
| GKLF_01 | 2 | 2 |
| HFH3_01 | 2 | |
| IK2_01 | 3 | |
| LMO2COM_01 | 5 | 7 |
| LMO2COM_02 | 3 | 4 |
| LYF1_01 | 36 | 14 |
| MYOD_Q6 | 17 | 11 |
| MZF1_01 | 51 | 50 |

TABLE 3-continued

NUMBERS OF TRANSCRIPTION FACTOR BINDING SITES ON GENES THAT ENCODE RESISTIN AND SYNTAXIN BINDING PROTEIN 2 (STXBP2).

| BINDING SITES | RESISTIN | STXBP2 |
|---|---|---|
| NFAT_Q6 | 3 | |
| NKX25_01 | 30 | 14 |
| NMYC_01 | | 3 |
| PADS_C | 2 | |
| S8_01 | | 2 |
| SOX5_01 | 5 | 6 |
| SP1_Q6 | | 3 |
| SREBP1_01 | 2 | |
| TCF11_01 | 17 | 7 |
| USF_01 | 14 | 14 |
| USF_C | 18 | 14 |

In a specific embodiment, such noncoding sequences are expression control sequences. In a more specific embodiment of the invention, the expression control sequences may be operatively linked to a polynucleotide encoding a heterologous polypeptide. Such expression control sequences may be about 50-200 nucleotides in length and specifically about 50, 100, 200, 500, 600, 1000 or 2000 nucleotides in length. The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription or RNA processing (triple helix (see Lee et al., Nucl. Acids Res., 6:3073 (1979); Cooney et al, Science, 241:456 (1988); and Dervan et al., Science, 251: 1360 (1991)), thereby preventing transcription and the production of said polypeptides.

Expression of Polypeptides

Isolated Polynucleotide Sequences

The human chromosome 19 genomic clones of accession numbers AC008763, gi 13699420, last contig (nucleotides 141174-194036) and AC021153, gi 8570249, reverse complement of contig 17 (nucleotides 77433-94571) have been discovered to contain the human resistin and human syntaxin binding protein 2 genes by Genscan analysis (Burge et al., 1997, J. Mol. Biol. 268:78-94), BLAST2 and TBLASTN analysis (Altschul et al., 1997, Nucl. Acids Res. 25:3389-3402). The sequences of AC008763, gi 13699420, and AC021153, gi 8570249 are compared to the human resistin and syntaxin cDNA sequences, accession numbers AF352730 (resistin) and AF205952. It has been found that resistin is disposed immediately adjacent to the syntaxin binding protein 2 gene. A composite of these two contigs, corrected for overlapping sequence, is prepared to yield a 64,700 base pair sequence (SEQ ID NO:5). In the latter composite, the resistin gene is disposed in nucleotides 1-38587 (SEQ ID NO:3). The syntaxin binding protein 2 gene is disposed in the last 30943 nucleotides (SEQ ID NO:4).

The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) or long range PCR may be used. In a specific embodiment, 5'- or 3'-non-coding portions of the gene may be identified by methods including but are not limited to, filter probing, clone enrichment using specific probes and protocols similar or identical to 5'- and 3'-"RACE" protocols which are well known in the art. For instance, a method similar to 5'-RACE is available for generating the missing 5'-end of a desired full-length transcript. (Fromont-Racine et al., 1993, Nucl. Acids Res. 21:1683-1684).

Once the DNA fragments are generated, identification of the specific DNA fragment containing the desired human resistin and/or syntaxin gene may be accomplished in a number of ways. For example, if an amount of a portion of a human resistin or syntaxin gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a hybridizable probe having a nucleotide sequence corresponding to at least a 10, and preferably a 15, nucleotide fragment of the sequences depicted in SEQ ID NO:2. Preferably, a fragment is selected that is unique to the polypeptides of the invention. Methods are commonly known in the art for preparing such unique sequences and are reviewed in Stoughton, 2005, Annu. Rev. Biochem. 74:53-82. Those DNA fragments with substantial homology to the probe will hybridize. As noted above, the greater the degree of homology, the more stringent hybridization conditions can be used. In one embodiment, low stringency hybridization conditions are used to identify a homologous human resistin or syntaxin polynucleotide. However, in a preferred aspect, and as demonstrated experimentally herein, a nucleic acid encoding a polypeptide of the invention will hybridize to a nucleic acid derived from the polynucleotide sequence depicted in SEQ ID NO:2 or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the human resistin or syntaxin polynucleotide.

A gene encoding human resistin or syntaxin polypeptide can also be identified by mRNA selection, i.e., by nucleic acid hybridization followed by in vitro translation. In this procedure, fragments are used to isolate complementary mRNAs by hybridization. Immunoprecipitation analysis or functional assays of the in vitro translation products of the products of the isolated mRNAs identifies the mRNA and, therefore, the complementary DNA fragments, that contain the desired sequences.

Nucleic Acid Constructs

The present invention also relates to nucleic acid constructs comprising a polynucleotide sequence containing the exon/intron segments of the human resistin and/or syntaxin gene operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) and a transcription terminator sequence located just downstream of the open reading frame at the 3'-end of the mRNA. A coding sequence can include, but is not limited to, DNA, cDNA, and recombinant nucleic acid sequences.

The isolated polynucleotide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequence may be an appropriate promoter sequence, a nucleic acid sequence which is recognized by a host cell for expression of the nucleic acid sequence. The promoter sequence contains transcriptional control sequences that regulate the expression of the polynucleotide. The promoter may be any nucleic acid sequence that shows transcriptional activity in the host cell of choice including mutant, truncated, and hybrid promoters, and may be obtained from genes encoding extracellular or intracellular polypeptides either homologous or heterologous to the host cell.

The control sequence may also be a suitable transcription terminator sequence, a sequence recognized by a host cell to terminate transcription. The terminator sequence is operably linked to the 3'-terminus of the nucleic acid sequence encoding the polypeptide. Any terminator which is functional in the host cell of choice may be used in the present invention.

The control sequence may also be a suitable leader sequence, a nontranslated region of an mRNA which is important for translation by the host cell. The leader sequence is operably linked to the 5'-terminus of the nucleic acid sequence encoding the polypeptide. Any leader sequence that is functional in the host cell of choice may be used in the present invention.

The control sequence may also be a polyadenylation sequence, a sequence which is operably linked to the 3'-terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region, which codes for an amino acid sequence linked to the amino terminus of the polypeptide which can direct the encoded polypeptide into the cell's secretory pathway. The 5'-end of the coding sequence of the nucleic acid sequence may inherently contain a signal peptide-coding region naturally linked in translation reading frame with the segment of the coding region which encodes the secreted polypeptide. Alternatively, the 5'-end of the coding sequence may contain a signal peptide coding region which is foreign to the coding sequence. The foreign signal peptide-coding region may be required where the coding sequence does not normally contain a signal peptide-coding region. Alternatively, the foreign signal peptide-coding region may simply replace the natural signal peptide-coding region in order to obtain enhanced secretion of the polypeptide. However, any signal peptide-coding region which directs the expressed polypeptide into the secretory pathway of a host cell of choice may be used in the present invention.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

Both eukaryotic and prokaryotic host systems are presently used in forming recombinant polypeptides. The polypeptide is then isolated from lysed cells or from the culture medium and purified to the extent needed for its intended use. Purification may be by techniques known in the art, for example, differential extraction, salt fractionation, chromatography on ion exchange resins, affinity chromatography, centrifugation, and the like. See, for example, Methods in Enzymology for a variety of methods for purifying proteins. Both prokaryotic and eukaryotic host cells may be used for expression of desired coding sequences when appropriate control sequences, which are compatible with the designated host, are used. Bacterial cells include, but are not limited to, *E. coli, Streptomyces*, and *Salmonella typhimurium*. Expression control sequences for prokaryotes include promoters, optionally containing operator portions, and ribosome binding sites.

Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection. Commonly used prokaryotic control sequences include the Beta-lactamase (penicillinase) and lactose promoter systems, the tryptophan (trp) promoter system and the lambda-derived $P_L$ promoter and N gene ribosome binding site and the hybrid TAC promoter derived from sequences of the trp and lac UV5 promoters. The foregoing systems are particularly compatible with *E. coli*; if desired, other prokaryotic hosts such as strains of *Bacillus* or *Pseudomonas* may be used, with corresponding control sequences.

Eukaryotic cells include, but are not limited to, yeast, insect cells such as *Drosophila*, animal cells such as COS and CHO cells, and plant cells. *Saccharomyces cerevisiae* and *Saccharomyces carlsbergensis* are the most commonly used yeast hosts, and are convenient fungal hosts. Yeast compatible vectors carry markers that permit selection of successful transformants by conferring prototrophy to auxotrophic mutants or resistance to heavy metals on wild-type strains. Yeast compatible vectors may employ the 2 micron origin of replication, the combination of CEN3 and ARS1 or other means for assuring replication, such as sequences which will result in incorporation of an appropriate fragment into the host cell genome. Examples of vectors for expression in yeast e.g., *S. cerevisiae* include pYepSec1 (Baldari, et al., 1987, EMBO J. 6:229-234; pMFa (Kuijan et al., 1982, Cell 30:933-943), pJRY88 (Schultz et al., 1987, Gene 54:113-123), and pYES2 (Invitrogen Corporation, San Diego, Calif.). The nucleic acid molecules can also be expressed in insect cells using, for example, baculovirus expression vectors. Baculovirus vectors available for expression of proteins in cultured insect cells (e.g., Sf 9 cells) include the pAc series (Smith et al., 1983, Mol. Cell. Biol. 3:2156-2165) and the pVL series (Lucklow et al., 1989, Virology 170:31-39).

Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines. Suitable promoters for mammalian cells are also known in the art and include viral promoters such as that from Simian Virus 40 (SV40), Rous sarcoma virus (RSV), adenovirus (ADV), and bovine papilloma virus (BPV). Mammalian cells may also require terminator sequences and poly A addition sequences; enhancer sequences which increase expression may also be included, and sequences which cause amplification of the gene may also be desirable. These sequences are known in the art.

It will be understood that not all vectors, expression control sequences and hosts will function equally well to express the polynucleotide sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the nucleic acid molecules of this invention on fermentation or in large scale animal culture.

The polypeptides may be detected using methods known in the art that are specific for the polypeptides. These detection methods may include use of specific antibodies, formation of an enzyme product, or disappearance of an enzyme substrate. An enzyme assay may be used to determine the activity of the polypeptide. Resistin can be determined using the immunoassay procedure described by Steppan et al., Nature 409: 307-12, 2001.The human syntaxin binding protein 2 may be detected by its ability to bind to syntaxins 1A, 2 and 3 but not to syntaxin 4 (Katagiri et al., J. Biol. Chem. 270: 4963-6, 1995).

Antibodies

According to the invention, the human resistin or human syntaxin binding protein 2 polypeptides produced according to the method of the present invention may be used as an immunogen to generate any of these antibodies. Such antibodies include but are not limited to polyclonal, monoclonal, chimeric, single chain, Fab fragments, and a Fab expression library.

Various hosts may be used and include but are not limited to goats, rabbits, rats, mice, humans, and others. These hosts may be immunized by injection with the polypeptides of the present invention or any fragment or oligopeptide thereof which has immunogenic properties (e.g., 5-10 peptide fragments with immunogenic properties). Various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are especially preferable in humans.

Monoclonal antibodies to the said polypeptides and peptides of the present invention may be prepared using any technique which provides for the production of antibody molecules by continuous cell lines in culture. These include, but are not limited to, the hybridoma technique, the human B-cell hybridoma technique, and the EBV-hybridoma technique. See, e.g., Kohler, et al., 1975, Nature, 256: 495-497; Kozbor et al., 1985, J. Immunol. Methods 81: 31-42; Cote et al., 1983, Proc. Natl. Acad. Sci. USA 80: 2026-2030; Cole et al., 1984, Mol. Cell. Biol. 62: 109-120.

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between the polypeptide(s) of the present invention and its specific antibody.

Antibodies may be conjugated to a solid support suitable for a diagnostic assay (e.g., beads, plates, slides or wells formed from materials such as latex or polystyrene) in accordance with known techniques, such as precipitation. Antibodies may likewise be conjugated to detectable groups such as radiolabels (e.g. $^{35}S$, $^{125}I$, $^{131}I$) enzyme labels (e.g., horseradish peroxidase, alkaline phosphatase), and fluorescent labels (e.g., fluorescein) in accordance with known techniques.

Microarrays and Kits

The microarray generally contains a large number of single-stranded nucleic acid sequences, fixed to a solid support, wherein at least one of which is a nucleic acid hybridizing to at least one 20 (and/or larger) nucleotide fragment unique to a (forward or reverse strand) noncoding region of SEQ ID NO:3 or 4. The fragment may hybridize to the coding and noncoding region. Alternatively larger fragments, e.g., of about 50, 70, 75, 150, 500, 600, 750, 800, 850, 900 or about 950 nucleotides in length may be used. In yet another embodiment, BAC or YAC arrays may be used containing full length cDNA or genomic sequences. The kit may also comprise coding sequences of SEQ ID NO: 3 or 4.

In order to produce oligonucleotides to a known sequence for a microarray or detection kit, the nucleic acid of interest is typically examined using a computer algorithm which starts at the 5' or at the 3' end of the nucleotide sequence. Typical algorithms will then identify oligomers of defined length that are unique to said nucleic acid, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers may be synthesized at designated areas on a solid support using a light-directed chemical process or prepared elsewhere and then deposited on the solid support. The solid support may be paper, nylon or other type of membrane, filter, chip, glass slide or any other suitable solid support.

The microarrays of the present invention may be used to identify nucleic acids encoding resistin and/or syntaxin.

In another embodiment, the invention is directed to a kit comprising at least one nucleic acid comprising at least 20 nucleotides hybridizing under stringent conditions to a noncoding region of the nucleic acid of the present invention. The kit may also comprise a polynucleotide fragment encompassing the coding region of resistin or syntaxin. In a more specific embodiment, the kit comprises a probe or primer comprising 50, 70, 75, 150, 500, 600, 750, 800, 850, 900 or about 950 nucleotides in length may be used. In yet another embodiment, BAC, PAC or YAC arrays may be used containing full length genomic sequences. The nucleic acid may act as a probe or primer and may be labeled with a detectable label. The detectable label may, for example, be a radioactive label, fluorescer, antibody or enzyme. The kit may further comprise the label. Alternatively, the kit may comprise a microarray. The probes or primers of the present invention may act as a primer to synthesize further nucleic acid probes.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments disclosed herein. Examples of such assays can be found in Chard, 1986, An Introduction to Radioimmunoassay and Related Techniques, Elsevier Science Publishers, Amsterdam, The Netherlands; Bullock, G. R. et al., Techniques in Immunocytochemistry, Academic Press, Orlando, Fla. Vol. 1 (1982), Vol. 2 (1983), Vol. 3 (1985); Tinsel, Practice and Theory of Enzyme Immunoassays: Laboratory Techniques in Biochemistry and Molecular Biology, Elsevier Science Publishers, Amsterdam, The Netherlands (1985).

Therapeutic Uses

Antisense Oligonucleotides and Mimetics

The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription or RNA processing (triple helix (see Lee et al., Nucl. Acids Res., 6:3073 (1979); Cooney et al, Science, 241:456 (1988); and Dervan et al., Science, 251: 1360 (1991)), thereby preventing transcription and the production of said polypeptides. As defined herein, a "mimetic" is an oligonucleotide having non-naturally occurring portions which function similarly to naturally occurring oligonucleotides and may include peptide-nucleic acids (PNAs). Modifications may occur at the phosphate linkage (e.g., methylphosphonates, phosphothioates) or sugar linkage, cyclobutyl moieties in place of the pentofuranosyl sugar or at the purine or pyrimidine bases themselves as described in US 2004/0214325.

The antisense oligonucleotides or mimetics of the present invention may be used to decrease levels of a polypeptide. For example, human resistin inhibits actions of insulin. Therefore, the human resistin antisense oligonucleotides of the present invention could be used to treat insulin-resistant forms of type 2 diabetes. Human syntaxin binding protein 2 plays a role in vesicle trafficking, thus its antisense sequences may be used to treat endocrine tumors such as insulinomas from which hormones such as insulin are secreted in health-threatening excess.

The antisense oligonucleotides of the present invention may be formulated into pharmaceutical compositions. These compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ as found to be effective in in vitro and in vivo animal models.

In general, dosage is from 0.01 ug to 10 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 10 g per kg of body weight, once or more daily, to once every 20 years.

Gene Therapy

As noted above, human resistin inhibits actions of insulin, and human syntaxin binding protein 2 plays a role in secretory vesicle trafficking. Therefore, the human resistin gene may be used to modulate conditions in which insulin is secreted in excess, as in functional insulinomas. The human syntaxin binding protein 2 gene may be used to stimulate secretory vesicle release from hypofunctional endocrine tissues such as the pancreas islet cells in juvenile diabetes.

As described herein, the polynucleotide of the present invention may be introduced into a patient's cells for therapeutic uses. As will be discussed in further detail below, cells can be transfected using any appropriate means, including viral vectors, as shown by the example, chemical transfectants, or physico-mechanical methods such as electroporation and direct diffusion of DNA. See, for example, Wolff, Jon A, et al., "Direct gene transfer into mouse muscle in vivo," Science, 247, 1465-1468, 1990; and Wolff, Jon A, "Human dystrophin expression in mdx mice after intramuscular injection of DNA constructs," Nature, 352, 815-818, 1991. As used herein, vectors are agents that transport the gene into the cell without degradation and include a promoter yielding expression of the gene in the cells into which it is delivered. As will be (1) (2)discussed in further detail below, promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes: a) Biological agents derived from viral, bacterial or other sources; b) Chemical physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells. Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression. Polynucleotides are inserted into vector genomes using methods well known in the art.

Retroviral vectors are the vectors most commonly used in clinical trials, since they carry a larger genetic payload than other viral vectors. However, they are not useful in non-proliferating cells. Adenovirus vectors are relatively stable and easy to work with, have high titers, and can be delivered in aerosol formulation. Pox viral vectors are large and have several sites for inserting genes, they are thermostable and can be stored at room temperature.

Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1a promoter or the Ad2 major late promoter (MLP). Similarly, those of ordinary skill in the art can construct adenoviral vectors utilizing endogenous or heterologous poly A addition signals.

Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN" and LIPOFECTACE", which are formed of cationic lipids such as N-[1-(2,3 dioleyloxy)-propyl]-n,n,n-trimethylammonium chloride (DOTMA) and dimethyl dioctadecylammonium bromide (DDAB). Numerous methods are also published for making liposomes, known to those skilled in the art.

For example, Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA that, generally, has a negative charge. Cationic lipids have also been shown to mediate intracellular delivery of plasmid DNA (Feigner and Ringold, Nature 337:387 (1989)). Intravenous injection of cationic lipid-plasmid complexes into mice has been shown to result in expression of the DNA in lung (Brigham et al., Am. J. Med. Sci. 298:278 (1989)). See also, Osaka et al., J. Pharm. Sci. 85(6):612-618 (1996); San et al., Human Gene Therapy 4:781-788 (1993); Senior et al., Biochemica et Biophysica Acta 1070:173-179 (1991); Kabanov and Kabanov, Bioconjugate Chem. 6:7-20 (1995); Remy et al., Bioconjugate Chem. 5:647-654 (1994); Behr, J-P., Bioconjugate Chem 5:382-389 (1994); Behr et al., Proc. Natl. Acad. Sci., USA 86:6982-6986 (1989); and Wyman et al., Biochem. 36:3008-3017 (1997).

Cationic lipids are known to those of ordinary skill in the art. Representative cationic lipids include those disclosed, for example, in U.S. Pat. No. 5,283,185; and e.g., U.S. Pat. No. 5,767,099. In a preferred embodiment, the cationic lipid is N.sup.4-spermine cholesteryl carbamate (GL-67) disclosed in U.S. Pat. No. 5,767,099. Additional preferred lipids include N4 Dspermidine cholestryl carbamate (GL-53) and 1-(N-4-spermind)-2,3-dilaurylglycerol carbamate (GL-89).

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule.

Invention vectors may be delivered to the target cells in a suitable composition, either alone, or complexed, as provided above, comprising the vector and a suitably acceptable carrier. The vector may be delivered to target cells by methods known in the art, for example, intravenous, intramuscular, intranasal, subcutaneous, intubation, lavage, and the like. The vectors may be delivered via in vivo or ex vivo applications. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

In a specific embodiment, the vector is transfected into antigen-presenting cells. Suitable sources of antigen-presenting cells (APCs) include, but are not limited to, whole cells such as dendritic cells or macrophages; purified MHC class I molecule complexed to beta2-microglobulin and foster antigen-presenting cells. In a specific embodiment, the vectors of the present invention may be introduced into T cells or B cells using methods known in the art (see, for example, Tsokos and Nepom, 2000, J. Clin. Invest. 106:181-183).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims Various references are cited herein, the disclosures of which are incorporated by reference in their entireties.

What is claimed is:

1. An isolated genomic nucleic acid molecule, said nucleic acid molecule selected from the group consisting of:
   (a) a nucleic acid molecule consisting of a nucleic acid sequence which has at least 99% identity to the nucleic acid molecule of SEQ ID NO:4 and which encodes a polypeptide having the amino acid sequence of SEQ ID NO:2, wherein said polypeptide binds to syntaxins 1A, 2 and 3 but not to syntaxin 4;
   (b) a fragment of the nucleic acid molecule of (a), said fragment comprising at least nucleotides 8391-19051 of SEQ ID NO:4 and which encodes a polypeptide having the amino acid sequence of SEQ ID NO:2, wherein said polypeptide binds to syntaxins 1A, 2 and 3 but not to syntaxin 4, and;
   (c) a full complement of (a) or (b) in a sample.

2. A nucleic acid construct comprising the nucleic acid molecule of claim 1.

3. A composition comprising the nucleic acid molecule of claim 1 and a carrier.

4. An isolated nucleic acid molecule consisting of a sequence segment of a nucleic acid molecule of claim 1, wherein said segment is 60-750 nucleotides in length consisting of a contiguous coding and non-coding nucleic acid sequence of SEQ ID NO:4 or a full complement of said isolated nucleic acid molecule.

5. A kit comprising the nucleic acid molecule of claim 1.

6. The kit according to claim 5, in which the nucleic acid molecule is labeled with a detectable substance.

7. A kit comprising the nucleic acid molecule of claim 4.

8. The kit according to claim 7, in which the nucleic acid molecule is labeled with a detectable substance.

9. A microarray comprising one or more of the nucleic acid molecules of claim 1.

10. A kit comprising the microarray of claim 9.

11. A microarray comprising one or more of the nucleic acid molecules of claim 4.

12. A kit comprising the microarray of claim 11.

13. An expression vector comprising the nucleic acid molecule of claim 1.

14. A recombinant host cell comprising the nucleic acid molecule of claim 1.

15. A method for obtaining a polypeptide having human syntaxin binding protein 2 activity comprising:
   (a) culturing the recombinant host cell of claim 14 under conditions that provide for the expression of said polypeptide and
   (b) recovering said expressed polypeptide.

16. A method of detecting the presence of a nucleic acid sequence of SEQ ID NO:4, its complementary sequence or unique fragment thereof in a sample, said method comprising contacting the sample with the nucleic acid molecule of claim 1 and determining whether the nucleic acid molecule binds to said nucleic acid sequence in the sample.

17. A method of identifying a nucleotide sequence variant of a 5'-noncoding region, 3'-noncoding region or intron region of SEQ ID NO:4 or its complementary sequence comprising
   (a) isolating genomic DNA from a sample and
   (b) determining the presence or absence of a nucleotide sequence variation in said genomic DNA by comparing the nucleotide sequence of SEQ ID NO:4 with the nucleotide sequence of the isolated genomic DNA and establishing if and where a difference occurs between the two nucleic acid sequences thereby identifying a nucleotide sequence variant of SEQ ID NO:4 or its complement.

18. The method according to claim 17, wherein said variant encodes a protein having human syntaxin 2 activity.

19. A method for detecting the presence of the nucleic acid molecule of claim 1 in a sample, comprising contacting the sample with a polynucleotide probe comprising at least 20 contiguous nucleotides that hybridizes to said nucleic acid molecule under stringent conditions and determining whether the polynucleotide probe binds to said nucleic acid molecule in the sample.

* * * * *

SEQUENCE LISTING

```
<160> NUMBER OF SEQ ID NOS: 5

<210> SEQ ID NO 1
<211> LENGTH: 108
<212> TYPE: PRT
<213> ORGANISM: Homo sapiens

<400> SEQUENCE: 1

Met Lys Ala Leu Cys Leu Leu Leu Pro Val Leu Gly Leu Leu Val
1               5                   10                  15

Ser Ser Lys Thr Leu Cys Ser Met Glu Glu Ala Ile Asn Glu Arg Ile
                20                  25                  30

Gln Glu Val Ala Gly Ser Leu Val Phe Arg Ala Ile Ser Ser Ile Gly
            35                  40                  45

Leu Glu Cys Gln Ser Val Thr Ser Arg Gly Asp Leu Ala Thr Cys Pro
    50                  55                  60

Arg Gly Phe Ala Val Thr Gly Cys Thr Cys Gly Ser Ala Cys Gly Ser
65                  70                  75                  80

Trp Asp Val Arg Ala Glu Thr Thr Cys His Cys Gln Cys Ala Gly Met
                85                  90                  95

Asp Trp Thr Gly Ala Arg Cys Cys Arg Val Gln Pro
            100                 105

<210> SEQ ID NO 2
<211> LENGTH: 593
<212> TYPE: PRT
<213> ORGANISM: Homo sapiens

<400> SEQUENCE: 2

Met Ala Pro Ser Gly Leu Lys Ala Val Val Gly Glu Lys Ile Leu Ser
1               5                   10                  15

Gly Val Ile Arg Ser Val Lys Lys Asp Gly Glu Trp Lys Val Leu Ile
                20                  25                  30

Met Asp His Pro Ser Met Arg Ile Leu Ser Ser Cys Cys Lys Met Ser
            35                  40                  45

Asp Ile Leu Ala Glu Gly Ile Thr Ile Val Glu Asp Ile Asn Lys Arg
    50                  55                  60

Arg Glu Pro Ile Pro Ser Leu Glu Ala Ile Tyr Leu Leu Ser Pro Thr
65                  70                  75                  80

Glu Lys Ser Val Gln Ala Leu Ile Lys Asp Phe Gln Gly Thr Pro Thr
                85                  90                  95

Phe Thr Tyr Lys Ala Ala His Ile Phe Phe Thr Asp Thr Cys Pro Glu
            100                 105                 110

Pro Leu Phe Ser Glu Leu Gly Arg Ser Arg Leu Ala Lys Val Val Lys
        115                 120                 125

Thr Leu Lys Glu Ile His Leu Ala Phe Leu Pro Tyr Glu Ala Gln Val
```

```
              130                 135                 140
Phe Ser Leu Asp Ala Pro His Ser Thr Tyr Asn Leu Tyr Cys Pro Phe
145                 150                 155                 160

Arg Ala Glu Glu Arg Thr Arg Gln Leu Glu Val Leu Ala Gln Gln Ile
                165                 170                 175

Ala Thr Leu Cys Ala Thr Leu Gln Glu Tyr Pro Ala Ile Arg Tyr Arg
            180                 185                 190

Lys Gly Pro Glu Asp Thr Ala Gln Leu Ala His Ala Val Leu Ala Lys
        195                 200                 205

Leu Asn Ala Phe Lys Ala Asp Thr Pro Ser Leu Gly Glu Gly Pro Glu
    210                 215                 220

Lys Thr Arg Ser Gln Leu Leu Ile Met Asp Arg Ala Ala Asp Pro Val
225                 230                 235                 240

Ser Pro Leu Leu His Glu Leu Thr Phe Gln Ala Met Ala Tyr Asp Leu
                245                 250                 255

Leu Asp Ile Glu Gln Asp Thr Tyr Arg Tyr Glu Thr Thr Gly Leu Ser
            260                 265                 270

Glu Ala Arg Glu Lys Ala Val Leu Leu Asp Glu Asp Asp Leu Trp
        275                 280                 285

Val Glu Leu Arg His Met His Ile Ala Asp Val Ser Lys Lys Val Thr
    290                 295                 300

Glu Leu Leu Arg Thr Phe Cys Glu Ser Lys Arg Leu Thr Asp Lys
305                 310                 315                 320

Ala Asn Ile Lys Asp Leu Ser Gln Ile Leu Lys Lys Met Pro Gln Tyr
                325                 330                 335

Gln Lys Glu Leu Asn Lys Tyr Ser Thr His Leu His Leu Ala Asp Asp
            340                 345                 350

Cys Met Lys His Phe Lys Gly Ser Val Glu Lys Leu Cys Ser Val Glu
        355                 360                 365

Gln Asp Leu Ala Met Gly Ser Asp Ala Glu Gly Glu Lys Ile Lys Asp
    370                 375                 380

Ser Met Lys Leu Ile Val Pro Val Leu Leu Asp Ala Ala Val Pro Ala
385                 390                 395                 400

Tyr Asp Lys Ile Arg Val Leu Leu Tyr Ile Leu Leu Arg Asn Gly
                405                 410                 415

Val Ser Glu Glu Asn Leu Ala Lys Leu Ile Gln His Ala Asn Val Gln
            420                 425                 430

Ala His Ser Ser Leu Ile Arg Asn Leu Glu Gln Leu Gly Gly Thr Val
        435                 440                 445

Thr Asn Pro Gly Gly Ser Gly Thr Ser Ser Arg Leu Glu Pro Arg Glu
    450                 455                 460

Arg Met Glu Pro Thr Tyr Gln Leu Ser Arg Trp Thr Pro Val Ile Lys
465                 470                 475                 480

Asp Val Met Glu Asp Ala Val Glu Asp Arg Leu Asp Arg Asn Leu Trp
                485                 490                 495

Pro Phe Val Ser Asp Pro Ala Pro Thr Ala Ser Ser Gln Ala Ala Val
            500                 505                 510

Ser Ala Arg Phe Gly His Trp His Lys Asn Lys Ala Gly Val Glu Ala
        515                 520                 525

Arg Ala Gly Pro Arg Leu Ile Val Tyr Val Met Gly Gly Val Ala Met
    530                 535                 540

Ser Glu Met Arg Ala Ala Tyr Glu Val Thr Arg Ala Thr Glu Gly Lys
545                 550                 555                 560
```

```
Trp Glu Val Leu Ile Gly Ser Ser His Ile Leu Thr Pro Thr Arg Phe
            565                 570                 575
Leu Asp Asp Leu Lys Ala Leu Asp Lys Lys Leu Glu Asp Ile Ala Leu
            580                 585                 590
Pro

<210> SEQ ID NO 3
<211> LENGTH: 38587
<212> TYPE: DNA
<213> ORGANISM: Homo sapiens

<400> SEQUENCE: 3
gtgcctctag aggatcccca tgcacagatt agaaaggtga gtcttggccg ggcagggtgg      60
ctcgtgcctg tcatcccagc gctgtaggac gccgaggtgg gtggatcacc tgccaggagt     120
ttaagaccat cctggtcaac atggcgaaac ccctctctac taaaaataca gaaattagcc     180
agtcatgatg gcgggcgcct gtaatcccag ctatttgaga ggctgaggtg ggagaatcac     240
ttgaacccag gaggcggagg ttgcagtgag ctgagatcgc gcactgcact ccagcctggg     300
cgacagagtg attctgtctc aacaaaataa ataaataaac aaacaaacaa ataaataagg     360
gtgagtcttg ggctgcaggg tatggggcac caaaatgagg taccggtccc caggcacaga     420
ctcaggatgg ggaacctggg gtgagaaggg agggtgcaga ctcagagggc tgccgggaac     480
tgggctcctt ctccccgccc catcccctga cccaaagcct tttgctccag caactgggct     540
ccaggggagc ccaccagccg gagccagggc gaggactgcg tgatgatgcg gggctccggt     600
cgctggaacg acgccttctg cgaccgtaag ctgggcgcct gggtgtgcga ccggctggcc     660
acatgcacgc cgccagccag cgaaggttcc gcggagtcca tgggacctga ttcaagacca     720
gaccctgacg gccgcctgcc cacccctct gccctctcc actcttgagc atggatacag     780
ccaggcccag agcaagaccc tgaagacccc caaccacggc ctaaaagcct ctttgtggct     840
gaaaggtccc tgtgacattt tctgccaccc aaacggaggc agctgacaca tctcccgctc     900
ctctatggcc ctgccttccc aggagtacac cccaacagca ccctctccag atgggagtgc     960
ccccaacagc accctctcca gatgagagta caccccaaca gcaccctctc cagatgagag    1020
tacaccccaa cagcaccctc tccagatgag agtacacccc aacagcaccc tctccagatg    1080
cagccccatc tcctcagcac cccaggacct gagtatcccc agctcaggtg gtgagtcctc    1140
ctgtccagcc tgcatcaata aaatggggca gtgatggcct cccacatttg tccccttctt    1200
ggaggcctgg ctgggtctgg tctctgggtg tggcacatgg gagctgggaa ttccagagtc    1260
tgatgcctga gaccaccttt gaaagttggg acatcagatc tttggccggg tgtggtggcc    1320
catgcctgta attccagcac tttgggaagt caaggcaggc gaatcatctg aggtcaggag    1380
ttcaagacca gcctggccaa catggcaaaa ccccgtctct attaaaaata caaaaattca    1440
gccgggcacg gtggctcacg cctgtaatcc cagcactttg ggaggccaag gcaggcggat    1500
cacaaggtca ggagatcgag accatcctgg ctaacacggt gaaactccgt ctctactaaa    1560
aatacaaaaa attagccggg cgtggcggcg tgtgcctgta gtcccagctg ctggggaggc    1620
tgaggcagga gaatggcgtg aacccgggag gtggagcttg cagtgagccg agattgcgcc    1680
actgcactcc agcctgggcg acagagcgag actccatctc aaaaaaaaaa aaaaaacaaa    1740
aacacaaaaa ttcgctgggc gtggtggtgc acaccgtaa tcctagctac tcaggaggct    1800
gaggcaggag aagtgcttga acctgggagg tggaggttgc aatgatctga gatcacgcca    1860
ctgtgacaga gcgagacccc aactaaataa atttaaaaag aaagaaagaa aattgggagc    1920
```

```
aagcagatgt ggtggctcat gcctgtaatc ccagcacttt gggaggctga attgagccga   1980
tcacttgaga ccaggagttc gagaccagcc tggccaacat agtgaaaccc cgtctctact   2040
aaaaaaaaaa tacaaaaatt agccaggcac ggtggcatgt gcctataatc ccagctactc   2100
gggaggctga ggcaggagaa tcacttgaac ctgggaggca gaggttgcag tgagccagga   2160
tcgtgctact gcactccagc ctgggtaaca gagtgagatt gcatgtcaaa aaaaaaaaa   2220
agaagaaaaa agaaacaaat tgaggagcaa ctgaagtaga attcgatctc ccgtttttat   2280
tttttcctgc tctatgacac ggagaatgtg caggacatga agcctctgag gtccaatggc   2340
cccttggaat actgtagggg aaggcggtgg atcaccctga ggcgggagg gcgtgagttg    2400
actcatggaa gtacccagag cagggcttag tacacagaag gcactcagta agtgctggct   2460
ggctggacag gctgatgggg agtgggcccg gtcaaccgga ggccatttcg ggtctggagg   2520
tgttaaccct actcagggtc tgggaggctg aggtggcacc agcctcacgc tcggccaagg   2580
tcgacccatg ccgaggccca cgggagggag gccaggagca cagggtcccc tctccacact   2640
cctctaccag tggctcaggc caacactggg gtcattgcac ctcttccctt tccctgaca   2700
acacctccag gtccaagacc ataagaaatg ccagtgggct ctgctgtcaa acggcgctca   2760
caatcactca ctgctcaccc cttctgccac tgcctcgact ggagcagtca cctccgcccg   2820
gggctctctc ttcactgccc cctttccaga agtttcctcc agctcagata aaaggccaaa   2880
gccagctgcg cacagtggct catgcctgtc atcccagcgc tttgggaggc tgaggtggga   2940
ggactgcttg agttcaggag tttgaggcca gcctgggcaa catagtgagg ccccatctct   3000
acaaaaaata caaaaactag aggtgtagtg atgggcaact tggtcccagc tgcttgggag   3060
gccgaggtgg gaggattgtg cccctgctct cagcctgggc gacagtgaga acctgtctca   3120
aaaaaaaga agaagaaaag agaaaaagcc agccaggtgc ggtggctcac gcctgtaatc   3180
ctagcacttt gggaggccaa ggcgggcaga tcacttgagg tcaggagttc agaccagcc   3240
tggccaacat ggtgaaaccc cgtctccact aaaaatacaa aaattagctg ggtgtggtgg   3300
cggatgccta tagtcccaac tattcaggag gctgaagcag gagaattgct tgaacccagg   3360
aggctgagat ctgagatcgc accactgcac tccagcctgg gcgacagagt gagactccat   3420
ctctaaataa taataataat aataattaat ctgtgtgacc atgggcacat gacttctttt   3480
ggaacctgcc tgtgaaatga gctgatgctg cttgcccagc tcaccaaggg ctggtgcctg   3540
gctcctcctc ctcctcttcc tctcacccac ccacctggag ggtccagggg aagaccttcc   3600
ttgcagccca gagcaccgta agttagagct gctgtgatca gaagctgccg aaccacaggc   3660
tcttctttct cttcatcctc ccttgcccca accccgggcc cagcctcata accctacagc   3720
ttgttcaaac gttttccctt ctcctcaagc cccctaactc accctcggtg gccggtgggg   3780
atggggcgtg ggaacagacc ctgggccctg cactcccagc ttacaaattc ccgcagcccc   3840
tcttcctccc tcccgatttc tctgacatcc ctcacagccc cgcctctgga cagaagaatg   3900
gccccctgccc tggccggccc tggaagcccc tctcgccagg gtctcagagg acctgcctgg   3960
ggctgcttag cccaaagcgt cctgcatttt gctctgaaat ccagcttctc agacaccatg   4020
ttcccctccc tccgtccccc atccaggact gtggtttctg tgtctgtgca gacgcccaga   4080
cctcctccaa gaactccaga ccccaaaccc caagacctgt gcatctgctg gccccctaga   4140
cgcctccccc tcattccaga ttcaggctat catcctgccc aagccctctc ccggcgcctc   4200
cctccacctc caacagccaa cagctattcc aggatcagcc ctggggctat gtgtggtggt   4260
tgctcaatgg tttcattcat cctagagacg ccaccttctc cccagtgtgc tgaagcccac   4320
```

```
cctgctcaat gcctcttgct aggatggctg agactgccct gaccaagccc tcagccctgg    4380
tccaccaggc agtccaacag agcatcctaa acaaatctag aggtgacacc gaccccttg     4440 gcccttctca taaccagtga ggggagccca gctgacagtc cctgcagttc cttttctgaa    4500
cagacctgtc tgttcacatt ctgggggcg gtggaaagga agcagggaag attggatcat     4560
ggttccccca aaaatctgg aagaactttc cttggggag aggaggagtt atcaggaacc      4620
aagtgtggtg aacaaaaagg gaaaggaaaa ttgcctgagg tgtaatacat tacttttttt    4680
ttctttttta agacagggtc tcactctgtt gctcaggctg gagtgccagt ggtgtgatct    4740
tggctcactt caacctccgc ctcccaggtt aagtgatcc tcctgcctta gcctcccaag     4800
tagctgggat tacaggtgcc tgccaccacg cccagctaat ttttgtattt ttagtaaaga    4860
tgggttttgc catgttgacc aggttggtct caaacttccg gcctcaagtg atctgcccac    4920
ctcggcctct caaagtgctg ggattacaga cataagtcgc cacgcctggc cttatttcaa    4980
attcttttag acaaggtctc actatgttgc ccaggctgga caccaacccc tggcctcaag    5040
cgatccttct gcctcggcct cctgaatagc tgggactcca ggtgtgcacc actgcacccc    5100
acttatttta aaatttttt aacaagggaa atgtgtttgt atcatcctgg actttaaaat     5160
taactttaaa gtattgacca gactggccaa cacagtgaaa cctcatctct actaaaaata    5220
caaaaaatta ggtagctggg actacaggaa tgcacctcca tgcccagcta attttttgtat   5280 ttttagtaga cagggttt caccatattg gccaggctgg ctcgaactcc tgacctcgtg      5340
atccgcctgc ctcggcctcc caaagtgctg ggattatagg cgtgagccac gcgcctgac     5400 cttttttgttt tttagatgga gtttcgctct tgttgcccag gctggagtgc aatggtgcaa    5460
tctcggctca ctgcaacctc cacctccgg gttggagcga ttctcctgcc tcagcctccc    5520
aagtagctgg gattacaggc atgtgccacc acacccggct aatgttttct attttagta     5580 gagacgggt tttgccatgt tagccaggct ggtctcgaac tcctgacttc aggtgatcca    5640
cctgcctcag cctcccaaag tgctgggatt acaggcgtga gccaccgcac gtggcccctc    5700
ctggtgattc tgatacccta aagcctgcat ctcaatctaa ggtccccagg aatcccctgg    5760
gggcctcgct aaaatgcacc ctcagattca gcagctctgg ggtgggcctg agactgcatt    5820
atggaccaac tcccagttga tgctgctact gctgatctac agaacacact ttgatttggc    5880
tcacgcctgt aaccccagca cttacggagg ccaaggtgga aggattgctt gaggccaaga    5940
gtttgagacc agcctgggca acctaataag agccccatc tctacaaaaa tttttaaaa     6000 attagctggg catggctggg cgccatggct cacgcctgta atcccagcac tttgggaagc    6060
cgaggtgggc agatcacgag gtgaggagat cgagaccatc ctggctaaca tggtgaaacc    6120
ccgtctctac taaaaatacg aaaaattagc caggtgtggt ggtgggcacc tgtagttcca    6180
gctactcggg aggctgggc aggagaatga catgaacccg ggaggcggag cttgcagtga     6240
gccgaagccg agatgctgcc actgcactcc agcctgggcg acagaacaaa accctgtctc    6300 tgaaaatat aataatgag ggaagaaggc aaacaatctc cctctgcctg ttttctaggc      6360
acacggtgac acccactcct ttacatgttg tctgtggttg cattcagtac atcagcggag    6420
taatggggca agagcacatg gcggcacagc agtggctcac gcctgtaatc ccagcacttt    6480
gggaggctga agtgggcgga tcacctgaga tgaggagttc gagaccagcc tgaccaacat    6540
ggtgaaaccc catctctact aaaaatacaa aaattagccg ggtgtggtgg gaggcacctg    6600
taatcccagc tacttgggaa gctgaggcag gagaatcacg tgaacccaag gtggaggttt    6660
gcagtgaggt gagatggtgc cactgcactc cagcctgggc gacagagcaa gactctatct    6720
```

-continued

```
caacaaataa aaaaaataat aataaagacc acatggcata aaatattgcc catctggcac    6780
tttgcgcagt ttgcccaccc ccagtctaaa ggcgtctgtc tcagcctgat gcgtctccca    6840
ggaccccatg cccccctccag cctgcagaca gcctccaacc gtgattccag aacctgccag   6900
catttcccac caactccttt tgccgggttt atttctcccc accactcctg gtctcactca    6960
accccccaac cctatggcca gacccgcccc cactctactg taaacacatt cggacctggc    7020
ctccctcccc agcctggggc agggctgtgg ctcaaggtac tgagtggatc taaggccgcc    7080
acacaagaca caagacacac gtggggaggg gctctctgta tcctttatct ccggcagggt    7140
cagcggccct ccagggcccg gtctcgagcg atgactgcct cctcgaactt gatcatgagc    7200
gtggtgccct tgtgccagtg cgccgtgacc ttggcaggga agccgctgtg tgtgagcacc    7260
gcctccacga tgcccgccgt gaagctggcg cagttgagcg tgctgttctc cttgggcacg    7320
gagatgtagg tgttgatgag cggctcgcgc tcgatgatgt agaaggtgcg cgcgtcatcg    7380
ttggcctgct ccagcttgtc cgcctccttg ccgaagagcg ccttccacac ggcgcccttg    7440
acgaagagca acgcgcctag caccttggtc tcacgccggg cacccttttc gcgcgccacc    7500
agcgcatcca gcacgcgcgc gcccacctgg cggcccagcg cggccaggcg cgactgcagc    7560
tcggccacgg agaagacgcg gctctggcag tgctgtacca gctcggagaa cagcagtgcg    7620
aaggcgctca ggctcacctc ggtgcgcggc gcgccagcg cgcgctccag cagcgccgac     7680
ttcccgcgcg tgaagcgcgc ctccatgccg ccgccaccct gcggggagac caggaagtgc    7740
aggtgtcagg ggcaatggga aggggagcag gccgggagga aggaggggag aaccgcgagg    7800
ggccctggga caccctcgac ccatgccact gttgtgtgct ccagtgccga cttcccactt    7860
gcaaagagat gcgcgtaaaa cacgcctcga ttacacgtaa ccagataaat caagggaggg    7920
gggagtctta taccctcggc aggcagcggg ctagcggag tggggacaag gtgggaggag     7980
agacacgagg gggaacagaa gaggaggccg aaaccaccca accctcgggc atgcagacgg    8040
ttcaattgcg aaagcgcctt cctgcccgct ccgccaccta caggagtaac tagaaaacta    8100
gtgtatgggg ggaggggcgt cagatctagg gcagggaggt gacaaagatg aggcaccacg    8160
aggggatatg ggcagtcgct cctgcccgc cctgcgctcc agcacagacg accctcggga     8220
actttcctgc cggcccctg cggaaagcca gagtaaaggg ggtggagggt gggagtgggg     8280
taggagcgtg tcaagaccaa aagccaggag ggttgggggc tttaacaggg gggatccgtg    8340
gggccaggca ggaggggcgg gtaacccca accccaagcc ctcaggcagg cagctccgat     8400
gtgtcacgca ggaacccttc gtcctttgag acgcggatgg gcctgggttc tgaaggctgg    8460
gaggaggggc ccagaggtgt tgggagcctc ccaccccgt gctctccaga aaggaagctg     8520
gatgctgagc aactgtggtc ctcccatcag ctgtcggtgc ggggagaggg agatggggta    8580
gggggctcct gaagagaaat ggggtgggga gcgggcgccg agacgggatc ggaggggcag    8640
ctgagaaccc gccccacca tgcatgggga ggtgtgtgga tgctaagccg accccaacga     8700
ggtctgcgtg ggaggtggga gaaccagcgg ggaggggtgt cccaggggct ccgggccgcc    8760
cccgccccag catgcagatc cgtccgtggc gagggccctg ggcgcgcgag atgggagagg    8820
gatcgttaag accccaccac cgggctgcga tggggctga agtgagctga actgccgtag     8880
ggtcagggcc ccgcgaccct cgccccgtac ctctacactg gggagaaacc caccctcctc    8940
gcagcctcct gagggggggcc gaagcgagcg ggctcgggat cgcggacgcc gagacccag    9000 cccgggaccc acacgcccgc ggggaagggg ccggggagcg gacgaggccc ggcgcgggca    9060 gggggggtggg tagggtctca ccaggaaccg cagcagtctg ctcggccgag ctgctttacg   9120
```

```
gcgccgtaaa aggcgctgcg tgcgcaggcg ctcgacgggc caggcgtgtg ggcggggcgc    9180
gcgcagcggt gcctgagagc ggccgcaggg gggcgcgcga gtccgcggag ccggacccag    9240
ggacgtggcc cacggccgtg atggctgctc cgcgcgtggc cagggtctcg ctggctctgg    9300
gtggcccacg ctgagggga cgcttgcagg cctagtcacc tgctcagggc gcacgtatga    9360
caatgggcca atgtataccc ttgcacatgg acacacctgt tggcttttcc aggcactcct    9420
atgtccttgg ggatgggttc aattgtctca agtgcatcca tgtggcccgc ggtggctccc    9480
gcctgtaacc ccagcatttt cggaggcgga ggtgggagaa tcacttgagg ccaggagttt    9540
gagaccagcc tggacaacat agctagactc ccacttcttt aaaaaaatt agccaggtgt    9600 ggtggtgtga acctgtaatc ccatctactc gggaggcgga ggcaagagga tcgcctgagc    9660
ccaggaggtc gaggctgcaa tgagtcatga tcgtaccact gccctccagc ctgggtgata    9720
gagcgagacc ctgtctcaaa aaacaaaaa caaacaacaa caacaacaaa tcaagtgcat    9780
gcatgagcgg tggacatagt accttagggt catgtacact catggataca tgctcaatgg    9840
catagataca ctcacgggca caattacaca cgtgggtaca cgcttagggc ttgtatatat    9900
ccgtggtccc aggtacactc agggagatgt tgtatgctca ggggcaccca ctctgggaca    9960
cagggaagac acagggaatg agttactcat tcacagatgc acaggtactc acgcagggca   10020
ctcagtctcg cccacccttgg tgccccgggg tcattgtcac gtgcagactc tccctctccc   10080
caggtcccaa aacccctccc cttgccccag taacaggtcc catagcgacg ctgtttccc    10140 ttgactttat ttatcttcat aagtcacaaa atgtgagtgc agagataaat gtctgtgtgc   10200
atgtgccctg agcacacagg gtggcataac tcggcacact cataatgaca cagccgttca   10260
cccagccaca gatagtgaca gggcacacat ggcgacaccc acatgtacgg agataaatct   10320
cccccaccat gacatgggta gacagaaaac acgccgcagt atactctagt atgtttacac   10380
aaacagggag acaggcccgt gcaatgcatg tcaccaacac ccacactcag agtgacatct   10440
gctggaggtg ctcagacaca gccacccacc gtgacatgcc gagactcaca tatgtcacat   10500
gacacaggca tgcatgccac attcactgtg actctcagtc ctattcattc atcacctttc   10560
tgggagatac actgaaatgt ccacccttg caaaatgcac acacacgcgc acgcacacac   10620
gcacatacac gaacacacgc gcacacacgc acacacacgc acgcaggtgt acacacacac   10680
gagcaactcc gagacactca ttcaccatga ctcgaggttt ttctatacgt gggacgaggg   10740
gcaggttcac actaggctgg ggggggggg tcatttcccg tcttcgttgg caggtgcagc   10800
cccatcttcc aagttgtggc tttggctgcc acaatgtcct ctcatttatt gaggtgagga   10860
ctctggggat gggagagac ccacagtgag gcagatcccg cccctgggag aggagctggg   10920
gctaaatctg aagccccacc caccctcctc cacctcctgt cggggcgcca acttacgtgg   10980
cattttctgc agcacctcca agattttctg tacctttgtg tcaatgtttt ttatgcctag   11040
ggggcgggga gggttgggtg ggaacagata agtcaagctg cggtggagcc tcaaacaaag   11100
ccccccactt ccttggaagc accccccctg ccccacaccc accctggggt acagcagagc   11160
ccatggattt ggggttccca ggagcctttc aatacccaca gagcaaccca gatggtaaca   11220
cccatcgccc ctccacaact tgagctttgg gagggtagga cccggctttc tcctcccct   11280 gaatccctg ccccagctc agctccggc attggtgaca aataaccccc atagaaggcg   11340
agactacaca ggcacctgct aatgtcgtct ctaatctatc aatcttgctc ctgaccatgg   11400
tgatgctctg ctgaacggaa tcccagcctc tcttctgtct ctcttcgcat gcttgtacgg   11460
agtttgagac tgagggcatg aaacaggggt gtctgtgcat ccatccctct ccagaccccc   11520
```

```
accatgaccc cacgggtctc cctcagaccc tccgctcacc attccaaagc tcccttttaa    11580
agcccagcag ctccttggac atctcagcat ctgttcagga ggggcaggaa aatccttgaa    11640
gcacccaggg agagagagag agaaggacaa gggagaaagt ctaggccccc cagcaccctc    11700
ctcccaagaa gtactcactc ttcaccatga tgaaggctga caggatgatg cagaggacaa    11760
aggccagggc caggaggatg tacaggctca ggatggctct gtacaaccag caggggacct    11820
gggtggagtc tgagggcggc ctgcactggg ctgggactgg agcaaagagg cagcaaagtg    11880
accttgaggg gccagcacca ccactcaaac catcctcact gtctctaaca ccatggacac    11940
ctcgctcctc tcaaaaccat cagcagctgt ggtcatgcag cttgtcatca tcgtcaacaa    12000
cactgccacc accagccacc ctcagcgatc taacaccgtc accatcacag accccctctc    12060
cagcattccc caacattgtc atcatcaaca gacctcatta gcacgtcaac agctgtcacc    12120
tcttccttcc ccatcgcttc ctcccttcca cgcagccccg ggggccctgc agttgcccgc    12180
ccacctgccc cttcccaagg tgatgggatg tgagcaggtg ggtgtctgct cacccttggct   12240
cgtgggtcgt gaatgaccac cctttgcatg gtcctgattt ttgaaggcca aggtgatatt    12300
ctcatagtct gggtcatggg cacctgggag gggttggaga tctgctcaga gctctgtggt    12360
gtggagagtg gatccgggat cttgttttac ccaaccctt gcactcaata aattgtaggg     12420
ggtgaaagat aaggagtgag aagctaaaat ctgcttttg gttaagtgga gcggtgtgt      12480
gagagtttga gtgatcacac cacacacaca tccacacaca catccacaca tcttggaggg    12540
gaaggagccc ccggcccca cctttgaccc cttacctctc ccatctgaac tctccttctt     12600
tttttatttt tattttttac agacagagtc tccctatgtt gcccaggcca gtctccacct    12660
ccagggctca cgcaatcctc ccgcctcagc ctcccaaagt gctaggatta cagacatgag    12720
caaaagcccc cggccccca atctctcctt cttaaccct cccttccacc tcgagttccc      12780
taaccttgat tcttggctga dccccctgt ttcttgtccc tgaaggctgg tgcttgcatc     12840
ttgacttcct ggtgcttgta gatttcctcc acttccatgg tccccagccc gcaaatttgt    12900
ccatacacgt ccccgcccac cggaaggtgt gggcagatga ggaaatctgg aggtgggggg    12960
aagaaagagg gggagcagcc tcctcttttc agggatccac gactctcgca ccctggggca    13020
ccctcattcc tgccccgatc aagaggctct tgggagccaa gaggtctcag gaaggaccaa    13080
gaagaaaaac ctctagaccg ggagatggaa ttcgacactc ggaaatgtta caggaagctg    13140
tggtctctgt gtgtgtctgt gtctacctgg atggacctca ccctcctacc tcctctccat    13200
ttcaaaagag aagctgtgac acctcagtgt cccaacttt cgcgtaagag caaccaggct     13260
tggagacagg accctgggt cccccacac cttcctccct ccagcctcag ctccacccct      13320
cagctccacc cccaagaagt tcttctactt ctacaagtcc ccgtggagga aaagcacaga    13380
tgtgaggcaa cgggaactaa ccactggaac gccacaccca catctgggac tgaggacaga    13440
cccacatcct tccctccctc cccaaatccc ctgcttttat acaaccctgg aggaggctgg    13500
gtgcggtggc tcacgcctgt aatcccagca ctctgggagg ctgaggtggg tggatcatct    13560
gaggtcagga gtttgaaacc agcctggcta acatggtgaa accccgtctc tactaaaaat    13620
acaaaaatta gctgggcgtg gtggcgagcg cctgtaatcc tagctactca ggaggctgag    13680
gcaggagaat cgcttaaacc tgggaggcgg aggctgcagt gagcggagat cacaccattg    13740
cactccagaa tgggtgacaa gagggaaact ctgtctcaaa aaagaaccct ggaggaacag    13800
tttcctctgc acctggaaac tccaggtttc tcattctcat ccatccatct gcttatctac    13860
ccagatactc tctctcacac atgtacacac acaggtctgc acacgacac acatcacaaa     13920
```

```
ctcatttgca tactatttgc attgtgacac tcagaaaaat agacacaagc atgcgttcac   13980
atgcccgcac tctgtctaga aggtgtctta gttcactttg tgtttatctg atcttgaaaa   14040
ctggggttac aaaaggcaca aagtagctgg gtatggtggc tcgctctgta gtcccagcta   14100
cccaggaggc tgaggtagga ggatcatttg aggccaggag tttgagacca gcgtgagcaa   14160
catagcaaga ccctgtctct ttaaatgttt tttaataatt ttttttttgag acagggtttc   14220 actctgttgc ccaggccggg gtgcagcagc gtgatcatgg ctcactgcag ctttgacctc   14280
cctggctcaa gtaatccttc gtcctcggct tcccgagtag ctgaaattac aggtgggcac   14340
gacttcacct ggctaatttt tctccttttt tgagatggag ttttgtgctt gtcacccagg   14400
ctggagtgca atgacgctat ctcagctcac tgcaacctcc gcatcccagg ttcaagtcat   14460
tctcctgcct cagcctccca gtagctggga ttacaggca tgcaccacca cccccggcta    14520
attttgtatt tttagtagag acggggtttc cccatgttgg tcaggctggt ctcgaactcc   14580
tgacttcacg tgatctaccc gccttggcct cccaaagtgc tgggattaca agcatcagcc   14640
accgtggccc agtctaattt tcttatttt ttgtagagat gagggtctca atatgccgtc    14700
caggctggtc ttgatctcct ggggttcaact gatcctccag ccttggtctc ccaaagtgct   14760
gggattacag gcatacattt ttatttttat ttttttctgg ccaggtgtgg tggctcacgc   14820
ctgtaatcac agcactttgg gagtctgagg cgggcggatc acctgaggtc aggagttaga   14880
gacaccagcc tgaccaatat gataaaaccc tgtctctact aaaaatgcaa aaattaactg   14940
ggcgtggtgg caggcgcctg taatctcagc cactcgggag gctgagacag gagaatcact   15000
tgaacccggg aggtggaggt tgcagtgagc cgagatcgcg ccattgcact ccagcctggg   15060
caacaagagc aaaactccgt caaaaaaaaa aaaaaaaaa gaaaaagaa gaaagaagaa     15120 agaaggaagg aaggaagaag aaaagaagaa aaaacaagta taagactgtc ttatgtgcag   15180
aaagtgatga tgttttggtt aaaaatatgt ggttaaattt cagacaactt gaatgttgag   15240
aaatgagcgt cgagatctgg tgaggataaa gttctgtttc ctaaaatatt gccaaatcct   15300
gtgtctccaa gaaagatcaa tttgataatg acttcatgcc agctgctcca tttggtctta   15360
gaaagaagtc agttactgag ctataggacc gccttctaat ggagcagacg gaccaattgg   15420
atgtgggctc tgccttgatg gacaggcaca gggggtggag ccacagcgtt gcacatttcc   15480
cgggcttggg tggggctgag acgcggctcc aggctctgga cttcctttga gaaaaaggtc   15540
acgctaaacc agaggcccac aagcaatcat gtcatgtggg aaacatctgc aaagctgcct   15600
gaccagcacc cgtcccttc atagggtaac attctcaatt ttcttttaag aaagaaaatg    15660
tgtgctagat ccagcaaacc ataagctagg gattggttta cagtggacaa atgatccaga   15720
cccagccaac cagagtctaa gattgggcag agaggcgggc atttgagcaa gatccagcca   15780
atgaaacgct ggtctgggat ttttattggt ttaaccacgg gggaaaaagc attctctttt   15840
ttttccagcc ctcactaggg ctgccacaat gggaggatgt aatgggagct gtgacaggga   15900
agaatttact tgagagcaaa ggcagtgctg agaaaatcag acccgagagg aagtctgggt   15960
cctggagaca tcatttgaga ccctggttcc aagccatacc tgaacctgtt gttctaaccc   16020
tgggcttgtc agttacacaa acaagaaact tcctttagt tttgcccaag ctagtttgaa     16080
gtggggtctg ttgtacttgc aagcagaaga atcttgcctt ggctggtctc tgtggcccac   16140
gcctgtaatc ccagcacttt ggaaggccga ggcaggtgaa tcacttaagg tcaggaattt   16200
gagaccagcc tggccaaaat ggcgaaatcc ccgtgtctac taaaaataca aaaattagcc   16260
aggagtggtg gtgggcgcct gcaatcccaa ctactcagga ggctgaagca ggagaatcac   16320
```

```
ttgaacctgg aggtggaggt tgcagtgagc tgagatcgtg ccactgcact ccagcctgga    16380
caacagagtg agactccatc tcaaaaagga agaagaagaa ggaggaggag gagaaggatg    16440
aggaggagga aggagggagt gaggagggag gagggaggag gatatcttgc ctaccacagg    16500
ggatctaggc attagctatt gaggaaattg aggctctaat aggggttttg cctgtccaca    16560
tcacctgggc agatatgacc tccaagtctg cactctgggg caggagaatg tctatgttgg    16620
aattgaggaa cctgaagaga gccctcttag gtttcagata caggactatt ggatgggggt    16680
ggagacaaat agttctgggg acaatggagc atccccgccc ccaacacaca cacacagcag    16740
taaggggcag ggacacacac aaggcactag actcaccctc tctggccctg gccatgcttc    16800
taactcagtg gtcctgccct accccatga ccactgtgga gtcaggagag agggtctggg    16860
aagggaatcc ctgggctgga gtctgggtgg ggtccctggc accagaagtg gttgtaatct    16920
ctgctcatgg ccaccagcat cagacagggg gctgggacca tcacagggggg tgggtggcag    16980 tgggaggaga gtccaaaaca tcctgcaaac cagaacctca ctctatcatc tgttgtccag    17040
gtgtgacatt tgagtctggg atccctttca agactaggtg ctaggaattc tgaagtctgt    17100
ggtgggaaat cagggactgg atggcaagac tcctgggtca ggcttcctgt agaactggac    17160
cccgaatcac ctgaatttgt gccccaggga gctgaggcgg gggatgctga ggcttttgcc    17220
cactagaaca ggggtcccca gccaccgggc attgggaacg gggcctcaca gcaggaggtg    17280
agtggtgggc gagcgagaga agcttcatct gtatttacag ccactcccca tcattcgcat    17340
taccacctga gctccacctc ctgtcagacc agcagcagca ttagattctc ataggagcaa    17400
gaatcccatc gtgaactgcg catttgaggg atgtagcttt ctcacttctt ataagaatca    17460
aatgcctggt aatctgtcgc tgtctcccat caccctcagc tgggaccatc tagttgcagg    17520
aacacaagct cagggctccc accgattcca cattatggtg agttgtagaa ttatttatt    17580 ctatattaca atgtcataat aataaaaata aagtgaataa taaatgtaat gcgcttgaat    17640
cacccagaaa ccatccccgc tccccccta ccccatacac acaccaactg tcttccatga    17700
aaacagtctc tggtgccaaa aaggttgggg atcgctgcac tagggtatca gatacttatc    17760
caggtgcagt ggggactaga gtcagaaatg caagagtctg cctggagcat gtgtgtgttt    17820
gtgtcctgca tcatctctgc ccaccatagt caaatctgcg attctccgtg cattggccgg    17880
gggggtggtg cctttctgtg tccaagagtg tctaggggca catgggtgtg tctgtggatg    17940
tggtgtctcc atgtggccgt ggtaggtggg ttgtgtactc tgtgtgtgca cgtggctgtg    18000
tatagctgtg tgtgcatgtg cagtatgtgc acgtcggtgc tgtatctaag tgcacatgtg    18060
gctactgatc aacagacatt tactgaacgt ctactgtgtt ccatgctcta ttctaaaccc    18120
tgggggcgct gggtgcagtg gctcatgcct gtaatcccag cactttggaa ggccgaggtg    18180
ggtggatcac ctgaggtcag gagtttgaga ctagcctggc caacatggtg aaacccgctc    18240
tctactaaaa atacaaatta gctgggcatg gtggtgggca cctgtaatct cagctacttg    18300
agaggctaag gcaggaatat cacttgaacc caggaggcag aggttgcagt gagccgagat    18360
tgtgccactg cactccagcc tgggcgccag agtaagacct tgtctcgaaa ataaaaatta    18420
aaaaataggc caggcgcggt ggctcatgca tgtaatccca gcactttggg aggctgaggc    18480
gggtgaatcg cttgaggcca ggagctcaag accaacctag ccaacatggt gaaactcctt    18540
ctctactaaa aatacaaaaa ttagccaggt atggtggcga gcgcctgtag tcccagctac    18600
gtgggaggct gaggcaggag aatcgcttga acccaggagg cagaggttgc ggtgagccga    18660
gattgcacca ctgcactcca gcctgggcaa cagagcgaga ccctgtctca aaaaaaaaa    18720
```

```
aagaaagaaa gaaagaaaag agaagagggg agaggagggg aggggagggg aggggagggg       18780
aggggagggg aagggaaggg aagaaacgaa accctggggg ggatctagga gcagacaagt       18840
cccctgctct gtgttttcat aatctagtat ccaggaaggg gtaagcaccc tgcgtgtatc       18900
tggttgtaac taactactca caactgcact tgcctgtgtg aaaacgtgag cttgtgatga       18960
tgcgtgacgt caggtaggcg tccctgactc tccgtaaccc aactttgcct gtgccttggg       19020
gattcctcct tgcaggtagg aagtgagggg tacaggttcc agctctgggc tgagacatga       19080
ttcagggttc caccctgacc tggggctcct ggagtcttgg ggcctggag ggtcccgtcc        19140
actgcccaga ctgacccagg tcctcgatga agcctcatta tgaggactgg gggaaaagga      19200
cccagccact tcctggggag gtcggagacc ccagggtgag cgtcaaggta gcctcaaaga      19260
tgagacgtca cctcttgaag gcagccatga gccttgggtg gggacgtcac tagaggaagt     19320
tcaggcccta ttttcggagg aagcagttgg agaccccata ggaggaaggg cgatggggca      19380
gtagaaagtc gcggtgtccc cgccccctcc agcagctacg cgccccactc tcttggagac     19440
gctagatcag tccctccggg cctactaaag aaaccacgca gggctcagat ccgctccatc      19500
atcatcatca tcatcatcat catcatctcc aggtttattt ccagctcccc cgcaacccct     19560
ccggacctgg agccgcctcc gcccgcgctg tgcacgcgct gcgcgcgacc tcagggctgc    19620
acacgacagc agcgcgctcc ggtccagtcc atgcccgcgc actggcagtg acatgtggtc    19680
tcggcgcgca catcccacga gccacaggcg gagccacaag tgcagccggt gacggcgaag    19740
cctgcagccc ggaacacagg agcgtggact ctgagctggg aggctgaggg tgggagcggg    19800
aggggggtgg ggagcgcgga gggggggttgg ggggcgggg gtggggacgg ggacggctgg   19860
aggctccaac cactgaatgg gcactggagg caggagtga gggtggacac cagtgtccag    19920
atggtgggcg gagaaggctg ggagtcagga ccaagatcct aggggagtag aggctggaca    19980
cggggaacgt ggcggggagg gggcattccc aggggacttg gaacagaaat gggcgcctgg    20040
acaacagtct cctgcactca cctcggggc aagtagccag gtcccccctg gaggtgacgc    20100
tctggcactc caggccaatg ctgcttattg ccctaaatac tgggggcag gaggaaagga    20160
gacaggggga gctgtgagac caaacggtcc ctcccccatc ctcccctagc cctgttggtt     20220
tggagctagg tccctgtggg cataggagct cactggcctc caggaccctg tcttgagttg    20280
ggtgttttgg agtaagggaa ggtttggagt gagagcgggg attgggtttg gagccgtgga    20340
taaggtgggg acagtcggag gggttgggag tggagttggg gttgaattta tgatctggtt    20400
ggatttgagg atgagatttg gtgagcgctg ggctgggtt ggagtcaggt ctgtgccagg     20460
gatcagtgag gtctctgaga ccctggggga gcttgcccaa gtggggggtc ctcacttagg    20520
gagccggcga cctcctggat cctctcattg atggcttctt ccatgagca cagggtcttg     20580
ctagacacca acagcccag gacagggagg aggaggagac agagagcttt catcctgcag     20640
gcgctgaaag agggaaccaa gagacccaca gctggatcag ccctgccctg tggggaagat    20700
ccggcccatg gagggagtag gatctgcccc tggacctgga cccctgtccc ccatgtgggg    20760
ggacagggat ggaggctcag ccttgacccc agcctcccg ctggtgccat ggcaagcgca     20820
ggagcagctg tcacttaccc tctcggtggg ctcagctaac caaatccggc acacgaattc    20880
ctgcaccgca gctcttttctt tgaggcctct tggggtgggg cttcctggct tggctaataa   20940
gtccctgggc ccccaaccct ccggtcccac atccggggcc aagaggaagc ccctgagcag    21000
acagtaaggg ctgaggagg aagggagcct tcccacttcc aacagggcct ccgtcttcat     21060
gtccagagac tggtcaggag gtggtgcccc agggataatg ccaggggctg tggtctgagg    21120
```

```
aacaggtaga caagcagagt tttgcatgca agggtggctg atgcaaacat gacaaaatta    21180
atgcctcttg ctaggcatgg tgcggacaag cacttgtagt cccagctact aaggaggctg    21240
acgtgagaga attgcttgag cccgggagtt cgaagctaca gtgacttatg atcacagcac    21300
tgcactccag tctgggcaac agagcaagac cacttctcta aaatagtaat aataattatg    21360
tctctgggtg agaatgacat accacattca tacccaaatg cccatgagca atagaactgg    21420
taaataaaat catggtttat ggccggtggc tcacgcctgt aatcccagca ctttgggagg    21480
ccaaggcggg cggatcactt gaggtcagga gcttgagacc aacctggcca acatgatgaa    21540
accctgtctc cattagacat acaaaaatta actgggcgtg gtggcgtgtg cctgtaatcc    21600
cagctacttg ggaggctgag gtgggagaat cacttgaacc cgggatgtgg aggttgcagt    21660
gcactgagat cgtgcccctg cactccatcc tggatgacta gcttgggcac catagcaaga    21720
ctccatctca aaagaagaa agaaaaatca tggtttattc catcaatggc atcacctgca    21780
acagaagttg gaaagccatt gctcatgggc caagtccagc tcatgtttct tcttggacca    21840
cccatgagct tggaatggtt attacatttt tatttgttct ttgtttccag tacaacgggc    21900
cttttgtggt aaaatacata taacatacaa cttaccatta taacttactt ttttcttttt    21960
tgagacggaa tcttgctctg tcgcccaggc tggagtgcag tggcgcgatc tcggctcact    22020
acaagctccg cctcctgggt tcacgccatt ctcctgcttc agcctcccaa gtagctggga    22080
ctacaggcgc ctgccaccac gcccagctaa tttttttgtat tttttttttt ttagtagaga    22140
tggagtttca ccgtgttagc caggatggtc tcgatcccct gaccttgtga tctgcccgcc    22200
ttggcctccc aaagtgctgg gattacaggc gtgaaccacc gtgcccggcc tttttttttt    22260
tttttttgag acggggtctt gctatgttgc ccaagctagt gtcagactcc tggcttcaag    22320
taatcctccc accttggact ccccagtagc tgaagctaca ggtatgcacc atcttgttcc    22380
attttaacca ttgcttttgt ttgtttcttt gtttcagagt ctcactcagt tgctcaggct    22440
ggagtacagt ggctcaatct tggctcactg caacctccac ctcctgggtt caagcaattc    22500
tcctgcctca gcctcccgag tagctgggat tacaggcgtg caccaccatg cccggctaat    22560 ttttttgtatt tttagtagag atggggtttc accatgttgg ccaggctggt ctcaaattcc    22620
tgacctcaag tgatccaccc gcctcagcct cccaaagtgc cgggattaca ggtgtgagcc    22680
accatgccca gcctattta accattttc agagcacaat tctgtggcaa taagcacatt    22740
catgttgtta tgtagccacc actgccgtcc atctccagaa ctttctcctc tttccaaact    22800
gaaactctgt ccccatgaaa cactcactcc ctatccctct ccccagcccc tggcaccctc    22860
catcttgctt tctgcctcta tggatctgat gactctaggg acctcctagg agtggaatca    22920
cacagtgttt gtccttttgt atctgcttat ttcactgagc ataatatccc caaggttcat    22980
ccctgctgta gcctgagtca gaactgtttt cctttccatg gctgtatcac attcccttgt    23040
gtggatgaac cacgttgtgt ttattccttc atccatcgat ggacacttgg gttgcttcca    23100
gcttttgttt tgttttttg tttgtttgtt tgttttttgtt agttcacgtc ttttgtgggt    23160
tttctttctt ttttgagatg gagtctcact ctgttgccct ggctggagtg cagtggcacg    23220
atctcggctc actgcaagct ccgcctcccg ggttcactcc attctcctgc ctcagcctcc    23280
cgagtagctg ggactatagg cgcccgccac catgcccagc taatttttttt gtattttag    23340 tagagacggg gtttcaccat gttagccagg atggtctcga tctcctgacc ttgtgatccg    23400
cccgtctcgg cctcccaaag tgctgggatt acaggtgtaa gccactgcgc ctggccgtct    23460
tttgttaatt catacagtta tttgtcttct ggtttgttga agcagtaagt cagacaacat    23520
```

```
ttgccacaat aatgtctgtc aaagtggctt gccataaaca ctgcagcacc acattcatca    23580
gaagggcaac ctcgacgaag gtgactaatt ttgccattct catccacctt ataatatttc    23640
aggacagcca gcttcacctt ctttctcttg tgcttattcg tcttgcaggt aagacttctt    23700
cttctggccg ggctcagtgg ctcaggcctg taatcccagc actttgggag gccgaggcag    23760
gtggatcacg aggtcaggag ttcaagacca gcctggccaa catggtgaaa ccctgtctct    23820
actaaaaata caaaaattag ctgggcgtgg tggcacgtgc ctgtaatccc agctactcgg    23880
gaggctgagg caggagaatt gcttgaactg ggacccggga ggcagaggtt gcagtgagcc    23940
gagattgcac cactgcactc cagcctgagc tacagagcga gactccatct caaaaaaaat    24000
aaaaaaaaga cttcttcctt tccttagcac caccacgaat tctcaataca agatgaagag    24060
gagactcctt ttgaatgttg tagtcagaca gagtacgccc atcttccagt gcttgtcttt    24120
gctgatcagg aggaattctt tctttaccct ggatcttggc cttatacattt tctaccatat   24180
ctgagggttc agcctcgagg gtggtggtct tccctgtaag ggttttcagg aaaatctaca    24240
ttttggtggc ggctccacca cagatggcgg atctaaaagg ttttgtttt ttgtttttttt    24300
gagacagagt ttcgctcttg tcacccaggc tggagtgcaa gtggcacgat cttggctcac    24360
tgcaacctct gactcctggg tttaagtgat tatcctgcct cggcctccga gtagccagga    24420
ttacaggcat gtgccaccac cacacctggc taattttttt ttcttttgta ttttttagtag   24480
agatggggtt ttgccatgtt ggccaggctg gtctcaaact cctgatctgg agtgatccgc    24540
ctgcctcggc ctcccaaagt cctgggatta caggtgtgag ccactgtgcc tggcctgctt    24600
ctgccttttg gctattgtga ataatgctgc tctgaacata gatgtgcaaa tatctgtttg    24660
cagctcctgc tttcaattct tctgggcgta tgtccaggag tagtgctgcc tgatcatatg    24720
gtaattctat gtttaacttt ttgaggcact gccaattttc acattttaa accataggga    24780
aaaaaaagtt gttttttttt taaaaagac acagtctggc tctgttttcc acgctggagt    24840
gcaatggtgc aatcatagct cactgcagcc tcaaactcct gggctcaagc aatcccccc    24900
tcatcagcct cttgagtagg tgggactacg gcatgtgtca ccacacctaa ctaattttt    24960
taatttttt gtagaggtgg ggtctcactc tattgcccag gctggtctca aactcctggc    25020
ctcaaaagat cctgccacct tagcttccca aagcactgag attacaggca tgagccactg    25080
tgcctagcca aaaatattt gtaatgttta gtgaaaatag aaatcatata aaattcaaat    25140
tcatataatt ttcataaaaa gtccataaag aaaattttct taaaacattg tcagctgggt    25200
gcggtggctc atgcctgtaa tcacagcact ttgggaggct aaggcgggtg gatcacctga    25260
ggtcaggagt tcaagaccag cctggccaat gtggtgaaac cccatcacta cttacaatac    25320
aaaattagcc gggtgtggtg gcacgcgact gtaatcccag ctacttgaga ggccgaggca    25380
ggagaattgc ttgaacccgg gaggtggagg ttgcagtgag tcaagatggt gcccttgcac    25440
tccagcctgg gcaacaagag cgaaactctg tctcaaaaaa aaaaaaaatt gccaagctca    25500
gtggcaggca cctgtcatcc tagctacttg agagaccaaa gcaggaggat tgtttgagcc    25560
caggagtttg agggcagcct gagcaacata gtgagatcct gtccctacaa acacacacac    25620
acagtttgct accccctttt ttttgagagg gagactcgct cttgtcaccc aggctggagt    25680
gcagtggcac gaccttggct caccgcaacc tctgcctccc gggttaaagc gattctcctg    25740
cctcagcctc ccgagtagct gggattatag gcaggtgcgc caccatgtcc ggctaatttt    25800
tgtattttta gtagagatgg gatttcgcca tgttagccag gctggcttcg atctcctgat    25860
ctcaagtgat ccgcccgcct tggcctccca gagtgctgag actataggca tgagccactg    25920
```

```
cacctggccc catttttttaa tatatcatca gtgactgcta tcacatgtcc atggcagagc    25980
tcagcagctg tagagtggtt ggacagtagg gcccccaaag ctgagaatgt ttactatctg    26040
actcgttaca gaaaacattt ttttgtaccc ctggtatgtg gtgatgagtg agaatgagac    26100
aactgtccat ggattacagc tacacccaac catgtggctg attctcacga acatatgtta    26160
gcatagaagc cagaccccaa aagaacata  ccatacaaat ccatttatta aaaaaaagg     26220 gggccgggcg cggtggctcc tgcctgtaat cccagcactt tgggaggcca aggcaggcgg    26280
atcacaaggt caggagatca agaccatcct ggctaacacg gtgaaacccc atctctacta    26340
aaaatccaaa aaaattagcc gggcgtggtg gcaggcacct gcagtcccag ctcctcggga    26400
ggctgaggca ggagaacggt gtgaacccgg gaggcggagc ttgcagtgag ccgagatggc    26460
gccactgcac tccagcctgg gcgacagagc aagactccgt ctcaaaaaaa aaaaaaaata    26520
cctaaaaata caaaaattag ccaggtgtag cggcaggtgc ctgtaatccc agctactcgg    26580
gatgctgagg gaggagaatc gcttgaacca agaggtggag gttgcagtga gctgaaatca    26640
tgctactgca ctccagcctg gcaacagag  agagactccg tctcacaata atgataataa    26700
taataaatga aatacaaaca aaactaatt  atgctgtcgg aaatgacgat ggaagagtcc    26760
tggggaatca gagatagtgg tgataaaagc ataccaggaa ggcccctagt gagggggggaa   26820 ttttgtaaaa gttttcagct gtaactctca tttgcacaat tttctctatg tatttatatt    26880
tcaatcaaca tgatgcatgt gtattaaagc cctgtgtaaa tgcaacggtg cacacaggtt    26940
caaagcgcag gcaatattta ttgagcaact attatgttcc atatgctgtg ttaaacacca    27000
tgcatacact aagaagcaga gggatgctgc ccttgcccgg gacgagttgg cccttgtcag    27060
tcagggaaag gcagacacca acagaacagc aataaaaagg ccgggcaatg gccaggcgc     27120 ggtggctcat gcttgtaatc ccagcctttt gggaggccga ggcgggtgga tcacctgagg    27180
tcgggagttc gagaccagcg tgaccaacat ggagaaaccc cttttctact aaaaacacaa    27240
aattagccag gcgtggtggc acaccaggtg ggtagctgta atcctagtta ctcgggaggc    27300
tgaggcagga gaattgcttg aacccgggag gcggaggttg tggtgagcca aggttgtgcc    27360
attgctttcc agcctgggca acaaaagca  aaactccatc tcaaaaaaaa aaaaaaaagt    27420
ccgggcgcca tggctcacac ctgtaatccc agtgctttag agaccgagg  tgggtggatc    27480 acttgagccc aggagttcaa gaccagcctg gccaacacag tgagaccctc cctctgtaca    27540
aaacgtaaga aaacattagg cagggatggt ggtggcttcc tgtagtccca gctactcagg    27600
aggctgagac agaagtaccg cttgagtcca ggagttggag actgcagtga gctatgatcg    27660
caccactgca ctccagcctg gacaacagag caagaccca  tctctaaaaa aagaaaaca    27720 aaaaacaac  aacaaaaaac accaatagaa tgctcaatca gccatcagcc tcaaggaccc    27780
ttccatctcc caaggagagg aaccctttc  cgtgagaacc tctgacctaa aaatcaaccc    27840
cacatgggga aatccagaaa gtattttggg gggaggaaaa gatgtttgaa gggagggtgg    27900
aggatgcaga agggttaacc aggagaggca gttagggagg gccttctggg tggagggaga    27960
ggactgcatt tccaaggac  ctgaggcaga atggagtgtg tgtatttaga ggaactgaaa    28020
gcaaatttgt gggacagggg atctagaggg gaaaagtgaa ttccacaggc tccctgtctc    28080
ttctggtcct agcaggaact ttcaagtccg tttttgtcca gatatttccc catgctcaag    28140
tcccagctca tcctgcctcc ttgaagacat gacttctgtc tcttcttgag ctactctttg    28200
acacaccctg gacaaagggt agcttgaaaa gagacagaaa ccatgttatt gccaggtgca    28260
gtggctcacg cctgtcatcc ttgtgctttg ggaggctgag gcaggaggat cgcttgaggc    28320
```

```
caggagcttg agaccagcct ggacaacata acaagacccc atctctacaa agataaaagg    28380 gaaaagccg  ggcgcagtgg ttcacgcctg taatcccagc actttgggag gccaaggtgg    28440
gcagatcacc tgaggtcagg agttcgagac cagcctggcc aacatggcga acccccgtct    28500
ctactaaaaa tacaaaaatt agatgggcgt ggtggcgggc acctgtaatc ccagctactc    28560
gggaggctga ggcaggaaaa tcacttgaac ccaggaggtg gaggttgcag tgagctgaga    28620
ttgcaccact gcactccagc ctgggcgaca gagtgagcct ggtctcaat  caatcaatca    28680 atcaatcaat ggaaaaaaat tagctgggtg tggtggtcca tgctggtagt cccagctact    28740
gaggaggctg gggtgtgagg atcacttgag cccaggaagg ctgagactgc aatgagctat    28800
gatggcatca ctgcactcca gcctggacaa caaagcaaga tcccgtctca aaaaaaaga    28860 agaaaagaa  aaatcatttt ttgagagctc tgattttcaa acctttgtt  ctcagaactc    28920 ttcgggtaaa acctttgaa  cgacacaaaa ggagtgggca gctgtgatga cagattgagg    28980
agaaagcagg gtaggcatgg aacctctagg gttccctagg gacccagttt gaaaactctt    29040
ggttcagtag caggaaaagg caatatgccc cttaattctc ttctaaaaca taaaatcctt    29100
taacttcctc tgatttctac cagtaaaact gagctctact gacctcaatt ttgtaccaaa    29160
tgctatctaa taaaatccca gaaacagtga tttttgaaaa atccattttg ttgatgtgta    29220
atttacatac agtagaatgt gcctatctta tgtgtttggt ttcatgcatt gttttctttt    29280
ttcaactttt taaatttttt ttttttttg  agacagggtc tcactctgtt gcccaggttg    29340
gcgtgcagtg gcacaatctc ggctcactgc aaccttcgcc tctcgggttc aagcaattct    29400
cctgcctcag cctcctgagt aggtgggacc acaggcacgc gccactacac ccagctaatt    29460
tttgtatttt tagtagagac agggtttctc catgttggcc aggttggtct cgaactcttg    29520
acctcaagtg atccacccac ttcggcctcc caaagtgctg ggaccacagg cacacaccac    29580
cacgcccaac taattttgt  atttttcata gagatggggt ttcaccatgt tgcccaggct    29640
ggtctcaaac tcctggcctc aagtgatctg cctgccttgg cctcccaaag tgctggaatt    29700
acaggcataa gccaccatgg ccagccctct ttatcaactt ttatttattt tttcattttt    29760
ttgagacgga gtctcgctct gttgcccaaa ctggagtgca gcggtgcgac tcagctcac    29820 tgcaacctcc gcctcccggg ttcaagcgat tctcctgcat cagcctccca gtagctggg    29880 attacaggtg cccgccacca cgcccatcta attttgtat  ttttagtgga gacggggttt    29940
caccatgttg cccaggctgg tctcgaactc ctggcctcaa agcgacctgc ccgccttggc    30000
ctcccaaagt gctgggatta cagttgtgag ccgccgcgcc cgggaccctc tttatcaact    30060
tttattttag attcagggga tacctgtgcc agtctcctac ctgagtatat tgcatgatgc    30120
tgaggtttgg ggtatgagcg actctgtcac ccagatggtg agcacagcac tcaacagtta    30180
gattttcaac cctcatgccc ctttcctca  cccctccctg gcaatcccca ctgttcatta    30240
ttgccacctt tatgtccatg agtacctgaa gtttagatcc cacttataag tgagaacagg    30300
cagtctttgg tctgctgtta ctgagtttga tgcattttga caaatgtgtc tacctgcctg    30360
ctgcacgttt tggttttccc aagaattatt ttctaaaaat cagttttat  taaggtggca    30420 tttatataca ctaaaattct gcacacgatc ttgtaaccat caccaccaaa tacgtattta    30480
tttatttatt attattttt  agagatgcg  tctcactctg tctcgatctc ccacgccggg    30540
gtgcagtggt gccatcagag ctcactgcat cctccaactc ctgggctcaa gcgatcctcc    30600
tgcctcagcc tcctgagtag ctaggactac aggcacccac caccacccac agttaattga    30660
aaaaattgat tcttctttgt agagacaggg tctcatatgt tgccaggatc cttggtcttt    30720
```

```
gacctcccaa agtgcagaga ttacaggcat gcaccactaa tgccgggcca aatacttgta    30780
atttaaatta tcgctgggct gggcacggtg gctcacgcct gtaacccagc actttgggag    30840
gccgaggggg gaagttcacc tgaggtcagg agttccagac cagcctggcc aacatgctga    30900
aaccctgtct caactaaaaa tacaaaaatc agccggacat tgtggcagac gcctgtaatc    30960
ccagctaatc gggaggctaa gacaggagaa tcgcttgaac ccgggaggca gaggttgcag    31020
tgagccgaga tcgcaccatt gtgctccaac ctgggcaaca gagcgaaac tccatctcaa     31080 aaaataataa taaatataat tatagttgga aaaaggggt ttcctaaaga cccaagggaa     31140
atggcctctt tgttcctgaa gccacagaga ggattttct gctccccaca actagttttc      31200
cttgtgaaaa ttcataattg ctaccagctt gttctcctct ctgtcactat acatctgtcc    31260
ttgaagcctt atttgaacaa agagttctgg tatcactcgg atgcctagaa actgttgccg    31320
ttctgtgaaa ccgaccacca gaggaaaccc atgcttctca ttggctgcct tactaagatg    31380
gtgacttgtt gccctggtga caagttgcaa tgacaggtgg ctctgccaaa tcagaacaca    31440
gtgatacttg cttccctcc cgggtgaagg atggaaaata aaagtaaaag ccttggcggc      31500
tgtcaggctt ctttaccaaa gagctggaga gcactccttg gccccattta tgcaaacact    31560
tcccatctac agatgatcca gcttcggagt gggagtctaa gcagctgcca ggaccaccgc    31620
ttggcagagg acaggctggg ggctctggca tgacctgctg gggccaggct gtgacttgga    31680
gcaagaggta gcaagaacct cgaggcagtg aacatcaaaa gagagatttc cggggctaaa    31740
cacccctagg ttttccttcc tcctgaaccc taacccctaac cctctcggct cactgcaacc    31800
tccacctccc gagtgcaagc aattctcatg cctcagcctc ccgagtagct gggatcacag    31860
gcgtgcgcca ccacgcccgg ctaactttgt atttttatta gagacggggg tttctccacg    31920
ttggtcaggc tggtgtcaaa ctctcgaact caggtgatct gcccgccttg gcctccaaaa    31980
gtgctgggat tacaggcgtg cgccaccgtg cccagcttat ttttgtattt ttagtagagg    32040
tggggtttca ccctgttggc caggctggtc ttgaactcct gaactcaagt gatctgcctg    32100
cctcagcctg ccaaaatgct ggggttacag gcgccaggcc aagtatctta tttttaaagg    32160
ttacaaagaa tatagatgtg gataaaataa aagtttcttt gcattaccac tttcctgcaa    32220
gaaatgaggg ggaggggctt atgaaacaac tcacacccccc ccaattgagg aactgtagat    32280
gaaagggaag gtgctgacag gcccgtctgg ccacggtttc ctggaataaa actgagccac    32340
acacctccac aaatccccag cctccggcaa gtaccccaga agtactcaca ctccaccacc    32400
ttctgtgatc gcaacagccc tacgcaacat tacagagggc aaaacccacg ctggggaagg    32460
cggggctact gtcaaaaggt caccagggcc aggcacagtg gctcacgcct ataatcccag    32520
ctccttggga gaccaaggca ggaggatccg ttgagctcaa gagtttgagt tcagcctggg    32580
caacacagga aaaccccgt ctttacaaaa acttttttaaa aattagctgg gtgtggtggc      32640
atgcccgtgt aatcccagcc actcttagg aggccgaagg gggaggatct attgcttcag      32700
cccgggagtt tgtggctgca gtgagctatg attgcaccac tgcactccag cctaagtgac    32760
agacagagac tcttaaaaaa aaaaaaaaaa gggcagggca cggtggctta tgtctgtaat    32820
cctagcactt tgggaggccg aggcgggcag atcatctggc gtcaggagtt cgaggccaac    32880
ctggccaata tggtgaaacc ctgtctctac caaaagtaca aaacttagct gggtgtgatg    32940
gtgggcacct gtaatcccag ctactcggga ggctgaggtg ggagaatcgc ttgaatctgg    33000
gaggtggagt ttgcagtgag ccaagattgc gccactgcac tccagcctgg gtgacagaat    33060
gagactctgt ctcaaaaaaa aaaaaaaaaa gtggggcacc tatattccca gcactttggg    33120
```

```
aagctgaggc aggaggatgg cttgaggcca aaaattcaaa acccggcctg ggcaacatag   33180
caagacccca tctctatgaa aaaaaaaaaa aaaaagtcac caggccagct agcctagatt   33240
tcagagccag aatttgtctg atgccattgt ctttactttt tcttttttctt tttttttttt   33300 ttgagacaga gtctcactct gtcacccaag ctgcagggca gtgggacaat ctcagctcac   33360
tgcaacctct gcctcccagg ctcaagcgat tctcctgcct cagcctcctg agtagctggg   33420
attacagaca tccaccacca tttccagcta attttgtat ttttagtaga ggtgaggttt    33480 caccttttg gtcaggctgg tctccaactc ccaagctcag gtgatctgcc cacctcagcc    33540
tcccaaagtg ctgggattac agttgcgagc caccacgcct ggactgctct tcattctttt   33600
ttcagaactt tcccagctgc caacagagac agaaactgaa tcatctcaga agtgaatgaa   33660
ggaggctgag ggcgggtgga ctgcttgatt aggagttcga gatttgccta ggcaacatgg   33720
aaaaagcctg tctctgctaa aaatacaaaa attagccggg cgtggtggca catgcctgta   33780
atgccagctc ttgggaggc tgaggcagga gaatcacttg aacccgggag gcagaggctg     33840
cagcgagccg agatcgcgcc actgcactcc agcctaggta acagggcgag actccgcctc   33900
aaaaaaaaaa gaagggaatg aaggacaccc aaaatggagc ctctgtctgc cagggctttg   33960
ctatcctggc ctgcctatcc cagccctgga cacctcatct ctgatcccac cagagcggaa   34020
ccttcccatt cgcagggcca tttccttacc cagaaacctt ttcacaatgt tcttggcagc   34080
agctgttggt caactgtgtt ttaaggtttt tgagcaactt tacagaaaat aaaagggaag   34140
ctaccctcaa tgtctgggtc tcccctggg tggcctctct ttgtcacctt actcatttcc    34200
acgagatttc cttgcttcgt tgagttacat cacctccttt tcctgtctgg gtccaggacg   34260
cctcctctgc aggtctccag cactgattcc tttgtcccg atttctctgc tagggtcgct    34320
ggcttcacca tcccaccacc actgctgctg gcccagcccg cagctttaat ttctctggac   34380
cctcacgttt ttgttatttg tgttttttt ggagatgagg tcttgctctg tcacccaggc    34440
tggagtgcag tggtgcaatc acagctcact gtagcctcca cctcccagac tcaagtgatc   34500
ttcctgcctc agcctcccaa gtagctgggt gtgtgccacc aggtgcagct acatttttg    34560 tagaggcagg ggtcttgcta tattgcccag gctggtctca aactcccagc tttagatgat   34620
cctttcacct cggcctccca gagtgctggg attaccagca tgagccactg cacccgtcct   34680
ctcatgtatt ttttattaat cgatttatct atttacttat tttgagacag agtcttgctg   34740
taccacccag gctggagtgc agtggcatga tctcggccca ctgcaacctc cactccctgg   34800
gttcaagtga ttctcctgcc tcagcctccc gagtagctgg gattacaggt gcccgccacc   34860
atgcctggct aattttttgta tttttagtag tgacgaggtt tcaccgtgtt ggccaggctg   34920
gtctcgaatt cctgacctca ggtgatccac ccaactcggc ctcccaaagt gctgggatta   34980
caggcgtgag ccaccgcact cggcctccct catgtatttt taagcggaac aggttcaaga   35040
tcacaaatgt tttcctctca ctctttcaat gagtttctat tctagaatct cctgcacgcc   35100
acaggaagga gaactctcac cctgtaatgc acataaatac atgagatcac cattgttctc   35160
acccagtaat cagaatcgtt agtgataatt agtaataaat ttatttttac tatatctaat   35220
aaattagata gtaattacta tggcagccaa tcgttcctgg gtgctcccta gatgcttcca   35280
agggagccac acgtgaccct cagggctgtg cccattccag gctcttctgc tgagctcatg   35340
taaccgcttg cctcaaggca ttccacaaat aatacataag tcaatgtatc acgttgtcac   35400
tttctgtaca aaccagctag ttccggaggg aagcagaaag cctttttcag aagaaccaca   35460
gctaattcca gtagcaggaa tgataaagtt ggacataatc ctcaagagag taatgaatca   35520
```

```
aaaatggatg gcgggccagg cacggtggct gatgcctgta atcccagcac tttaggagga    35580
tgaggcaggt gaatcatttg aggtcaggag ttcaagacca gcttggccac catggtgaga    35640
ccccgtctct actaaaaata caaaaattag cctggcatgg tggctcatgc ttgtagtccc    35700
agcttcttgg gaggctgagg caggagaatt gattgaaccc tggaggtgga gattgcagtg    35760
agccaagatt gcatcactgc actccagcct gggcaacaag agcgaaactc tatctcaaaa    35820
acaaacaaac aaacaataac aacaacaaaa ttgatggctg ctaatgactt ttttctttt    35880 ctttccttt ttattttat tttttatgag acagggtctc actctatcgc ccaaactgga    35940
gtgcagtgcc gagatcataa ctcagtgcag cctcaacctc ttggactcaa gtgatcttcc    36000
cacctcagcc tcccatgtag ctgggactac aagcaattgc tgccacatct ggctaattat    36060
tttattttgt tgtattttat ttatttattt tttgagacag agtcttactc tgtcacccag    36120
gctggagtgc aatggcatga tctcagctca ctgcaacctc cgcctcctgg attcaagtta    36180
ttctcctacc tcagcttcct gagtagctgg gataacaggt gtgcaccacc acgcctggtt    36240 aattttggt tttttggtag agacgggtt tcatcatgtt ggccaggctg gtcttgaact    36300
cctgacctca gtgatccgc ccatctcagc ctcccaaagt gctgggatta caggtatgag    36360
ccaccgtgcc cggtctttat tttatttta gtagagacag ggttttgcta tgttgcccag    36420
gctggtctca aactcctggg cctaagtgat cctcctgcct tggcctccca aagtgctggg    36480
aactacaggc gtgagccact gggcccagct cctgttaaca tctttatgtg gagagttact    36540
ggggaccagg gacattcccc aaacccaccc atcaatcgta gtgacatgac gttatggacc    36600
ccctgatgtg atgtaccagg aagtacccgg ccctaccagc atgatattat tctggctgca    36660
actgaccctt attccaatag agcatgtggt tctaagccat ttatagggta aacattgggg    36720
cagggatggg gagagaggaa gcaacctgcc aaatccagaa tgaggatcat tcctcggtac    36780
cagaagagaa ccagaaagaa agcacccta gtggggatac cacaaggaag taaagcaggg    36840
gcctctccca gctggggaag ggaaggagga aggagtacaa tagcttgcaa ggcacagcat    36900
tgcggatgat gggaatagca ggtgcaaagg ttctggggca gggacagtgt ggtgtgtttg    36960
aagaacagca gccaggttca ccatgagatg ggaaatggac ttgggggaag ggatctcaaa    37020
ggataatttt tttttttt ttgagacagg gtttcgctct tgttgccag gctggagtgc    37080 agtggcatga tggctcactg caacctctgc cttccggttt caagcgattc tcctgcctca    37140
gcctcccgag tagctgggat tacaggcgcc caccaccacg cccggctaat ttttgtattt    37200
ttagtagaga caggggtttca ccatgttggc tagactggtc ttgaactcct gacctcgtga    37260
tccgcccgcc tcggcctccc aaagtgctgg gattacagac gtgagccacc gcgcccggcc    37320
ccccaacttt ttttttgttt ttaacacaac ttctcgcttt ctcacccagg ctggagggca    37380
gaggcacaat catagctcac tgcagcctcg aactcctagg ctccagcgat cctcacagga    37440
gggttttgag gatctgcata aagcgtgcag agggagcttg acttcgtgct cgttaggacc    37500
cgatattgtc agctgccgcc gcccacaggg acacataaat atttgtagac tcaatatttg    37560
cctttagtgt gaagacattg catcacctgg gtataagtaa ggagcagagg cagaggcggt    37620
ttaagcaaca gacttttgtc tccgctgaga accacggaat aaccctgac ctacttcccc    37680 gtcgtgtcta attcgggtca cctcatctcc agttacagac gcggaagatc aaagaaaccg    37740
ggaaattgcg ccgcagcgcc ccctggcgtt cgcagcgcgt gcctacacaa gccactcccg    37800
gcgcaaaact gcggcttccc aggaaattga gtttaaatgt tttttttct ttttcttaa    37860 tctagaaaag atcattatt gtatcaagta actacccagt taggcgtgaa tacattttaa    37920
```

```
aatttttatt aaaacgagta ttggccgggc gcggtggctc actcctgtaa tcccagcact    37980
ttgggaggcc aaggcaggtg gatcacggcg tcaggagttc gagaccatcc cggccaacat    38040
ggtgaaaccc cgtctctact aaaaatacaa aaattagctg gcgtggtgg cacgcacctg    38100 tagtcccagc tactcgggag gctgagacag aagaatcggt tgaaccgggg aggcggaggt    38160
tgcagtgagc tgagatcatg ccactgcact ccagcctggg cgacggagcg agactccatc    38220
tccaaaaaat aaataaataa ataaatataa tataatataa aataaaataa aaagagtatt    38280
gtagagattg gctgggcaca gtggctcaca cctctaattc ctgcattttg ggaggctgag    38340
gtgggaggtc ttcagcccag gagttagaga ccagcctggc caacatggca aaaccccatc    38400
tctactaaaa gtacaaaaat tcgctgggca tggtgtcgca cgtctgtgat cccagctttt    38460
tgggaggctg aggcaggaga atcgcttgaa cccaggaggc agaggttaca gtgaatcgag    38520
atcgcaccac tgcactccag cctgggcaac agagtgagac cttgtctcaa aaatacatat    38580
atttagg                                                              38587

<210> SEQ ID NO 4
<211> LENGTH: 30943
<212> TYPE: DNA
<213> ORGANISM: Homo sapiens

<400> SEQUENCE: 4
gggcgtggtg gcacatgcct gtaatgccag ctgcttggga ggctgaggca ggagaatcac      60
ttgaacccgg gaggcagagg ctgcagcgag ccgagatcgc gccactgcac tccagcctag     120
gtaacagggc gagactccgc ctcaaaaaaa aaagaaggga atgaaggaca cccaaaatgg     180
agcctctgtc tgccagggct ttgctatcct ggcctgccta tcccagccct ggacacctca     240
tctctgatcc caccagagcg gaaccttccc attcgcaggg ccatttcctt acccagaaac     300
cttttcacaa tgttcttggc agcagctgtt ggtcaactgt gttttaaggt ttttgagcaa     360
ctttacagaa aataaaaggg aagctaccct caatgtctgg gtctcccct gggtggcctc      420 tctttgtcac cttactcatt tccacgagat ttccttgctt cgttgagtta catcacctcc     480
ttttcctgtc tgggtccagg acgcctcctc tgcaggtctc cagcactgat tcctttgtcc     540
ccgatttctc tgctagggtc gctggcttca ccatcccacc accactgctg ctggcccagc     600
ccgcagcttt aatttctctg gaccctcacg ttttgttat ttgtgttttt tttgagatg       660 aggtcttgct ctgtcaccca ggctggagtg cagtggtgca atcacagctc actgtagcct     720
ccacctccca gactcaagtg atcttcctgc ctcagcctcc caagtagctg ggtgtgtgcc     780
accaggtgca gctacatttt ttgtagaggc aggggtcttg ctatattgcc caggctggtc     840
tcaaactccc agctttagat gatcctttca cctcggcctc ccagagtgct gggattacca     900
gcatgagcca ctgcacccgt cctctcatgt atttttatt aatcgattta tctatttact      960
tattttgaga cagagtcttg ctgtaccacc caggctggag tgcagtggca tgatctcggc    1020
ccactgcaac ctccactccc tgggttcaag tgattctcct gcctcagcct cccgagtagc    1080
tgggattaca ggtgcccgcc accatgcctg gctaattttt gtatttttag tagtgacgag    1140
gtttcaccgt gttggccagg ctggtctcga attcctgacc tcaggtgatc cacccaactc    1200
ggcctcccaa agtgctggga ttacaggcgt gagccaccgc actcggcctc cctcatgtat    1260
ttttaagcgg aacaggttca agatcacaaa tgttttcctc tcactctttc aatgagtttc    1320
tattctagaa tctcctgcac gccacaggaa ggagaactct cacccctgtaa tgcacataaa    1380 tacatgagat caccattgtt ctcacccagt aatcagaatc gttagtgata attagtaata    1440
```

-continued

```
aatttatttt tactatatct aataaattag atagtaatta ctatggcagc caatcgttcc    1500
tgggtgctcc ctagatgctt ccaagggagc cacacgtgac cctcagggct gtgcccattc    1560
caggctcttc tgctgagctc atgtaaccgc ttgcctcaag gcattccaca aataatacat    1620
aagtcaatgt atcacgttgt cactttctgt acaaaccagc tagttccgga gggaagcaga    1680
aagccttttt cagaagaacc acagctaatt ccagtagcag gaatgataaa gttggacata    1740
atcctcaaga gagtaatgaa tcaaaaatgg atggcgggcc aggcacggtg gctgatgcct    1800
gtaatcccag cactttagga ggatgaggca ggtgaatcat ttgaggtcag gagttcaaga    1860
ccagcttggc caccatggtg agaccccgtc tctactaaaa atacaaaaat tagcctggca    1920
tggtggctca tgcttgtagt cccagcttct gggaggctg aggcaggaga attgattgaa     1980
ccctggaggt ggagattgca gtgagccaag attgcatcac tgcactccag cctgggcaac    2040
aagagcgaaa ctctatctca aaaacaaaca aacaaacaat aacaacaaca aaattgatgg    2100
ctgctaatga ctttttttct tttctttcct tttttatttt tatttttat gagacagggt     2160 ctcactctat cgcccaaact ggagtgcagt gccgagatca taactcagtg cagcctcaac    2220
ctcttggact caagtgatct tcccacctca gcctcccatg tagctgggac tacaagcaat    2280
tgctgccaca tctggctaat tatttattt tgttgtattt tatttattta ttttttgaga     2340
cagagtctta ctctgtcacc caggctggag tgcaatggca tgatctcagc tcactgcaac    2400
ctccgcctcc tggattcaag ttattctcct acctcagctt cctgagtagc tgggataaca    2460
ggtgtgcacc accacgcctg gttaattttt ggttttttgg tagagacggg gtttcatcat    2520
gttggccagg ctggtcttga actcctgacc tcaagtgatc cgcccatctc agcctcccaa    2580
agtgctggga ttacaggtat gagccaccgt gcccggtctt tattttattt ttagtagaga    2640
cagggttttg ctatgttgcc caggctggtc tcaaactcct gggcctaagt gatcctcctg    2700
ccttggcctc ccaaagtgct gggaactaca ggcgtgagcc actgggccca gctcctgtta    2760
acatctttat gtggagagtt actggggacc agggacattc cccaaaccca cccatcaatc    2820
gtagtgacat gacgttatgg accccctgat gtgatgtacc aggaagtacc cggccctacc    2880
agcatgatat tattctggct gcaactgacc cttattccaa tagagcatgt ggttctaagc    2940
catttatagg gtaaacattg ggcagggat ggggagagag gaagcaacct gccaaatcca     3000
gaatgaggat cattcctcgg taccagaaga gaaccagaaa gaaagcaccc taagtgggga    3060
taccacaagg aagtaaagca ggggcctctc ccagctgggg aagggaagga ggaaggagta    3120
caatagcttg caaggcacag cattgcggat gatgggaata gcaggtgcaa aggttctggg    3180
gcagggacag tgtggtgtgt ttgaagaaca gcagccaggt tcaccatgag atgggaaatg    3240
gacttggggg aagggatctc aaaggataat tttttttttt ttttgagac agggtttcgc     3300 tcttgttgcc caggctggag tgcagtggca tgatggctca ctgcaacctc tgccttccgg    3360
tttcaagcga ttctcctgcc tcagcctccc gagtagctgg gattacaggc gccaccacc     3420 acgcccggct aattttgta tttttagtag agacagggtt tcaccatgtt ggctagactg     3480
gtcttgaact cctgacctcg tgatccgccc gcctcggcct cccaaagtgc tgggattaca    3540
gacgtgagcc accgcgcccg gcccccaac tttttttttg ttttaacac aacttctcgc      3600 tttctcaccc aggctggagg gcagaggcac aatcatagct cactgcagcc tcgaactcct    3660
aggctccagc gatcctcaca ggagggtttt gaggatctgc ataaagcgtg cagagggagc    3720
ttgacttcgt gctcgttagg acccgatatt gtcagctgcc gccgcccaca gggacacata    3780
aatatttgta gactcaatat ttgcctttag tgtgaagaca ttgcatcacc tgggtataag    3840
```

```
taaggagcag aggcagaggc ggtttaagca acagactttt gtctccgctg agaaccacgg    3900
aataacccct gacctacttc cccgtcgtgt ctaattcggg tcacctcatc tccagttaca    3960
gacgcggaag atcaaagaaa ccgggaaatt gcgccgcagc gcccctggc gttcgcagcg     4020 cgtgcctaca caagccactc ccggcgcaaa actgcggctt cccaggaaat tgagtttaaa    4080 tgttttttt tctttttct taatctagaa aagatcattt attgtatcaa gtaactaccc      4140
agttaggcgt gaatacattt taaaatttt attaaaacga gtattggccg ggcgcggtgg     4200
ctcactcctg taatcccagc actttgggag gccaaggcag gtggatcacg gcgtcaggag    4260
ttcgagacca tcccggccaa catggtgaaa ccccgtctct actaaaaata caaaaattag    4320
ctgggcgtgg tggcacgcac ctgtagtccc agctactcgg gaggctgaga cagaagaatc    4380
ggttgaaccg gggaggcgga ggttgcagtg agctgagatc atgccactgc actccagcct    4440
gggcgacgga gcgagactcc atctccaaaa aataaataaa taaataaata taatataata   4500
taaaataaaa taaaagagt attgtagaga ttggctgggc acagtggctc acacctctaa    4560
ttcctgcatt ttgggaggct gaggtgggag gtcttcagcc caggagttag agaccagcct    4620
ggccaacatg gcaaaacccc atctctacta aaagtacaaa aattcgctgg gcatggtgtc    4680
gcacgtctgt gatcccagct ttttgggagg ctgaggcagg agaatcgctt gaacccagga    4740
ggcagaggtt acagtgaatc gagatcgcac cactgcactc cagcctgggc aacagagtga    4800
gaccttgtct caaaaataca tatatttagg aatttgctat gttgcccagg ctggcctcaa    4860
actcctggcc tcaagcaatc ctcccacctc gccctcccaa agtgctggga ttgcaggcgt    4920
gagccactgt gcccgacctt gagcttaagt tttaaacatt aaaaccacct ccctcccact    4980
ccctgcacct cccgtaagtt aaaacgcgtc cctgctgagg ccctgcaaag gcatatccag    5040
ggcaggcgga ccccaggggt ccacagccga cccactttct tccccacacc tcatcccctt    5100
cacaactctc ctcatccatc tccctgccct ggtgggagat tccgataaat cctaattgtg    5160
gaactgctga atcagagggg gctgcatttt ccttagcccc cacctgcaaa ttgtgtgtgc    5220 agttttctg ggatgagtgt ccttagattt ccctgaattc tcaaaaggat ctgtgacctc     5280
aaaatcagga gagaggccgg gcacggtggc tcacgcctgt catcccagta ctttgggagg    5340
ccgaggtggg cagatcgctt gagcccagga gaccagcctg gcaacatag ccagacccag     5400 tctctacaaa aaattaaaag attaactggg cttggtgatg tgcactcatg gtcccagcta    5460
ctcaggaggc tgaggtggga ggatcgcttg agcacaggcg gtaagagagg ctctacctct    5520
gaagaggatg cttccccacc ctctgccccc tccccaggca cccactccag cagtgagaat    5580
ttcactgcca acatgagaca tgggtcccta cctgtcccaa ctcagaccct gtctatgatg    5640
tcctatggcc tcagcaggga ccaaaacct caccatggcc tcaccagaac ctccacgtgg     5700
ttctcagatt gggttgcagg tcagtaccct cccctccagc tcctcagggg cctcctgcat    5760
tctctggcct tggcttctgc tctgccctcc cctcccttcc cttcgccccc ttcattttca    5820
ttctctatgc aaatgctgcc tcctctagga agccttccct gattgccccc agtctgggtg    5880
gattagatgt gatatgggct cccacagccc cttttgcctc agattactca gtgtggctggc   5940 tgtatatctg tgcccagag aggtttcttt tccttttct tttttttttt tttttttgag     6000 ataggggtgtc accttgccac ccaggctgga gtgcagtggc atgatcatag ctcattgcag   6060
tctcaacctc ccgggctcaa gcaatccttc cacctgaaag tcctgagcag ctgggactac    6120
aggcgtgtgc catcacgtgc ctgactaatt ttcttatttt tttgtagaga tggggtcttg    6180
ctatgttgcc caggctggtc ttaaactcct agcctcaagc gatctcccac ctcagtctcc    6240
```

```
tgagtaaact ggaccccagg tgcaagacac catgcccata aaaaaatttt aaaaaaattt    6300
aattttaaaa ttttttttgta gagataggat cgtgttatgc cgcccaggct ggtctcaaac    6360
tcctgggccc aagcgatcct cccacctagg cctcccaaag cactgggatt acaggtgtaa    6420
gctacctcgc ccggcctctc ctgttctatt ggtgctgtga gattcacacc tcacttgagt    6480
gctatgggct gaactgtgtc ctctccacaa atgtctatgc tgaagtcctg ccccgcaact    6540
gcctcagaaa gtgactatac ttggagatag aatctttaaa gaataatta agtaaaaatg     6600 aggtcatatg cgtgggccct aatccaacat gaccagtttc cttgtaagaa gagcagatta    6660
ggacacagac atgcactggg gcggggggag gagactgtgt gaacacacag gaaaacaca     6720 gctgtctaca aggaaaggag agaagcttca gaaggagtca cacctgtgga catcttcatc    6780
ttggacttcc agtctctaga aacagaagac tataaatgtg tttgctttga cagagagtct    6840
tgctctgttg cccaggctgg agtgcaacgg tgcgatctca gctcactaca acctccgcct    6900
cccgaaggag cgtagtgta attcctcctgc ctcagcctcc caagtagctg gtaccacagg    6960
tgtccaccac cacacctggc taattttttgt attttttagta gagacaaggt ttcaccatgt   7020
tggccaggct tgtcttgaac tcctgacctc aggtgatcca cctgcctcag cctctcaaag    7080
tgctgggatt atagttttgt ttttgagatg gaggtctcgc ttttgtcacc caaggctgga    7140
gtgcactggc acgtcttgg ctcactgcaa cctctgcctc ccaggctcaa atgatcctcc     7200
cacctcagcc tcctgagtag ctgggaccac ggtgcacacc actacattca gctaattcta    7260 ttttttttgta gacacaggat ctcactatgt tgcccaggct agtcttgaac tcctggcctc    7320
aagtgatcaa cctgccttgg cctcccaatg tgcgactaca ggcatgagcc acggtgcctg    7380
gcaatttctg ttaagtcacc tagtctgtgg tactttgtta tgacagccct agcaaacaga    7440
tacacccacc gaaggccctg ataagtcctg cagtcaggag tctctgtgaa ccccgtgggg    7500 ctggaggag aaagcaggga gcgttttgctg tgtgcctcac atgaatacag cagaagctga    7560
acacaactcc tggcatcgta tgcctacagg tcccccttgga acagttctag gggggttgga   7620
gttccagggt ccattctgct taataacaat attaacggag cagccaaaat ggttccagtg    7680
aaaatggggt agcagcagct gtcatgcttg cacgccacca gccttcctgc gctatctctg    7740
ttctctcctc tgcaaagcag ctgctatttt gggctccctg tttttagatt gggaaccccg    7800
gaagttggtc agggcctcac cgctagaata tcttagagct gatattcaaa tgagagtcca    7860 atttttttt ttttgagacg gagtctcgct ttgttgccca ggttggagtg caaaggggca    7920
atctcggctc actgcagcct ccacatcctg ggttcaagtg attctcctgc ctcagcctcc    7980
caagtagctg ggactacagg tgcacaccac cacacccagc tagttgtttt gtatttctag    8040
tagagatggg ttttcaccat gttggccagg ctggtcttga agtcctgacc tcaagtgatc    8100
ctcccgcctt ggcctcccaa agtgctggga ttacaggcgt gagccaccgt gccctgccaa    8160
aagtccaagt tcttaacctc catgagggct tgagatgccc tcaggggcag ggagaggcta    8220
attctccttc tgagaggata ataggggttg gtggggcctg gggcacaggc ctggctcagc    8280
acaactccca gggactccct tgataagaag gtgaggtagg cactggctgg cagagcgacg    8340
ggaagagttt atttctctgg aaagggaggg gtaggggcg gggccagggg tcagggcagg    8400
gcaatgtcct ccagcttctt gtccagtgcc ttcaggtcat ccaggaagcg ggtcggggtg    8460
aggatgtgtg aggagcctgt gcaggggcag aggtttgggg aagatgttgg ggggcgctgc    8520
cttcgtcttt gacaggctcc cggtcccggc tggtgtgggg ctgtccctgt ccctcagcaa    8580
accaggtccc tgactccaag gactctggag tccagacacc tagaaggtac aagcccaggc    8640
```

| | |
|---|---|
| cccgggaacc caagccccag accccagggt cccagtcctg gtgacttacc aatgagcacc | 8700 |
| tcccacttgc cctcggtggc cctggtcacc tcgtaggcgg ccctcatctc tgacatggcc | 8760 |
| acaccgccca tgacatacac gatgagccgg gggcccgccc gggcttctat gccagccttg | 8820 |
| ttcttgtgcc agtgaccgaa gcgggcactg tgcaggcag gggcagaaag tccaggcagg | 8880 |
| aggccctcac cgccgccagg ccgcccacct aacacagacc caggcgtggg cggggcggc | 8940 |
| cccgggcct cacctgacag cggcctggga gctggccgtg ggggcgggt cggatacgaa | 9000 |
| gggccacagg ttcctgtcca gccggtcctc cacggcgtcc tggcggccga gaggcaggtt | 9060 |
| aggggaggaa ccccaggcat ggggtccggg gtcaggagtg ccccccacgg ggtattcagg | 9120 |
| ggccaagatc ctggcagaca ggaaccagca tctccacctc ctgcctctgg gggacccagg | 9180 |
| agtctaggcc tctagtccat tgggaccta gaaatctaga tccataactc actgggacc | 9240 |
| cacgaatcta attccataac tccttgggta cccagaagtc taaacccaca gttcctcggc | 9300 |
| aacccagtag tctgggcctc caggcccttg ggaccatca gtcaataccc ccagcccttt | 9360 |
| ggggaaccca gtgtctgggc tctcagcccc tcagagcccc agaagtccag gtattcaagg | 9420 |
| tccatgggga tgaggaggcc caggtctctg gcccccacgc agaaagaggg gccggggctc | 9480 |
| ttagagggac aaggaggaag ccaggaagcc gccccaggcc cattgccatt ggatggtgct | 9540 |
| gccctgggat cctgggaagg ccagggctgg ggctcagggg cactcctgcg ggacagggga | 9600 |
| acagactaga gagatatagc ggaggcagcc ggcaggtggg gaggaagtga ggctccccag | 9660 |
| cacaggcccc gctgtcaccc caattcctca gctgcgggct tggcgtgccc ccctcagcag | 9720 |
| agcagatcgg tgccaaggga atgccagcaa tgagcatttt cccctaagcc ctgaggctta | 9780 |
| gcacctcagc aggagggagg ctgagccgcc agccgatgcg gagggctggc ccccaccctg | 9840 |
| acctgccacc cagtacctcc attacatcct tgatgaccgg ggtccagcgg gacagctgat | 9900 |
| aggtgggctc catgcgttct ctcggctcca gccggctgga ggtccccgag ccctacaggc | 9960 |
| agggcaggga gggcagcagg gggattgagg ggaaggaggc tggtcacaga ggggctgcgc | 10020 |
| ctggtgtggc tggtagggtg ggggatggca ggcaaagatg gggaagtgga acagagagcg | 10080 |
| agagagagcg agagacagca agaaagcgag agagagaaac agtgagccag agagagacgg | 10140 |
| agagagaaag ccaagggag agagagcgag ccagagaaag acaaagacag aggcagagat | 10200 |
| aggcaaagag ataagaagca gtgagacaaa gtatgaaggc aaagagagag acaagagatg | 10260 |
| aagcaggaaa cagagagagg aagatgggga cagaaggggg acggagaggg gaggggagca | 10320 |
| agacagagaa cagagagaaa ggggaaggca gagagaaggg tgagagagag agatatggag | 10380 |
| aaacagtgca cagcgagatg gatgagggat gggggagaga tggggacggg gtgagggcac | 10440 |
| cctggagggg gacgcacagg gccagagaga gacaggagag gctgacccaa gagtcaagca | 10500 |
| cacacatggc tgtgtgtggg tgctggatgg gtgcggggga ccctcagaga cccctgggag | 10560 |
| cccagataga caatgtggtg tagccccat gctgggaccc ctactccctg cctctagcac | 10620 |
| tcagaccacc cgctcccaac tgcaccactg ccaggaccag cctggcagcg accatgtctc | 10680 |
| acttcccctg cctattgtgt aagctgggac tgggagaggc cccagtgtcc tctgggcccc | 10740 |
| agaccagacc cgaaacactg ctttttggcct cccagcaacc acaccacgcc aggaaccaca | 10800 |
| ccgtgcctgt gcaccaatgg ccctctgcct tgcagagccc cggctgtgat ccgcaccctc | 10860 |
| tcccagggtc cccccatgcc cgctcctggc gtaccccggg gttggtgaca gtgcctccca | 10920 |
| gctgctccag gttacggatg aggctgctgt gcgcctgtac attggcatgc tggatcagct | 10980 |
| tggccaggtt ctcctcactc acacctgggg gacgggaatg ggcagggtgg aggcggcggc | 11040 |

```
caggtgagct cccaggttta ggggagtttg gggtgggctg aggagctccc aggactctga   11100
tgagagaacc ttgcagtggg gagggcctca gtaccctgtg ctagtgtgag caagagtggg   11160
aaacctggag ggggtagatc aggggctcct ccagatgagc tgagggagcc ccacatctat   11220
aggaatcaca gatgtgaggg tttctacgtt agcaggagcc cctcacctca gtggaggaat   11280
ccccaagcca atggaggagg gttcccgggt ccagaggggt agctgtgggg gttggtgagc   11340
ccggtgagtg caaatgaccc aaggagagct gtggggttca gcagttccca ggatcgtggg   11400
agacgctggc aaatggggac gttccaactc cctgcagccc ccacccacca ttccgaagga   11460
ggatgtagag cagcaggacc cggatcttgt cgtaggcggg caccgccgcg tccagcagca   11520
ccggaacgat cagcttcatg gagtccttga tcttctcccc ctctgcgtcg gagcccatgg   11580
ccaggtcctg cgggcatggg gtcagccgtc caccggccgc tatgtgtcag ggaaggggat   11640
gggagaggcg ggccaaggac atccccagga tcctcggcaa aggacatttt gggtcctacc   11700
tcatctcagc accaggtctc tcaaggtccc acccctgtcc agggacagtc tctccacagg   11760
ccctgctcct cacccaggtc ccacctttcc agtgcccac ccacctacac acaggtcaca   11820
ccactatcct gagactacct ctccaaggct ccacccctca cccaggtccc agctctccaa   11880
ggctccaccc ctcacccagg tcccagctct ccgaggctcc acccctcacc caggtcccac   11940
ctctccgagg ttccacccct cacccaggtc ccacctctcc gaggttccac acctcaccca   12000
ggtcccacct ctccgaggct ccacccctca cccaggtccc acctctccaa ggctccaccc   12060
ctcacccaag tcccacctct ccaaggctcc acccctcacc caggtcccag ctctccaagg   12120
ctccacccct cacccaggtc ccacctctcc aaggctccac ccctcaccca ggtcccacct   12180
ctccgaggtt ccacccctca cccaggtccc acctctccaa ggccccgtgc ctcacccaga   12240
tcccacctct ccatggctct acctgtctcc cagctcctac ctctccaagg ccccaccct   12300 cactcaggtc ccacctctcc aaggctccgc cctctccca ggtcccacct ctcttaaggc   12360
tccacccctc tcccaggtcc caccctccaa aggttcacc cctcatccag gtcccacctc   12420
tccaaggttc caccctcac ccaggtccca cctctccaag gctccgcccc tcacccaggt   12480
cccacctctc caaggctccg ccctctccc agggcccacc tctccaaggc tccattcctc   12540
tcccaggtcc cacctctcca aggtctgcc cctcacccag gtcccacctc tccaaggctc   12600
cattcctctc ccaggtcgca cctctccaag gccctgccta cctctccaag gtcccaccca   12660
cctatgaata ggccacattc ctgtcctggg accacctgtc caaggctctg ccctcaccc   12720 aagtctgacc tctccaagcc ccatccacct atgcacaggc cacaccctca tcctaggacc   12780
gtttctccac aagacccact ccttccccac caggtcccac ctctctccaa ggcccctcca   12840
cctctccaca agccctgccc ctcccccaga accccccatc tctacagttc agcccctccc   12900 caatacccg ccttggcagg accatcaccc ctgcccccg caagccctgc cccacctgct   12960
ccacactaca cagcttctcc accgagccct tgaagtgctt catacaatca tctgctagat   13020
gcaggtgcgt agaatactgc agggtgcagg gtgggggttg gggataaaca aaggctgagt   13080
caaggcagaa cgcagacaga gcatggggtt gaggggccga ggtgtccccg ctccctgccc   13140
acccgagcac accttattca gctccttctg gtactgcggc atcttttca ggatctggga   13200 taggtctttg atgttcgcct ggggaagtag ggggaagagg gtagggattg gggggcgaag   13260
ccaggcagtg cccacctggg tctcagtcca ggctcgaaat ccaggctgtg ccctgcgcc   13320 catggggagg ggggcttcct tccaccacgc ccttttggtga cctgggtccg cccctaccttt  13380 gtccgtggtc agcctcttgc tctcacagaa ggtcctcagg agctccgtga ccttcctggc   13440
```

```
catgagggtg ggcggggtg agagtgaggg gagaggagcc acaggccatg ggtgagccca     13500
ctcaggggg acaggagag gtggggtgaa attggaggcc agtctggagt cacacgaggg      13560
gtgctcatga gggccaaaga cttggcagca gccagggatc ccaaggccgc taccaggccc    13620
acagtgggcg gtgggggggg gatccggtcc ccgtgtgcac gcacttggac acatctgcga    13680
tatgcatgtg gcgaagctcc acccacaagt catcgtcctc gtccagcaag acggccttct    13740
cccgcgcctc gctcagcccg gtggtctcat acctggggag gaaggaggga gcctggggt     13800
caggggagct gaggactggg gaaccaggtc agtggcaagg gtggggacgg gttccaagtc    13860
tgcagacctg tatgtgtcct gctctatgtc cagcagatca tacgccatgg cctggaacgt    13920
gagctcatgc agtagtgggg acacggggtc agctgcccgg tccattatca gcagctggga    13980
gcgggttttc tctgggccct ggggtggggt ttagggcagg aatgaggcac tgaccctgag    14040
ccggttgggg ctgcccctca cctcccaagc acgccccctc acctcgccca gactgggagt    14100
gtctgccttg aaggcgttca gcttggccag gacggcgtgg gccaactggg ctgtgtcctc    14160
tgggcccctg gcggggaggt cagacacggg ggacatcatc aggggatggg gtcaaggatg    14220
ggtttgaagg tgagagtcag gggccagggt agggccgggg ctgggtcac aagagaggtt     14280
aaaggttagg tgttgcacgc ggttaagggg gggtcggcat cggggtgggg ctgggtgggg   14340
tccccacttg cggtagcgga tggccgggta ctcctgcagg gtggcgcaca gcgtggcaat    14400
ctgctgggcc agcacctcga gctgccgcgt gcgctcctct gcccggaagg ggcagtagag    14460
gttgtaggtg ctgtggggag catcgaggga gaacacctgg gcgaggaggg gacagaagca    14520
ccagggttgc cgctgcaggt gcacacctgc cccgcttccc gctgccgcca cctgcacctc    14580
ctgggagccg tccctggtcc ctgaagcctg ctttgccgaa ttggaggcag gcccaggtca    14640
accctaaacc catgcctgca ggagtcagtg gataaatacc ccagcccgtg tcccttaagc    14700
tggctggaca accccgcggt gcgctctacg ctgcccctg caagggccta gtgggataga    14760
actcaaggca agagctcctt ggactctgtg ggtacctccc cttttttaaaa ttttacttta   14820
tgtatgtttt tgagacagga tctcgctctg tcgcccaggc tggagggcag cagtgcaatc    14880
atagctcact gcagcctcga cctcccgggc tcaagcgact ctcccacccc agccccatga    14940
gtagctagga ctacaggtgc acgccaccac gccaagctaa tttctttctt tttctttttt    15000
taagagacgg ggtcttgctc tgtacccagg ctggtctcaa actcctggcc ccaagtgatc    15060
ctcctgccct ggcctcccac agcgctggga ttacaggtat gagccactgc gcccagcctc    15120
agtgtctgtt tctgagggaa caggggacat ttggtcacaa accccacccc cctgcccagg    15180
atgagcccgg gccgtacctg ggcctcgtag gggaggaagg caaggtgaat ctccttcaac    15240
gtcttcacca cctttgccag acgagagcgg cctagctcac tgaacagggg ctcggggcag    15300
gctggggtga ggcaggagtg gggcatcagg ccagagcagc ccccacacct ccttgcccca    15360
cccaccaaca ccctaggctc tcctcactca ctgtcggtga agaagatatg ggccgctttg    15420
taggtgaaag tcgggggtccc ctggaagtct ttgatcaggg cctgaaccga ctggggaagg   15480
tggatcactc tctgggcctg agcctgcaca cctaggctca ttggctgcct aggcctccca    15540
gccaccccc atctgccacc atgtgcaaac atggacggac ggggacatgt atatgtgcaa     15600
atgcacacta gtgtcgcacc cacatgggca cacgcgcaca cacacagatg cacgcacgca    15660
cacacacata cacacgcatg cacacatgca cacacacaca gatgcacaca cacatacaca    15720
catgcacaca cagagatgca cacacatacta tacacacatg cacacacaca gatgcgcgcg    15780
cacacatata tacacacata tacacacatg cagacactga tgcgcacaca cacgcataca    15840
```

| | |
|---|---|
| cacatgcaca gacgcataca cacacgcata cacagcaca cacagatgca cacacataca | 15900 |
| tagacacatg cacacagatg cacatacata tacacgcata cacacatgca cacacagata | 15960 |
| cacacagacg cacacacaga cgcagacaca tacatacaca cgcatacaca catgcacaca | 16020 |
| gacagacgca cacacacaca tacagatgca cacagatgca cacacacata catacacacg | 16080 |
| catacacaca tgcacagaca caaatgcaca cacagaccca cagacacaca cgcatacaca | 16140 |
| catacacaca aatgcacaca cagacgcaca cacatgcaca tgcacacaga cacatacata | 16200 |
| gacacacatg caaacacgca cacacatgca tacacagatg cacacacaca tgcacacaca | 16260 |
| tgcacacaca tacacatgga cacatgcaca cgtatacaca tgcacacatg caatcacatg | 16320 |
| catgcagaca tacacacaca tgcacatgta cacgcatgca cgcgcataca cacacgctca | 16380 |
| ctcatgtagg caccttctcc gtggggctca gcaaataaat ggcctccaga ctgggaatgg | 16440 |
| gttcccgccg tttgttgatg tcttcaacaa ctagtaggaa cagaggaagg gacacaggtg | 16500 |
| ggtggcatcc aggcagggcc acgtggggag tctcaggtgt gggggggttgg aggcttgggg | 16560 |
| aggaggggtg gatgcttagg agggactgca ggagaaaccc acttagggac caccagctaa | 16620 |
| gagccacacg acagggttct gcaggggttg tgcagccaac tgggttcccc aaatttacag | 16680 |
| acagggagac tgaggttctg agaggacagg ctccctcagc acctatccct caatggcaaa | 16740 |
| gtgactggga caccacctgg ggtcacccat agaaggctct gcattcttgg gacccacat | 16800 |
| ccagagtcca ccctgggagt cccacacagg gctccacgag ggagctgcac ggtcaggaag | 16860 |
| gggctgcagc cagggagtgc tgcagggagg cctgcaatc catgggctcc cgcagtcagc | 16920 |
| ttgcaaggtt taagaatgga tttggtcaca tgatccgggc tgtccgtgca gggagctgcg | 16980 |
| tacttgggag ttctggacga tttgagggga tcctacactc aagggctgaa ccctgggaga | 17040 |
| ggggcacagt caggggttcc cacgctcagg tcccatctca ctggggacgc gttcactcac | 17100 |
| tggtgatgcc ctcagccagg atatctgaca ttttgcagca ggaagacaag atgcgcatgc | 17160 |
| ttgggtgatc catgataagc acctgtccag atggatggac agatggatgg aggagcaggc | 17220 |
| ggaagaggcc acagctggcc ccagaagggg ccaaggcagt gggaggggca gtttcaaggg | 17280 |
| ctggctgggt ggggaggaccc agaacccatt cacccaactc cacccatgtg gacaggcagt | 17340 |
| tcttgggggt cccacattca gggtcttccc cataggcctg atgatgagct gcctctgggt | 17400 |
| acccagccat ctgcctcacc cctaccttcc actcccatc cttcttgaca ctccgaataa | 17460 |
| ctccgctcag aatttctgca gggaagggag gggaggggtc agaatgctgg ttctctggtc | 17520 |
| ccaccactgc cccaagcctt tcagccttg ggctgaacc cccatcttaa ttcccattta | 17580 |
| ctttttttt tttttttaaga gaggaggatc tcactctgtc acctaggcta aagtgcagtg | 17640 |
| gtgtgatcat aactcactgc ggcctccaac tcctgggctc cagcgatcct cttgcctcag | 17700 |
| cctcccgagt agctgggact acaggtgcat gtaccaccca cagctaattt atttttattt | 17760 |
| ctgtatagat ggggtctcgc tatgttgccc aagctggtct caaacttttg gcctcaagca | 17820 |
| gtcctcctgc ctcggcctcc caaagtgctg ggattacagg tgtgagacac ggcacaggaa | 17880 |
| tcatttattt ttagccccca gttctgcaaa ttggcttctg gggtcacccc caatttacag | 17940 |
| acagggaaac agattcttag gcaacatgta actcacctac gcatcctgag tgtctaagtg | 18000 |
| gcagagtgct ggggcaaaag gtgccactcg ataaacatgt tttaggtgaa tgaaaagagg | 18060 |
| agaaccggga tcatctacag ctctatctgc ctctagcgcc aggctctcgg cttccccacc | 18120 |
| tgctacctca agtattcctg ctgtgagggt ttcagccagt cccccaacc tggtctaaaa | 18180 |
| tgtaggaccc ctggttccca gctctgaggc atgcctagct gaggctatcc cactgacctc | 18240 |

```
cggtctcagt ttcctcatct gtaaaatgga atcactttt  tctaatctcc cccaattaaa    18300 gggtttgag  ctacagaccg ccctgcctag aggagagagt ggagagaagt aacggggtgg    18360
ccccgcccag ccacgtccac tgtgtcatgt ccactgttat caagacggcc agggcggaag    18420
gagcagctga ggccggaact ccccggggtg gaggaagagg cgccctccac ccttccccca    18480
agaaccgggg ccggtgaggc ctggacgcct gcgtcctcca gctgcaaggc gctcctggaa    18540
atggggcaag gaggaagaca tcccctacac caccctgtg  gggcctggac acgtcccctg    18600
agcgctcaca gcacctaggg tcgctgacca gagccctagg aggccccaag aatccagccc    18660
ctgaactttg cccggcttaa gagatcctag agtgtgggca tccagctgtg ccctcctccc    18720
ccggcaggca ccctaggagg cccaggagtc cgggcccag  cctccgccac actctacccg    18780
tcccctttgg gtccccggag tccggccccc caattttgtt ctgttctggc accgagagc    18840 aggggcgtcc agctgggaac ccgtccccgc ccgcccctc  gagggtcagg tgctcggacg    18900
cccagcccgg cccccaactc ccagccgcca tgaaacccag gatcccagag cccgtgcgtc    18960 cccgacccc  gtcccacacc ggacgccaga gcccggcccc ggagaggcac tcactttccc    19020
ccaccaccgc cttcagcccc gagggcgcca tcttccccga ggggcgccgc cgccgcttcc    19080
gggtgtgtcc caaggtgggg gcgtggccgc gcgtcaccca cgtggacccc gccccgcgcc    19140
ctgtccccgc ccctgcgca  cctggcccct ccccgccgtc ggttctcgcc caggcccagg    19200
aagttgagtc cctggcgggg aggacgggca ggtgcgtccg cgctgccgag cacgaagtcg    19260
ctggaggtgc acacctcgac gacacgctca cagatgggag ttcagacaca cacttcctgg    19320
cttgcgtgcg aagcaggatc gcagggcaat aatccctcca tcttcccgg  gaggttctgt    19380 gcctgcaaga tacacggcac ccactcgatg ccaccgggcc gccactgtct gggcctggga    19440
tcttgaccca cttgccttct gtacttcagg gtttagaggc agcagcagca gcagcagccg    19500
tcttggataa cttttgatgg attcaggagg cctggagacc tcttgtgtgc aggcacctgg    19560
acataatttt cattcagtcc tgcccaatgt tccgacctgg actgcggtgc cgacgaggaa    19620
accgaggctt agcgggatcc ctaatccaag gccacgacga gtgagcctgc tgggttcaag    19680
ccaggagcct gtccccaggg ggcatttgtc acagccttac cctcttccgg gagggcgcaa    19740
cgcttaccct cgtggaccaa caatcgaatt aacatgctga tacacacatg gggtgagtga    19800
cgccctcaaa tgcttgcaaa cacagacaca cactcggaat tcagaagct  gcttctgctg    19860 tgtgtcctgt cgcttggaag gcacagcccc agcagcaccc atacaaaatg aggtctccga    19920
tttaaggtgc gaggtatgtg tgcaaacaga ctcttgctgg tctgagctgg ttccttcgct    19980
cggccgtgtt gatgaaggta ccaagccccc tgccacttac atgggacata gggagtgaat    20040
cagacccgaa ggtctggggg agataggaaa ggatccatgc tgccctaaag gaataaaact    20100
aatgtgacaa caagtgccac agaaggtagg ggtgggaggg gactttactg aggatgaccc    20160
ccgagggcct ctctgaagaa gcagccttt  gacattatcc ctaaatggat tctagaagca    20220
gccacacagc atgtccaggt agagaaggga ggagcccga  gcttaagaag gctggagggt    20280
gggggcagca ggggccagac ttctgtagga caaggtcaga ctgacccatc ccagtgccag    20340
gatgcaggac tttcagtgct aaaaatagga cagtcacagg caaaccagga cggttggcaa    20400
ccgtaggtag gagtttgagc tatttcttcc tttccttttcc ttttcccttc ctttcttcct    20460
tcttctccct cctccccatt tttgtttgtt tttgttttgt aaagagacgg gtctcgctct    20520
gttgctcagg ctgagggca  gtggcacgat catagctcac tgcagcctcg acttcctgag    20580
ctcaagggat tcttccactt cggccaccca agtagctggg actacaggtg cacgccaccg    20640
```

```
tgcccggttg attttgttgt tgttgttaag agacaggatc tccctatgtt gcccaggctg   20700
gtatcaaact cctgggctca agggatcctc ctgccttggc ctcccaaagt gttaggattt   20760
taggtatgag ccaccgcacg ctgccccttc ctccttttgt aacagcttta ctgagatata   20820
attcacatac catacaactc gctgacctaa ggtgcgtaag tcaatggctt tcagtatttt   20880
tggagttgtg tgtccattac cacaatccat tttagaacat ttccacaacc cctaggtgtt   20940
tgggttttgt cttctcaaga gttttgagca ggggaaggcg gggaaccctc cagatcctgg   21000
ggggatggaa gccaggaccg cctccagctt ctcagcctga ccccttgggg ggacagagag   21060
ctgttagggc cagccacccc accactaacc cccaaaagat atgaagtact aatccccaat   21120
accccacaat aggatcttat ttgaaatggg gttagtatag atattagcag tgagcatgag   21180
gtcacactgg agtagagtag gcccctaatg caatatcact ggtgtccttg taagatagtt   21240
atatgtctgc ctggttctgt gtaggtggtt ggggggtgg ggaaatgggt atatgaagac   21300
tgggacacag agggagaatg ccatgtgacc acggaggcag ggagtgaaga gctgcagtga   21360
caagccaagg acatcaagga cggcaggcca ctgccaaaag ccagggaggg gcaaggaggg   21420
ctcctgagac ctggttttca gagggagcac agctctgcca acaccttcat ttcaggctgt   21480
ggcctctgga acgttggctc aataaatttg ttaaaaaaaa attttaaagg ctcagcatgg   21540
tggctcatgc ctgtaatccc agcactttgg gaggcccagg caggaggatc acatgaaccc   21600
aggagtttga gactagcctg gcaaaatag tgagacctca tctctatata aaatatata   21660 acaaaagtca acttatgtgt tttaagccat ctggtctatg cactttgtt ctggcaggcc   21720 taggaaaggg atacacgtac tgaggagggg gacacttcat tggcatagag ggagagagtg   21780
tgaacttggc cttttgtgga acagaggagg ctcgggcaga ggtggtgata gtgcagccca   21840
ttcattctga gatgaaactt ccactggttt ccgtaaaggc gtcttgggga gggaagggaa   21900
ggggatgggg acctcccagt ggtatcccct gcttgggcac tgaggaaaag ccacagtggc   21960
tcgggggaaa aggcagggac gtcctctccc cgcctgcctc tgtccccagg gagtctcgcc   22020
tcctgttccc acctgggget agggtgatag aggagaggag atagctcaac ctggcattta   22080
ggtggtgtgg gaacaggaga ccccagactt tcttgttttg gggtctgggg caggcaacca   22140
ggctccaggg acagtgagtt gaaggaaggg tggctgggag accccttgac ttgctgccaa   22200
ggagacagag ctggagctag ggtggccggt ggtgtctgag gcaggtgcag agagggaggg   22260
agggaagggg cctttgactc caacctcctt tttctgtacc gactgcaggt ggcagctgcc   22320
cttttcagga g ccagtgggg aacctggtg gctgggtggg gacacctgca gtcctccct   22380 aagccagcta ccaccctaca ctgttggcct cccttctcca actgtgggga tgctgctcag   22440
gccttttgtg acatcacacc tgagagtccc tggggtccag tcattgctgc tgggcacagc   22500
gaggtccaag ctcaggtcgc cctgcccct acccaccatg ccagatccag catcgttgtg   22560
ggcaaacaat tatctggatg atctttatgg ggcttaagct tgggtgggag cagatggggc   22620
atgagctggg gatttgggga tgggggaat ccacaccccc acgtcctgga cgtttaaaag   22680
gccctctctg gcactgggcc ggggcagagg ccagcagaaa agtgactgga gtccaggac   22740 atgatggatc aggaggagaa gacggaggaa ggctcaggcc cctgtgccga ggtgagaggg   22800
ccctgccccc accccacccc cagctcaagg tctcagagcc catgattgac aagactagtt   22860
tgtagggcac ctaattaacg agtgagtctc ctaggacccc ctgacccagt tgtggctgta   22920
gaaaggggct ggtgggcttg ggggtctgag tgccaggccc cagggcagag ggcagggctc   22980
tccgtgtgga cccctattga tgggagatgc tgggacctgg gggtagctcc tgggccatgt   23040
```

```
ttccctgatt cgtgtcccag ctcccaggcc acactcatca ggccccaatc taggacggcg    23100
ggacacgcat cggagcctgt cccttgaagc ggtaccacgt gaagtggcac tgctggccag    23160
ggcccctggg gcggggccg  ggattgggaa ggagactcat gtctcattca gaacagctct    23220
gcagagagga tcggcgggga ccatggtgag agctgaggaa gtgggacgg  caggccccgg    23280 ggtcagggtg tgagcaagct ggctaggaag tttggggagg ggccccaag  ctgaagggcc    23340 aaccagactg agcgagtctg tccccaggcg ggctccccag accaggaggg cttcttcaat    23400
ctgctgagcc acgtgcaggg cgaccggatg gagggacagc gctgttcact gcaagccggg    23460
ccgggccaga ccaccaagag ccgtgagcat gggcacgggg gtgctgtcca tgggcgtga   23520 acggggtggg agtgcagggc aagtggtcat ctggagggcc tgggggcacg ggatgtggga    23580
ggtggttgtg caccctgaag catctgtgtg gggtgaagg  ggtagggttg ggggccccca    23640
ctccggctgt gtcctcccaa gtctgtgaac gtccacgcag agagcgaccc cacccccgag    23700
atggacagcc tcatggacat gctggccagt acccagggcc gccgcatgga tgaccaacgt    23760
gtgacagtca gcacgctgcc cgcttccagc ccgtggggtc caaggtaggt gatgttctgg    23820
cgatgtcgag gagaaacccg ccaggcagtg ctctccgatc ctgccctcca ccccagccag    23880
gagggaacag ggcctgcccc atctctgtcc atccgctgcc ctgacttcag atgggaggac    23940
caaggcccag gcagtggcta gaggggccca aggttataca ggggccatgc tagtgtaaga    24000
cccatggctg gaacttgtgg ctcctgcccc caagtctgaa ggttctgggg aggccaaagg    24060
gagaaaatag gaccccttcc taggaaagta tcccagggag gaagtcacgt aagctcacac    24120
ataggatata tacatctgta tactcacatc tgttgacttc acacatacac gaagcttggg    24180
ttctgatcaa gatcccagcg agggcccaa  gacctgccac ctcacactca aatgccaccc    24240
taaatggcag atattgaggg taaacataga ccagtgctca caatgaggtg ggacacggtg    24300
gctacctgca ccctctctcc attgttcgcc acctgtggcc ggcactgccc ttgagccctc    24360
cccctggctg acccctcttc atccacagga cggagcacag aaacgagctg ggaccctcag    24420
tccccaaccc ctgctcaccc ctcaggaccc gaccgctctc ggcttccgtc ggaacagcag    24480
cccccagccc ccgacacaag ccccctgagg gcctgaggca tcctgggtct cactcggccc    24540
ccaaaaactg ataaaagaat aaaacactta aatgaataac aaggaactga gtatatgtat    24600
atttcatcag ggagggggct aggactccca cttggaggcc tcaggagttc tgctgggcgt    24660
cgcgaaggag cttctcctcc cgccgcttcc gtaacctctc tttgaattcc tctatctctt    24720
gaagctaggt gtggagaagc gggtgggaca ggaaggggg  aggggcacac acctcagagc    24780
cgggaccccc ccccccgcc  cacctctccc accaccctgc cccagaccac ggcttcaggg    24840
ttcagtgtct tcactggaag ccccctgcca attacaaagg ggtccgcgtg ggatccgctt    24900
cactcttcca ggagaaggca ataaggaaac catctactcc tctgctctcg gttccttact    24960
catggctgag agtaaaatgt ttcttttttga gacaaagtct cactctattg cccaggctgg    25020
agtgcagtgg cgtgatcttg ggctcactgc aacctccacc tcctgggttc aagtgattct    25080
tctccctcag cctcccaagc agctggaatt ataggcgcct gccaccatgc ctggctaagt    25140
tttgtatttc tgtagacatg gggtttcgcc atgttggcca ggctggtttt gaactcctga    25200
cctcaagtga tctacccacc tcagcctccc atgccctggg attacaagca tgagccactg    25260
cgcctggcct aaaattttca tctaaaaccc atcccggata caagaatcca gcctcctcca    25320
tccctctggc aggaagaaga gatcacttac cttctcaggt ggccacagct ccctctgtaa    25380
ggaaaagtca caaatgggac acgagccaaa ggcctccaga gccccacatc agggcagggt    25440
```

```
cggcttatgg gaggcagaca ttagtcccca gcagactgct gccccacacc ctctcccacc    25500
cctggaatga acccctcaaac actcctctta tgcccaccttt gcgctgtatg acatcgtcct   25560
caaaccactc ggcctgattg gaaacccaga acatagccac agggaaagtg aggtagatta    25620
tcatctggaa tggcagaggg tgggtgaggt gagctccccc caagcaatgt gcagaggctc    25680
ctcagagcct gggggaccca tcctactgca gagtccagaa gcgcctcgtt acggccgacc    25740
caagaatccc agaactccca ccaagggtac agaaacctcg caccctaaaa cctaactcct    25800
ataatccagg aggcctcatt cctgaaagtt ccctctgagc tggagtcttc ctctcaaaca    25860
cagacagaca cacagacgcc ccagctacaa tcaaaagcat ctcctcgaga cctcattacc    25920
catccccact taagatcccg ggagcacccc caaacccagg aggcgtcact cttcaactcc    25980
acttctcgaa gtctaggaat ctccctgtca tagacaccca cccaccacga gcccgagagc    26040
tccccaggga tcttaagtct tccttcttta gagcccccctt ctcagctcac ccctctctga   26100
ggtccttcct cggaccagcc ctctcacagc ccccaaaatc agaagcacaa atccgagaac    26160 cccccccagcc cagcgtcccc tctcctggat ttccaaccag aaaggtcctc tcaaatctta   26220
agagctttct ccttggagct ccctcttcct ttgaagtccc cccatttcca acctcatctt    26280
cagatccagg aagatcccct gcccagcctc ccaacccact cctgtgtcca ctgacccgaa    26340
atatctccag cttcaccccc atctcgtttc tcccggtcaa caaagccagt tccgcccaaa    26400
gccgaccctc cagcaagaca gaagctcact ggtgttttgc acgctccatt gctgaagctg    26460
attggccaat gtgtatcctc atggcgcatc ttctggcgcc tctattctgc ttccggtcgc    26520
tggcgtcgtc gaaaagaagt caataacgtg ggcctgtccg tcaaaaatga tttaaccaat    26580
agaaaacggg tctggctcgg aggggcgggc cgtcagtggt agacgtcata agcgcgcgac    26640
tctctcctgt acctgggcat ccagaaaaat ggtggtgatg gcgcgactct cgcggcccga    26700
gcggccggac cttgtcttcg tgagtccaca gaggagccgg gggtggcctg cgttggggca    26760
ttgggacctg gacgccgcag gggatcgagg ctgggtcggc aaggagattt aggccgaaac    26820
tgccaggcca aggtctggga accctaatgg gccagagacc ggatcgtcat gtccgcaccg    26880
aactgtccag gagtaaaaat atggtgttgt atcttcgggt ctgagtagaa aaccactgtc    26940
gaagggaagc gtctagcctc ccgaaccagg ggcggaaatg ggggcgtgca gggaatggga    27000
gaggaggaag atcgcataac tgaaccttga gaggtgaaga tcggtgtctg aagtaaaggc    27060
ttgcttacga ggccagggtt ctggtttctg ggatgaaggc ttggttttct ggatagcggt    27120
ctctaggcct ggactgcagc atgacagttt ctggggtggt ggccaggcta gaagaaccct    27180
ggtgatgtgg agcttgtcag gcgatggcca gtgaaatact tactctctgg agtagaggcg    27240
tgacatcttc accagattct tggtgtgcag agttaaaggc ttggcttctg gtgtataact    27300
cctcctgtga gataaaggcc tagcttttaa tttctggggc agagttgagc tagacgctgg    27360
ctagtgggat cctgggggcg gggctagtgg cttggaatct ggacctgaga gccctggtgg    27420
ctggggtaaa gatctggtca tctgggcctg gggtggagat gggtcagatg gtgacagtgg    27480
gagtctgagg gcaaaggcc tggtgtctgg gaagaggcac gttttgaaga agtgggtct     27540 ggtgtccagg actggcatct gggccagggc cttggtatct aaggagtctg accatctggg    27600
gcagaaagcg agtggtgatg cggactcatt cctggcccag agccctaatg actgagaagt    27660
ctgatgattt gggttcgatt ttgggtagtt gaattctgag gggtaaaggt ctgggccact    27720
gtcttggtgt cggcatctg gtttggtgcc tgggcatctg gtgacctgac ttccttggtg     27780
ggtggtggga tctaggtaaa agtccggagt ttggacctga gccccagcag tgggatggtg    27840
```

```
ctgcacacag gctctgaggg taggcctctc ttcttcccat tccctggccc tggcaggagg    27900
aagaggacct cccctatgag gaggaaatca tgcggaacca attctctgtc aaatgctggc    27960
ttcgctacat cgagttcaaa cagggcgccc cgaagcccag gctcaatcag ctatacgagc    28020
gggcactcaa gctgctgccc tgcaggtggg aatggctcca gctgccctgc ccaccagccc    28080
ccaccccacc tggtccagtt ataacaaaac tgccaagtgg gtcccgggtc ccgggtgatt    28140
gcttcgtgtt tcatcactga cctgtacatc ccttgatggg tcagcacacc ttctctgatg    28200
tcccagtctg tccctgtcat tgctgagaca tgtcacccct cccacacccc ttcttcccac    28260
atttgccaac tggggcaggg caaatggttc tggggtgtc cataaagctg accgatcagc    28320
atctgtcccc tcctattccc cagctacaaa ctctggtacc gatacctgaa ggcgcgtcgg    28380
gcacaggtga agcatcgctg tgtgaccgac cctgcctatg aagatgtcaa caactgtcat    28440
gagagggcct ttgtgttcat gcacaaggtt tggggctcgg cgagggatg aatcgggaag    28500 tggagctcag tccatggtgg tgggtggggc ggggacaggg gctgggctca gcatgttagg    28560 gatggggct tggattcctg ttgcttcttt gcatgggaag ttgggctgga ctcagtcctg    28620
gagctggggg tttctgggtc ccgccgcatt tatgtggtgg ccccaggtgt ggctcagcca    28680
caggacatcg agtgtctgtg gccaggccat ggagtccgtg gcttagcccc agccgcctct    28740
ccccacaccc ccagatgcct cgtctgtggc tagattactg ccagttcctc atggaccagg    28800
ggcgcgtcac acacacccgc cgcaccttcg accgtgccct ccgggcactg cccatcacgc    28860
agcactctcg aatttggccc ctgtatctgc gcttcctgcg ctcacaccca ctgcctgaga    28920
cagctgtgcg aggctatcgg cgcttcctca aggtgagcct agcaggtgcg ctggttcccc    28980
aggttagttt ccagaaacgg cctcactgtg cactagctc cgtgtaggat gtcacccagc    29040
agacgggatg tgggaagagg ctcctggaga tgcatgtgtt ttgttgttgt ccgtgattca    29100
tgtctttatt ttccaaatag tttgttcaca ctggtttcac attaggcata gcgatgggtg    29160
ctgaggacag tgtgactaag acactccctg cctgcacgga gcttttagtc taactaggaa    29220
gacagatgca tatgagctga tggcatgaac tagagtaaaa ccacagccat gaagagggcc    29280
aggaataagg gtggggagaa gcaggcaggg tggagagtgg aagcaccagc cgggcgggag    29340
tggggcatgg tttgctcaaa cttaaagtat ctgttttatg acgtttggat tctaagctgg    29400
accagtcagg actgaggctg gacccgtggg gcccaggctg gacactatag tcaaggctgg    29460
acccatggga tcaaggctga cccaaggggg ccaaggctag accagtcagg actgaggctg    29520
gactagtgga gccaaggctg gacccattgt gggttggggg tcaattctaa cccaaaagga    29580
ccaaggctgg accattgggg ctgagactgg accaccgcag tcaaggctgt gcccttgcgg    29640
gtcaaggcta acccaaaaag tccacagctg gtctagtcag gactgaggct ggaccagtgg    29700
agccaaggca ggaccacacag ggggttgagc ctaacccagt ggggccaagg ctagaccagt    29760
aggaaccggg ctggaccagt ggggctgagg ctggtttgac agggcttgct tttgcccaag    29820
acactcataa atgggtgggg gggacgcccc cgaagccact gaatcgggag gtgggcgtag    29880
ccctgccacc ccactgactg cctgaggggt ggctcggtcc ccagctgagt cctgagagtg    29940
cagaggagta cattgagtac ctcaagtcaa gtgaccggct ggatgaggcc gcccagcgcc    30000
tggccaccgt ggtgaacgac gagcgttttcg tgtctaaggc cggcaagtcc aactaccagg    30060
tgggcctgcc gggagccggc aactgggtgg gagggccacc ccctccatga ctgagcctga    30120
gactctcccc cactgcccca tgccctgcag ctgtggcacg agctgtgcga cctcatctcc    30180
cagaatccgg acaaggtaca gtccctcaat gtggacgcca tcatccgcgg gggcctcacc    30240
```

| | | | | |
|---|---|---|---|---|
| cgcttcaccg | accagctggg | caagctctgg | tgttctctcg | ccgactacta | catccgcagc | 30300 |
| ggccatttcg | agaaggtgca | tgctggcaca | cggggctctg | ggttcgggc | ggggtctccc | 30360 |
| tccgacactc | ggggacacat | gttgacacat | gcacagacag | aaaacatgcc | atttatggct | 30420 |
| gggtgtggtg | gctcacacct | gtcatcccag | cactttggga | ggccgaggcg | gtaggatcac | 30480 |
| ttgaggtcag | cagttcaaga | ccagcctggc | caacatggtg | aaaccccatc | actactaaaa | 30540 |
| atacaaaaat | tagtcagaca | tggtggtgcg | cgcctgtaat | cccagctact | cgggaggctg | 30600 |
| aggcaggaga | atcgcttgaa | cttgggaggt | ggaggttgcc | gtgagctgcg | atcgcgccac | 30660 |
| ggaagtccag | cctgggtggc | agagcgagac | tccatctcaa | aaaaaaaaaa | aaaaaaaaa | 30720 |
| agtgccattt | ttgacagaca | tgcatatccc | tgcacacgat | tactatcctg | ctgagggtgg | 30780 |
| gggagcactc | ctgcccgcaa | gcacgtcagc | ctttggagtt | cagccacatt | ttgcgttcag | 30840 |
| ggtttcaccc | tcttggctct | gcggccttg | ccccaactaa | gggtggtttg | ttcttttcatt | 30900 |
| tgtaaaaatc | agggtgacag | tttactgcct | tgtcaccaat | cag | | 30943 |

```
<210> SEQ ID NO 5
<211> LENGTH: 64700
<212> TYPE: DNA
<213> ORGANISM: Homo sapiens

<400> SEQUENCE: 5
```

| | | | | | |
|---|---|---|---|---|---|
| gtgcctctag | aggatcccca | tgcacagatt | agaaaggtga | gtcttggccg | ggcagggtgg | 60 |
| ctcgtgcctg | tcatcccagc | gctgtaggac | gccgaggtgg | gtggatcacc | tgccaggagt | 120 |
| ttaagaccat | cctggtcaac | atggcgaaac | ccctctctac | taaaaataca | gaaattagcc | 180 |
| agtcatgatg | gcgggcgcct | gtaatcccag | ctatttgaga | ggctgaggtg | ggagaatcac | 240 |
| ttgaacccag | gaggcggagg | ttgcagtgag | ctgagatcgc | gcactgcact | ccagcctggg | 300 |
| cgacagagtg | attctgtctc | aacaaaataa | ataaataaac | aaacaaacaa | ataaataagg | 360 |
| gtgagtcttg | ggctgcaggg | tatggggcac | caaaatgagg | taccggtccc | caggcacaga | 420 |
| ctcaggatgg | ggaacctggg | gtgagaaggg | agggtgcaga | ctcagagggc | tgccgggaac | 480 |
| tgggctcctt | ctccccgccc | catccctga | cccaaagcct | tttgctccag | caactgggct | 540 |
| ccaggggagc | ccaccagccg | gagccagggc | gaggactgcg | tgatgatgcg | gggctccggt | 600 |
| cgctggaacg | acgccttctg | cgaccgtaag | ctgggcgcct | gggtgtgcga | ccggctggcc | 660 |
| acatgcacgc | cgccagccag | cgaaggttcc | gcggagtcca | tgggacctga | ttcaagacca | 720 |
| gaccctgacg | gccgcctgcc | cacccctct | gcccctctcc | actcttgagc | atggatacag | 780 |
| ccaggcccag | agcaagaccc | tgaagacccc | caaccacggc | ctaaaagcct | ctttgtggct | 840 |
| gaaaggtccc | tgtgacattt | tctgccaccc | aaacggaggc | agctgacaca | tctcccgctc | 900 |
| ctctatggcc | ctgccttccc | aggagtacac | cccaacagca | ccctctccag | atgggagtgc | 960 |
| ccccaacagc | accctctcca | gatgagagta | cacccccaaca | gcaccctctc | cagatgagag | 1020 |
| tacacccccaa | cagcaccctc | tccagatgag | agtacacccc | aacagcaccc | tctccagatg | 1080 |
| cagccccatc | tcctcagcac | cccaggacct | gagtatcccc | agctcaggtg | gtgagtcctc | 1140 |
| ctgtccagcc | tgcatcaata | aaatggggca | gtgatggcct | cccacatttg | tccccttctt | 1200 |
| ggaggcctgg | ctgggtctgg | tctctgggtg | tggcacatgg | gagctgggaa | ttccagagtc | 1260 |
| tgatgcctga | gaccaccttt | gaaagttggg | acatcagatc | tttggccggg | tgtggtggcc | 1320 |
| catgcctgta | attccagcac | tttgggaagt | caaggcaggc | gaatcatctg | aggtcaggag | 1380 |
| ttcaagacca | gcctggccaa | catggcaaaa | cccgtctct | attaaaaata | caaaaattca | 1440 |

-continued

```
gccgggcacg gtggctcacg cctgtaatcc cagcactttg ggaggccaag gcaggcggat      1500
cacaaggtca ggagatcgag accatcctgg ctaacacggt gaaactccgt ctctactaaa      1560
aatacaaaaa attagccggg cgtggcggcg tgtgcctgta gtcccagctg ctggggaggc      1620
tgaggcagga gaatggcgtg aacccggag gtggagcttg cagtgagccg agattgcgcc       1680
actgcactcc agcctgggcg acagagcgag actccatctc aaaaaaaaaa aaaaaacaaa      1740
aacacaaaaa ttcgctgggc gtggtggtgc acaccgtaa tcctagctac tcaggaggct       1800
gaggcaggag aagtgcttga acctgggagg tggaggttgc aatgatctga gatcacgcca      1860
ctgtgacaga gcgagacccc aactaaataa atttaaaaag aaagaaagaa aattgggagc      1920
aagcagatgt ggtggctcat gcctgtaatc ccagcacttt gggaggctga attgagccga      1980
tcacttgaga ccaggagttc gagaccagcc tggccaacat agtgaaaccc cgtctctact      2040
aaaaaaaaaa tacaaaaatt agccaggcac ggtggcatgt gcctataatc ccagctactc      2100
gggaggctga ggcaggagaa tcacttgaac ctgggaggca gaggttgcag tgagccagga     2160
tcgtgctact gcactccagc ctgggtaaca gagtgagatt gcatgtcaaa aaaaaaaaa       2220 agaagaaaaa agaaacaaat tgaggagcaa ctgaagtaga attcgatctc ccgttttat      2280 tttttcctgc tctatgacac ggagaatgtg caggacatga agcctctgag gtccaatggc      2340
cccttggaat actgtagggg aaggcggtgg atcaccctga ggccgggagg gcgtgagttg      2400
actcatggaa gtacccagag cagggcttag tacacagaag gcactcagta agtgctggct      2460
ggctggacag gctgatgggg agtgggcccg gtcaaccgga ggccatttcg ggtctggagg     2520
tgttaaccct actcagggtc tgggaggctg aggtggcacc agcctcacgc tcggccaagg      2580
tcgacccatg ccggaggcca cgggagggag gccaggagca cagggtcccc tctccacact      2640
cctctaccag tggctcaggc caacactggg gtcattgcac ctcttccctt tccctgaca      2700 acacctccag gtccaagacc ataagaaatg ccagtgggct ctgctgtcaa acggcgctca      2760
caatcactca ctgctcaccc cttctgccac tgcctcgact ggagcagtca cctccgcccg      2820
gggctctctc ttcactgccc cctttccaga gtttcctcc agctcagata aaaggccaaa       2880
gccagctgcg cacagtggct catgcctgtc atcccagcgc tttgggaggc tgaggtggga      2940
ggactgcttg agttcaggag tttgaggcca gcctgggcaa catagtgagg ccccatctct      3000
acaaaaaata caaaaactag aggtgtagtg atgggcaact tggtcccagc tgcttgggag      3060
gccgaggtgg gaggattgtg cccctgctct cagcctgggc gacagtgaga acctgtctca      3120
aaaaaaaaga agaagaaaag agaaaaagcc agccaggtgc ggtggctcac gcctgtaatc     3180
ctagcacttt gggaggccaa ggcgggcaga tcacttgagg tcaggagttc cagaccagcc     3240
tggccaacat ggtgaaaccc cgtctccact aaaaatacaa aaattagctg ggtgtggtgg      3300
cggatgccta tagtcccaac tattcaggag gctgaagcag gagaattgct tgaacccagg     3360
aggctgagat ctgagatcgc accactgcac tccagcctgg gcgacagagt gagactccat     3420
ctctaaataa taataataat aataattaat ctgtgtgacc atgggcacat gacttctttt     3480
ggaacctgcc tgtgaaatga gctgatgctg cttgcccagc tcaccaaggg ctggtgcctg     3540
gctcctcctc ctcctcttcc tctcacccac ccacctggag ggtccagggg aagaccttcc    3600
ttgcagccca gagcaccgta agttagagct gctgtgatca gaagctgccg aaccacaggc      3660
tcttctttct cttcatcctc ccttgcccca accccgggcc cagcctcata accctacagc      3720
ttgttcaaac gttttccctt ctcctcaagc ccctaactc accctcggtg gccggtgggg      3780
atggggcgtg ggaacagacc ctgggccctg cactcccagc ttacaaattc ccgcagcccc     3840
```

```
tcttcctccc tcccgatttc tctgacatcc ctcacagccc cgcctctgga cagaagaatg    3900
gccctgccc  tggccggccc tggaagcccc tctcgccagg gtctcagagg acctgcctgg    3960
ggctgcttag cccaaagcgt cctgcatttt gctctgaaat ccagcttctc agacaccatg    4020
ttccctccc  tccgtccccc atccaggact gtggtttctg tgtctgtgca gacgcccaga    4080
cctccctcca gaactccaga ccccaaaccc caagacctgt gcatctgctg gcccctaga    4140
cgcctccccc tcattccaga ttcaggctat catcctgccc aagccctctc ccggcgcctc    4200
cctccacctc aacagccaa  cagctattcc aggatcagcc ctggggctat gtgtggtggt    4260
tgctcaatgg tttcattcat cctagagacg ccaccttctc cccagtgtgc tgaagcccac    4320
cctgctcaat gcctcttgct aggatggctg agactgccct gaccaagccc tcagccctgg    4380
tccaccaggc agtccaacag agcatcctaa acaaatctag aggtgacacc gacccctttg    4440
gcccttctca taaccagtga ggggagccca gctgacagtc cctgcagttc cttttctgaa    4500
cagacctgtc tgttcacatt ctgggggcg  gtggaaagga agcagggaag attggatcat    4560
ggttccccca aaaatctgg  aagaactttc cttggggggag aggaggagtt atcaggaacc    4620
aagtgtggtg aacaaaaagg gaaaggaaaa ttgcctgagg tgtaatacat tactttttt     4680
ttcttttta  agacagggtc tcactctgtt gctcaggctg gagtgccagt ggtgtgatct    4740
tggctcactt caacctccgc ctcccaggtt taagtgatcc tcctgcctta gcctcccaag    4800
tagctgggat tacaggtgcc tgccaccacg cccagctaat ttttgtattt ttagtaaaga    4860
tgggttttgc catgttgacc aggttggtct caaacttccg gcctcaagtg atctgcccac    4920
ctcggcctct caaagtgctg ggattacaga cataagtcgc cacgcctggc cttatttcaa    4980
attcttttag acaaggtctc actatgttgc ccaggctgga caccaacccc tggcctcaag    5040
cgatccttct gcctcggcct cctgaatagc tgggactcca ggtgtgcacc actgcacccc    5100
acttatttta aaattttttt aacaagggaa atgtgtttgt atcatcctgg actttaaaat    5160
taactttaaa gtattgacca gactggccaa cacagtgaaa cctcatctct actaaaaata    5220
caaaaaatta ggtagctggg actacaggaa tgcacctcca tgcccagcta attttttgtat   5280
ttttagtaga gacagggttt caccatattg gccaggctgg ctcgaactcc tgacctcgtg    5340
atccgcctgc ctcggcctcc caaagtgctg ggattatagg cgtgagccac gcgcctgac    5400
cttttttgttt tttagatgga gttcgctct  tgttgcccag gctggagtgc aatggtgcaa    5460
tctcggctca ctgcaaccctc cacctcccgg gttggagcga ttctcctgcc tcagcctccc    5520
aagtagctgg gattacaggc atgtgccacc acacccggct aatgttttct attttagta    5580
gagacggggt tttgccatgt tagccaggct ggtctcgaac tcctgacttc aggtgatcca    5640
cctgcctcag cctcccaaag tgctgggatt acaggcgtga ccaccgcac  gtggcccctc    5700
ctggtgattc tgatacccta aagcctgcat ctcaatctaa ggtccccagg aatcccctgg    5760
gggcctcgct aaaatgcacc ctcagattca gcagctctgg ggtgggcctg agactgcatt    5820
atggaccaac tcccagttga tgctgctact gctgatctac agaacacact ttgatttggc    5880
tcacgcctgt aaccccagca cttacggagg ccaaggtgga aggattgctt gaggccaaga    5940
gtttgagacc agcctgggca acctaataag agccccatc  tctacaaaaa ttttttaaaa    6000
attagctggg catggctggg cgccatggct cacgcctgta atcccagcac tttgggaagc    6060
cgaggtgggc agatcacgag gtgaggagat cgagaccatc ctggctaaca tggtgaaacc    6120
ccgtctctac taaaaatacg aaaaattagc caggtgtggt ggtgggcacc tgtagttcca    6180
gctactcggg aggctgggc  aggagaatga catgaacccg ggaggcggag cttgcagtga    6240
```

```
gccgaagccg agatgctgcc actgcactcc agcctgggcg acagaacaaa accctgtctc    6300
tgaaaaatat aataaatgag ggaagaaggc aaacaatctc cctctgcctg ttttctaggc    6360
acacggtgac acccactcct ttacatgttg tctgtggttg cattcagtac atcagcggag    6420
taatggggca agagcacatg gcggcacagc agtggctcac gcctgtaatc ccagcacttt    6480
gggaggctga agtgggcgga tcacctgaga tgaggagttc gagaccagcc tgaccaacat    6540
ggtgaaaccc catctctact aaaaatacaa aaattagccg ggtgtggtgg gaggcacctg    6600
taatcccagc tacttgggaa gctgaggcag gagaatcacg tgaacccaag gtggaggttt    6660
gcagtgaggt gagatggtgc cactgcactc cagcctgggc gacagagcaa gactctatct    6720
caacaaataa aaaaaataat aataaagacc acatggcata aaatattgcc catctggcac    6780
tttgcgcagt ttgcccaccc ccagtctaaa ggcgtctgtc tcagcctgat gcgtctccca    6840
ggaccccatg cccccctccag cctgcagaca gcctccaacc gtgattccag aacctgccag    6900
catttcccac caactccttt tgccgggttt atttctcccc accactcctg gtctcactca    6960
accccccaac cctatggcca gacccgcccc cactctactg taaacacatt cggacctggc    7020
ctccctcccc agcctggggc agggctgtgg ctcaaggtac tgagtggatc taaggccgcc    7080
acacaagaca caagacacac gtggggaggg gctctctgta tcctttatct ccggcagggt    7140
cagcggccct ccagggcccg gtctcgagcg atgactgcct cctcgaactt gatcatgagc    7200
gtggtgccct tgtgccagtg cgccgtgacc ttggcaggga agccgctgtg tgtgagcacc    7260
gcctccacga tgcccgccgt gaagctggcg cagttgagcg tgctgttctc cttgggcacg    7320
gagatgtagg tgttgatgag cggctcgcgc tcgatgatgt agaaggtgcg cgcgtcatcg    7380
ttggcctgct ccagcttgtc cgcctccttg ccgaagagcg ccttccacac ggcgcccttg    7440
acgaagagca acgcgcctag cacccttggtc tcacgccggg cacccttttc gcgcgccacc    7500
agcgcatcca gcacgcgcgc gcccacctgg cggcccagcg cggccaggcg cgactgcagc    7560
tcggccacgg agaagacgcg gctctggcag tgctgtacca gctcggagaa cagcagtgcg    7620
aaggcgctca ggctcacctc ggtgcgcggc cgcgccagcg cgcgctccag cagcgccgac    7680
ttcccgcgcg tgaagcgcgc ctccatgccg ccgcccaccct gcggggagac caggaagtgc    7740
aggtgtcagg ggcaatggga aggggagcag gccgggagga aaggagggag aaccgcgagg    7800
ggccctggga caccctcgac ccatgccact gttgtgtgct ccagtgccga cttcccactt    7860
gcaaagagat gcgcgtaaaa cacgcctcga ttacacgtaa ccagataaat caagggaggg    7920
gggagtctta taccctcggc aggcagcggg ctagcgggga tggggacaag gtgggaggag    7980
agacacgagg gggaacagaa gaggaggccg aaaccaccca accctcgggc atgcagacgg    8040
ttcaattgcg aaagcgcctt cctgcccgct ccgccaccta caggagtaac tagaaaacta    8100
gtgtatgggg ggaggggcgt cagatctagg gcagggaggt gacaaagatg aggcaccacg    8160
aggggatatg ggcagtcgct cctgccccgc cctgcgctcc agcacagacg accctcggga    8220
actttcctgc cggccccctg cggaaagcca gagtaaaggg ggtggagggt gggagtgggg    8280
taggagcgtg tcaagaccaa aagccaggag ggttgggggc tttaacaggg gggatccgtg    8340
gggccaggca ggagggggcgg gtaacccca accccaagcc ctcaggcagg cagctccgat    8400
gtgtcacgca ggaacccttc gtcctttgag acgcggatgg gcctgggttc tgaaggctgg    8460
gaggaggggc ccagaggtgt tgggagcctc ccaccccgt gctctccaga aaggaagctg    8520
gatgctgagc aactgtggtc ctcccatcag ctgtcggtgc ggggagaggg agatggggta    8580
gggggctcct gaagagaaat ggggtgggga gcgggcgccg agacgggatc ggaggggcag    8640
```

```
ctgagaaccc gcccccacca tgcatgggga ggtgtgtgga tgctaagccg accccaacga    8700
ggtctgcgtg ggaggtggga gaaccagcgg ggaggggtgt cccagggggct ccgggccgcc    8760 cccgccccag catgcagatc cgtccgtggc gagggccctg ggcgcgcgag atgggagagg    8820
gatcgttaag accccaccac cgggctgcga tgggggctga agtgagctga actgccgtag    8880
ggtcagggcc ccgcgaccct cgccccgtac ctctacactg gggagaaacc caccctcctc    8940
gcagcctcct gagggggggcc gaagcgagcg ggctcgggat cgcggacgcc gagacccag    9000 cccgggaccc acacgcccgc ggggaagggg ccggggagcg gacgaggccc ggcgcgggca    9060 gggggggtggg tagggtctca ccaggaaccg cagcagtctg ctcggccgag ctgctttacg    9120
gcgccgtaaa aggcgctgcg tgcgcaggcg ctcgacgggc caggcgtgtg ggcggggcgc    9180
gcgcagcggt gcctgagagc ggccgcaggg gggcgcgcga gtccgcggag ccggacccag    9240
ggacgtggcc cacggccgtg atggctgctc cgcgcgtggc cagggtctcg ctggctctgg    9300
gtggcccacg ctggagggga cgcttgcagg cctagtcacc tgctcagggc gcacgtatga    9360
caatgggcca atgtataccc ttgcacatgg acacacctgt tggcttttcc aggcactcct    9420
atgtccttgg ggatgggttc aattgtctca agtgcatcca tgtggcccgc ggtggctccc    9480
gcctgtaacc ccagcatttt cggaggcgga ggtgggagaa tcacttgagg ccaggagttt    9540
gagaccagcc tggacaacat agctagactc ccacttcttt aaaaaaaatt agccaggtgt    9600
ggtggtgtga acctgtaatc ccatctactc gggaggcgga ggcaagagga tcgcctgagc    9660
ccaggaggtc gaggctgcaa tgagtcatga tcgtaccact gccctccagc ctgggtgata    9720
gagcgagacc ctgtctcaaa aaaacaaaaa caaacaacaa caacaacaaa tcaagtgcat    9780
gcatgagcgg tggacatagt accttagggt catgtacact catggataca tgctcaatgg    9840
catagataca ctcacgggca caattacaca cgtgggtaca cgcttagggc ttgtatatat    9900
ccgtggtccc aggtacactc agggagatgt tgtatgctca ggggcaccca ctctgggaca    9960
cagggaagac acagggaatg agttactcat tcacagatgc acaggtactc acgcagggca    10020
ctcagtctcg cccaccctgg tgccccgggg tcattgtcac gtgcagactc tccctctccc    10080
caggtcccaa aaccccctccc cttgcccccag taacaggtcc catagcgacg ctgttttccc    10140
ttgactttat ttatcttcat aagtcacaaa atgtgagtgc agagataaat gtctgtgtgc    10200
atgtgccctg agcacacagg gtggcataac tcggcacact cataatgaca cagccgttca    10260
cccagccaca gatagtgaca gggcacacat ggcgacaccc acatgtacgg agataaatct    10320
cccccaccat gacatgggta gacagaaaac acgccgcagt atactctagt atgtttacac    10380
aaacagggag acaggcccgt gcaatgcatg tcaccaacac ccacactcag agtgacatct    10440
gctggaggtg ctcagacaca gccacccacc gtgacatgcc gagactcaca tatgtcacat    10500
gacacaggca tgcatgccac attcactgtg actctcagtc ctattcattc atcacctttc    10560
tgggagatac actgaaatgt ccacccttttg caaaatgcac acacacgcgc acgcacacac    10620
gcacatacac gaacacacgc gcacacacgc acacacacgc acgcaggtgt acacacacac    10680
gagcaactcc gagacactca ttcaccatga ctcgaggttt ttctatacgt gggacgaggg    10740
gcaggttcac actaggctgg ggggggggggg tcatttcccg tcttcgttgg caggtgcagc    10800
cccatcttcc aagttgtggc tttggctgcc acaatgtcct ctcatttatt gaggtgagga    10860
ctctggggat ggggagagac ccacagtgag gcagatcccg cccctgggag aggagctggg    10920
gctaaatctg aagccccacc caccctcctc cacctcctgt cggggcgcca acttacgtgg    10980 catttttctgc agcacctcca agattttctg tacctttgtg tcaatgtttt ttatgcctag    11040
```

```
ggggcgggga gggttgggtg ggaacagata agtcaagctg cggtggagcc tcaaacaaag   11100 ccccacctt ccttggaagc accccccctg ccccacaccc accctggggt acagcagagc    11160
ccatggattt ggggttccca ggagcctttc aatacccaca gagcaaccca gatggtaaca   11220
cccatcgccc ctccacaact tgagctttgg gagggtagga ccccggcttt ctcctcccct   11280
gaatcccctg cccccagctc agctccgggc attggtgaca aataacccce atagaaggcg   11340 agactacaca ggcacctgct aatgtcgtct ctaatctatc aatcttgctc ctgaccatgg   11400
tgatgctctg ctgaacggaa tcccagcctc tcttctgtct ctcttcgcat gcttgtacgg   11460
agtttgagac tgagggcatg aaacagggt gtctgtgcat ccatccctct ccagaccccc    11520
accatgaccc cacgggtctc cctcagaccc tccgctcacc attccaaagc tccctttaa    11580 agcccagcag ctccttggac atctcagcat ctgttcagga ggggcaggaa aatccttgaa   11640
gcacccaggg agagagagag agaaggacaa gggagaaagt ctaggccccc cagcacccte   11700 ctcccaagaa gtactcactc ttcaccatga tgaaggctga caggatgatg cagaggacaa   11760
aggccagggc caggaggatg tacaggctca ggatggctct gtacaaccag caggggacct   11820
gggtggagtc tgagggcggc ctgcactggg ctgggactgg agcaaagagg cagcaaagtg   11880
accttgaggg gccagcacca ccactcaaac catcctcact gtctctaaca ccatggacac   11940
ctcgctcctc tcaaaaccat cagcagctgt ggtcatgcag cttgtcatca tcgtcaacaa   12000
cactgccacc accagccacc ctcagcgatc taacaccgtc accatcacag accccctctc   12060
cagcattccc caacattgtc atcatcaaca gacctcatta gcacgtcaac agctgtcacc   12120
tcttccttcc ccatcgcttc ctcccttcca cgcagccccg ggggccctgc agttgcccgc   12180
ccacctgccc cttcccaagg tgatgggatg tgagcaggtg ggtgtctgct caccttggct   12240
cgtgggtcgt gaatgaccac cctttgcatg gtcctgattt ttgaaggcca aggtgatatt   12300
ctcatagtct gggtcatggg cacctgggag gggttggaga tctgctcaga gctctgtggt   12360
gtggagagtg gatccgggat cttgttttac ccaacccttt gcactcaata aattgtaggg   12420
ggtgaaagat aaggagtgag aagctaaaat ctgcttttg gttaagtgga gcgggtgtgt    12480
gagagtttga gtgatcacac cacacacaca tccacacaca catccacaca tcttggaggg   12540
gaaggagccc ccggccccca cctttgaccc cttacctctc ccatctgaac tctccttctt   12600
tttttatttt tatttttac agacagagtc tccctatgtt gcccaggcca gtctccacct   12660
ccagggctca cgcaatcctc ccgcctcagc ctcccaaagt gctaggatta cagacatgag   12720
caaaagcccc cggcccccca atctctcctt cttaacccct cccttccacc tcgagttccc   12780
taaccttgat tcttggctga ccccctgt ttcttgtccc tgaaggctgg tgcttgcatc    12840
ttgacttcct ggtgcttgta gatttcctcc acttccatgg tccccagccc gcaaatttgt   12900
ccatacacgt ccccgcccac cggaaggtgt gggcagatga ggaaatctgg aggtgggggg   12960
aagaaagagg gggagcagcc tcctcttttc agggatccac gactctcgca ccctgggca    13020 ccctcattcc tgccccgatc aagaggctct tgggagccaa gaggtctcag gaaggaccaa   13080
gaagaaaaac ctctagaccg ggagatggaa ttcgacactc ggaaatgtta caggaagctg   13140
tggtctctgt gtgtgtctgt gtctacctgg atggacctca ccctcctacc tcctctccat   13200
ttcaaaagag aagctgtgac acctcagtgt cccaactttt cgcgtaagag caaccaggct   13260
tggagacagg accctgggt cccccacac cttcctcct ccagcctcag ctccacccct      13320
cagctccacc cccaagaagt tcttctactt ctacaagtcc ccgtggagga aaagcacaga   13380
tgtgaggcaa cgggaactaa ccactggaac gccacaccca catctgggac tgaggacaga   13440
```

```
cccacatcct tccctccctc cccaaatccc ctgcttttat acaaccctgg aggaggctgg   13500
gtgcggtggc tcacgcctgt aatcccagca ctctgggagg ctgaggtggg tggatcatct   13560
gaggtcagga gtttgaaacc agcctggcta acatggtgaa accccgtctc tactaaaaat   13620
acaaaaatta gctgggcgtg gtggcgagcg cctgtaatcc tagctactca ggaggctgag   13680
gcaggagaat cgcttaaacc tgggaggcgg aggctgcagt gagcggagat cacaccattg   13740
cactccagaa tgggtgacaa gagggaaact ctgtctcaaa aaagaaccct ggaggaacag   13800
tttcctctgc acctggaaac tccaggtttc tcattctcat ccatccatct gcttatctac   13860
ccagatactc tctctcacac atgtacacac acaggtctgc acacggacac acatcacaaa   13920
ctcatttgca tactatttgc attgtgacac tcagaaaaat agacacaagc atgcgttcac   13980
atgcccgcac tctgtctaga aggtgtctta gttcactttg tgtttatctg atcttgaaaa   14040
ctggggttac aaaaggcaca aagtagctgg gtatggtggc tcgctctgta gtcccagcta   14100
cccaggaggc tgaggtagga ggatcatttg aggccaggag tttgagacca gcgtgagcaa   14160
catagcaaga ccctgtctct ttaaatgttt tttaataatt ttttttttgag acagggtttc   14220 actctgttgc ccaggccggg gtgcagcagc gtgatcatgg ctcactgcag cttttgacctc   14280 cctggctcaa gtaatccttc gtcctcggct tcccgagtag ctgaaattac aggtgggcac   14340
gacttcacct ggctaatttt tctccttttt tgagatggag ttttgtgctt gtcacccagg   14400
ctggagtgca atgacgctat ctcagctcac tgcaacctcc gcatcccagg ttcaagtcat   14460
tctcctgcct cagcctccca gtagctggga ttacaggca tgcaccacca ccccggcta   14520 attttgtatt tttagtagag acggggtttc cccatgttgg tcaggctggt ctcgaactcc   14580
tgacttcacg tgatctaccc gccttggcct cccaaagtgc tgggattaca agcatcagcc   14640
accgtggccc agtctaattt tcttatttt ttgtagagat gagggtctca atatgccgtc   14700
caggctggtc ttgatctcct ggggttcaact gatcctccag ccttggtctc ccaaagtgct   14760
gggattacag gcatacattt ttattttat tttttctgg ccaggtgtgg tggctcacgc   14820
ctgtaatcac agcactttgg gagtctgagg cgggcggatc acctgaggtc aggagttaga   14880
gacaccagcc tgaccaatat gataaaaccc tgtctctact aaaaatgcaa aaattaactg   14940
ggcgtggtgg caggcgcctg taatctcagc cactcgggag gctgagacag gagaatcact   15000
tgaacccggg aggtggaggt tgcagtgagc cgagatcgcg ccattgcact ccagcctggg   15060
caacaagagc aaaactccgt caaaaaaaaa aaaaaaaaa gaaaaagaa gaaagaagaa   15120 agaaggaagg aaggaagaag aaaagaagaa aaaacaagta taagactgtc ttatgtgcag   15180
aaagtgatga tgttttggtt aaaaatatgt ggttaaattt cagacaactt gaatgttgag   15240
aaatgagcgt cgagatctgg tgaggataaa gttctgtttc ctaaaatatt gccaaatcct   15300
gtgtctccaa gaaagatcaa tttgataatg acttcatgcc agctgctcca tttggtctta   15360
gaaagaagtc agttactgag ctataggacc gccttctaat ggagcagacg gaccaattgg   15420
atgtgggctc tgccttgatg acaggcaca ggggtggag ccacagcgtt gcacatttcc   15480
cgggcttggg tggggctgag acgcggctcc aggctctgga cttcctttga gaaaaaggtc   15540
acgctaaacc agaggcccac aagcaatcat gtcatgtggg aaacatctgc aaagctgcct   15600
gaccagcacc cgtccctttc atagggtaac attctcaatt ttcttttaag aaagaaaatg   15660
tgtgctagat ccagcaaacc ataagctagg gattggttta cagtggacaa atgatccaga   15720
cccagccaac cagagtctaa gattgggcag agaggcgggc attttgagcaa gatccagcca   15780 atgaaacgct ggtctgggat ttttattggt ttaaccacgg gggaaaaagc attctctttt   15840
```

| | | | | | |
|---|---|---|---|---|---|
| ttttccagcc | ctcactaggg | ctgccacaat | gggaggatgt | aatgggagct | gtgacaggga | 15900 |
| agaatttact | tgagagcaaa | ggcagtgctg | agaaaatcag | acccgagagg | aagtctgggt | 15960 |
| cctggagaca | tcatttgaga | ccctggttcc | aagccatacc | tgaacctgtt | gttctaaccc | 16020 |
| tgggcttgtc | agttacacaa | acaagaaact | tccttttagt | tttgcccaag | ctagtttgaa | 16080 |
| gtggggtctg | ttgtacttgc | aagcagaaga | atcttgcctt | ggctggtctc | tgtggcccac | 16140 |
| gcctgtaatc | ccagcacttt | ggaaggccga | ggcaggtgaa | tcacttaagg | tcaggaatttt | 16200 |
| gagaccagcc | tggccaaaat | ggcgaaatcc | ccgtgtctac | taaaaataca | aaaattagcc | 16260 |
| aggagtggtg | gtgggcgcct | gcaatcccaa | ctactcagga | ggctgaagca | ggagaatcac | 16320 |
| ttgaacctgg | aggtggaggt | tgcagtgagc | tgagatcgtg | ccactgcact | ccagcctgga | 16380 |
| caacagagtg | agactccatc | tcaaaaagga | agaagaagaa | ggaggaggag | gagaaggatg | 16440 |
| aggaggagga | aggagggagt | gaggagggag | gagggaggag | gatatcttgc | ctaccacagg | 16500 |
| ggatctaggc | attagctatt | gaggaaattg | aggctctaat | aggggttttg | cctgtccaca | 16560 |
| tcacctgggc | agatatgacc | tccaagtctg | cactctgggg | caggagaatg | tctatgttgg | 16620 |
| aattgaggaa | cctgaagaga | gccctcttag | gtttcagata | caggactatt | ggatgggggt | 16680 |
| ggagacaaat | agttctgggg | acaatggagc | atccccgccc | ccaacacaca | cacacagcag | 16740 |
| taagggcag | ggacacacac | aaggcactag | actcaccctc | tctggccctg | gccatgcttc | 16800 |
| taactcagtg | gtcctgccct | accccatga | ccactgtgga | gtcaggagag | agggtctggg | 16860 |
| aagggaatcc | ctgggctgga | gtctgggtgg | ggtccctggc | accagaagtg | gttgtaatct | 16920 |
| ctgctcatgg | ccaccagcat | cagacagggg | gctgggacca | tcacaggggg | tgggtggcag | 16980 |
| tgggaggaga | gtccaaaaca | tcctgcaaac | cagaacctca | ctctatcatc | tgttgtccag | 17040 |
| gtgtgacatt | tgagtctggg | atcccctttca | agactaggtg | ctaggaattc | tgaagtctgt | 17100 |
| ggtgggaaat | cagggactgg | atggcaagac | tcctgggtca | ggcttcctgt | agaactggac | 17160 |
| cccgaatcac | ctgaatttgt | gccccaggga | gctgaggcgg | gggatgctga | ggcttttgcc | 17220 |
| cactagaaca | ggggtcccca | gccaccgggc | attgggaacg | gggcctcaca | gcaggaggtg | 17280 |
| agtggtgggc | gagcgagaga | agcttcatct | gtatttacag | ccactcccca | tcattcgcat | 17340 |
| taccacctga | gctccacctc | ctgtcagacc | agcagcagca | ttagattctc | ataggagcaa | 17400 |
| gaatcccatc | gtgaactgcg | catttgaggg | atgtagcttt | ctcacttctt | ataagaatca | 17460 |
| aatgcctggt | aatctgtcgc | tgtctcccat | caccctcagc | tgggaccatc | tagttgcagg | 17520 |
| aacacaagct | cagggctccc | accgattcca | cattgtggtg | agttgtagaa | ttattttatt | 17580 |
| ctatattaca | atgtcataat | aataaaaata | aagtgaataa | taaatgtaat | gcgcttgaat | 17640 |
| cacccagaaa | ccatccccgc | tccccccta | ccccatacac | acaccaactg | tcttccatga | 17700 |
| aaacagtctc | tggtgccaaa | aaggttgggg | atcgctgcac | tagggtatca | gatacttatc | 17760 |
| caggtgcagt | ggggactaga | gtcagaaatg | caagagtctg | cctggagcat | gtgtgtgttt | 17820 |
| gtgtcctgca | tcatctctgc | ccaccatagt | caaatctgcg | attctccgtg | cattggccgg | 17880 |
| gggggtggtg | ccttttctgtg | tccaagagtg | tctaggggca | catgggtgtg | tctgtggatg | 17940 |
| tggtgtctcc | atgtggccgt | ggtaggtggg | ttgtgtactc | tgtgtgtgca | cgtggctgtg | 18000 |
| tatagctgtg | tgtgcatgtg | cagtatgtgc | acgtcggtgc | tgtatctaag | tgcacatgtg | 18060 |
| gctactgatc | aacagacatt | tactgaacgt | ctactgtgtt | ccatgctcta | ttctaaaccc | 18120 |
| tgggggcgct | gggtgcagtg | gctcatgcct | gtaatcccag | cactttggaa | ggccgaggtg | 18180 |
| ggtggatcac | ctgaggtcag | gagtttgaga | ctagcctggc | caacatggtg | aaaccccgctc | 18240 |

```
tctactaaaa atacaaatta gctgggcatg gtggtgggca cctgtaatct cagctacttg    18300
agaggctaag gcaggaatat cacttgaacc caggaggcag aggttgcagt gagccgagat    18360
tgtgccactg cactccagcc tgggcgccag agtaagacct tgtctcgaaa ataaaaatta    18420
aaaaataggc caggcgcggt ggctcatgca tgtaatccca gcactttggg aggctgaggc    18480
gggtgaatcg cttgaggcca ggagctcaag accaacctag ccaacatggt gaaactcctt    18540
ctctactaaa aatacaaaaa ttagccaggt atggtggcga cgcctgtag tcccagctac    18600 gtgggaggct gaggcaggag aatcgcttga acccaggagg cagaggttgc ggtgagccga    18660
gattgcacca ctgcactcca gcctgggcaa cagagcgaga ccctgtctca aaaaaaaaaa    18720
aagaaagaaa gaaagaaaag agaagagggg agaggagggg aggggagggg aggggagggg    18780
aggggagggg aagggaaggg aagaaacgaa accctggggg ggatctagga gcagacaagt    18840
cccctgctct gtgttttcat aatctagtat ccaggaaggg gtaagcaccc tgcgtgtatc    18900
tggttgtaac taactactca caactgcact gcctgtgtg aaaacgtgag cttgtgatga    18960
tgcgtgacgt caggtaggcg tccctgactc tccgtaaccc aactttgcct gtgccttggg    19020
gattcctcct tgcaggtagg aagtgagggg tacaggttcc agctctgggc tgagacatga    19080
ttcagggttc caccctgacc tggggctcct ggagtcttgg ggccctggag ggtcccgtcc    19140
actgcccaga ctgacccagg tcctcgatga agcctcatta tgaggactgg gggaaaagga    19200
cccagccact tcctggggag gtcggagacc ccagggtgag cgtcaaggta gcctcaaaga    19260
tgagacgtca cctcttgaag gcagccatga gccttgggtg gggacgtcac tagaggaagt    19320
tcaggcccta ttttcggagg aagcagttgg agaccccata ggaggaaggg cgatgggca    19380 gtagaaagtc gcggtgtccc cgcccctcc agcagctacg cgccccactc tcttggagac    19440
gctagatcag tccctccggg cctactaaag aaaccacgca gggctcagat ccgctccatc    19500
atcatcatca tcatcatcat catcatctcc aggtttattt ccagctcccc cgcaaccct    19560 ccggacctgg agccgcctcc gcccgcgctg tgcacgcgct cgcgcgacc tcagggctgc    19620 acacgacagc agcgcgctcc ggtccagtcc atgcccgcgc actggcagtg acatgtggtc    19680
tcggcgcgca catcccacga gccacaggcg gagccacaag tgcagccggt gacggcgaag    19740
cctgcagccc ggaacacagg agcgtggact ctgagctggg aggctgaggg tgggagcggg    19800
aggggggtgg ggagcgcgga ggggggttgg ggggcgggg gtggggacgg ggacggctgg    19860
aggctccaac cactgaatgg gcactggagg cagggagtga gggtggacac cagtgtccag    19920
atggtgggcg gagaaggctg ggagtcagga ccaagatcct aggggagtag aggctggaca    19980
cggggaacgt ggcggggagg gggcattccc aggggacttg gaacagaaat gggcgcctgg    20040
acaacagtct cctgcactca cctcggggc aagtagccag gtccccctg gaggtgacgc    20100 tctggcactc caggccaatg ctgcttattg ccctaaatac tgggggcag gaggaaagga    20160 gacaggggga gctgtgagac caaacggtcc ctcccccatc ctcccctagc cctgttggtt    20220
tggagctagg tccctgtggg cataggagct cactggcctc caggaccctg tcttgagttg    20280
ggtgttttgg agtaagggaa ggtttggagt gagagcgggg attgggtttg gagccgtgga    20340
taaggtgggg acagtcggag gggttgggag tggagttggg gttgaattta tgatctggtt    20400
ggatttgagg atgagatttg gtgagcgctg gggctgggtt ggagtcaggt ctgtgccagg    20460
gatcagtgag gtctctgaga cccttgggga gcttgcccaa gtgggggtc ctcacttagg    20520 gagccggcga cctcctggat cctctcattg atggcttctt ccatggagca cagggtcttg    20580
ctagacacca acagccccag gacagggagg aggaggagac agagagcttt catcctgcag    20640
```

```
gcgctgaaag agggaaccaa gagacccaca gctggatcag ccctgccctg tggggaagat    20700
ccggcccatg gagggagtag gatctgcccc tggacctgga cccctgtccc ccatgtgggg    20760
ggacagggat ggaggctcag ccttgacccc agcctccccg ctggtgccat ggcaagcgca    20820
ggagcagctg tcacttaccc tctcggtggg ctcagctaac caaatccggc acacgaattc    20880
ctgcaccgca gctctttctt tgaggcctct tggggtgggg cttcctggct tggctaataa    20940
gtccctgggc ccccaacccct ccggtcccac atccggggcc aagaggaagc ccctgagcag   21000
acagtaaggg ctggaggagg aagggagcct tcccacttcc aacagggcct ccgtcttcat    21060
gtccagagac tggtcaggag gtggtgcccc agggataatg ccaggggctg tggtctgagg    21120
aacaggtaga caagcagagt tttgcatgca agggtggctg atgcaaacat gacaaaatta    21180
atgcctcttg ctaggcatgg tgcggacaag cacttgtagt cccagctact aaggaggctg    21240
acgtgagaga attgcttgag cccgggagtt cgaagctaca gtgacttatg atcacagcac    21300
tgcactccag tctgggcaac agagcaagac cacttctcta aaatagtaat aataattatg    21360
tctctgggtg agaatgacat accacattca tacccaaatg cccatgagca atagaactgg    21420
taaataaaat catggtttat ggccggtggc tcacgcctgt aatcccagca ctttgggagg    21480
ccaaggcggg cggatcactt gaggtcagga gcttgagacc aacctggcca acatgatgaa    21540
accctgtctc cattagacat acaaaaatta actgggcgtg gtggcgtgtg cctgtaatcc    21600
cagctacttg ggaggctgag gtgggagaat cacttgaacc cgggatgtgg aggttgcagt    21660
gcactgagat cgtgccccctg cactccatcc tggatgacta gcttgggcac catagcaaga   21720
ctccatctca aaaagaagaa agaaaaatca tggtttattc catcaatggc atcacctgca    21780
acagaagttg gaaagccatt gctcatgggc caagtccagc tcatgtttct tcttggacca    21840
cccatgagct tggaatggtt attacatttt tatttgttct ttgtttccag tacaacgggc    21900
cttttgtggt aaaatacata taacatacaa cttaccatta taacttactt ttttctttt     21960 tgagacggaa tcttgctctg tcgcccaggc tggagtgcag tggcgcgatc tcggctcact    22020
acaagctccg cctcctgggt tcacgccatt ctcctgcttc agcctcccaa gtagctggga    22080
ctacaggcgc ctgccaccac gcccagctaa ttttttgtat ttttttttt ttagtagaga     22140 tggagtttca ccgtgttagc caggatggtc tcgatccccct gaccttgtga tctgcccgcc    22200
ttggcctccc aaagtgctgg gattacaggc gtgaaccacc gtgcccggcc tttttttttt    22260
tttttttgag acggggtctt gctatgttgc ccaagctagt gtcagactcc tggcttcaag    22320
taatcctccc accttggact ccccagtagc tgaagctaca ggtatgcacc atcttgttcc    22380
attttaacca ttgcttttgt ttgtttcttt gtttcagagt ctcactcagt tgctcaggct    22440
ggagtacagt ggctcaatct tggctcactg caacctccac ctcctgggtt caagcaattc    22500
tcctgcctca gcctcccgag tagctgggat tacaggcgtg caccaccatg cccggctaat    22560
tttttgtatt tttagtagag atggggtttc accatgttgg ccaggctggt ctcaaattcc    22620
tgacctcaag tgatccaccc gcctcagcct cccaaagtgc cgggattaca ggtgtgagcc    22680
accatgccca gcctatttta accattttttc agagcacaat tctgtggcaa taagcacatt    22740
catgttgtta tgtagccacc actgccgtcc atctccagaa cttctcctc tttccaaact     22800 gaaactctgt ccccatgaaa cactcactcc ctatccctct ccccagcccc tggcaccctc    22860
catcttgctt tctgcctcta tggatctgat gactctaggg acctcctagg agtggaatca    22920
cacagtgttt gtcctttttgt atctgctat ttcactgagc ataatatccc caaggttcat    22980
ccctgctgta gcctgagtca gaactgtttt cctttccatg gctgtatcac attcccttgt    23040
```

-continued

```
gtggatgaac cacgttgtgt ttattccttc atccatcgat ggacacttgg gttgcttcca   23100
gcttttgttt tgttttttg tttgtttgtt tgttttgtt agttcacgtc ttttgtgggt      23160
tttctttctt ttttgagatg gagtctcact ctgttgccct ggctggagtg cagtggcacg   23220
atctcggctc actgcaagct ccgcctcccg ggttcactcc attctcctgc ctcagcctcc   23280
cgagtagctg ggactatagg cgcccgccac catgcccagc taattttttt gtatttttag   23340
tagagacggg gtttcaccat gttagccagg atggtctcga tctcctgacc ttgtgatccg   23400
cccgtctcgg cctcccaaag tgctgggatt acaggtgtaa gccactgcgc ctggccgtct   23460
tttgttaatt catacagtta tttgtcttct ggtttgttga agcagtaagt cagacaacat   23520
ttgccacaat aatgtctgtc aaagtggctt gccataaaca ctgcagcacc acattcatca   23580
gaagggcaac ctcgacgaag gtgactaatt ttgccattct catccacctt ataatatttc   23640
aggacagcca gcttcacctt ctttctcttg tgcttattcg tcttgcaggt aagacttctt   23700
cttctggccg ggctcagtgg ctcaggcctg taatcccagc actttgggag gccgaggcag   23760
gtggatcacg aggtcaggag ttcaagacca gcctggccaa catggtgaaa tcctgtctct   23820
actaaaaata caaaaattag ctgggcgtgg tggcacgtgc ctgtaatccc agctactcgg   23880
gaggctgagg caggagaatt gcttgaactg ggacccggga ggcagaggtt gcagtgagcc   23940
gagattgcac cactgcactc cagcctgagc tacagagcga gactccatct caaaaaaat    24000 aaaaaaaga cttcttcctt tccttagcac caccacgaat tctcaataca agatgaagag   24060
gagactcctt ttgaatgttg tagtcagaca gagtacgccc atcttccagt gcttgtcttt   24120
gctgatcagg aggaattctt tctttaccct ggatcttggc ctttacattt tctaccatat   24180
ctgagggttc agcctcgagg gtggtggtct tccctgtaag ggttttcagg aaaatctaca   24240
ttttggtggc ggctccacca cagatggcgg atctaaaagg ttttgttt tgtttttt       24300 gagacagagt ttcgctcttg tcacccaggc tggagtgcaa gtggcacgat cttggctcac   24360
tgcaacctct gactcctggg tttaagtgat tatcctgcct cggcctccga gtagccagga   24420
ttacaggcat gtgccaccac cacacctggc taatttttt ttcttttgta tttttagtag    24480
agatggggtt ttgccatgtt ggccaggctg gtctcaaact cctgatctgg agtgatccgc   24540
ctgcctcggc ctcccaaagt cctgggatta caggtgtgag ccactgtgcc tggcctgctt   24600
ctgccttttg gctattgtga ataatgctgc tctgaacata gatgtgcaaa tatctgtttg   24660
cagctcctgc tttcaattct tctgggcgta tgtccaggag tagtgctgcc tgatcatatg   24720
gtaattctat gtttaacttt ttgaggcact gccaatttc acatttttaa accataggga    24780 aaaaaagtt gttttttt taaaaagac acagtctggc tctgttttcc acgctggagt       24840
gcaatggtgc aatcatagct cactgcagcc tcaaactcct gggctcaagc aatcccccc    24900 tcatcagcct cttgagtagg tgggactacg gcatgtgtca ccacacctaa ctaatttttt   24960
taattttttt gtagaggtgg ggtctcactc tattgcccag gctggtctca aactcctggc   25020
ctcaaaagat cctgccacct tagcttccca aagcactgag attacaggca tgagccactg   25080
tgcctagcca aaaatatttt gtaatgttta gtgaaaatag aaatcatata aaattcaaat   25140
tcatataatt ttcataaaaa gtccataaag aaaattttct taaaacattg tcagctgggt   25200
gcggtggctc atgcctgtaa tcacagcact tgggaggct aaggcgggtg gatcacctga    25260
ggtcaggagt tcaagaccag cctggccaat gtggtgaaac cccatcacta cttacaatac   25320
aaaaattagc cgggtgtggtg gcacgcgact gtaatcccag ctacttgaga ggccgaggca   25380
ggagaattgc ttgaacccgg gaggtggagg ttgcagtgag tcaagatggt gcccttgcac   25440
```

```
tccagcctgg gcaacaagag cgaaactctg tctcaaaaaa aaaaaaaatt gccaagctca    25500
gtggcaggca cctgtcatcc tagctacttg agagaccaaa gcaggaggat tgtttgagcc    25560
caggagtttg agggcagcct gagcaacata gtgagatcct gtccctacaa acacacacac    25620
acagtttgct acccccttt ttttgagagg gagactcgct cttgtcaccc aggctggagt    25680
gcagtggcac gaccttggct caccgcaacc tctgcctccc gggttaaagc gattctcctg    25740
cctcagcctc ccgagtagct gggattatag gcaggtgcgc caccatgtcc ggctaatttt    25800
tgtattttta gtagagatgg gatttcgcca tgttagccag gctggcttcg atctcctgat    25860
ctcaagtgat ccgcccgcct tggcctccca gagtgctgag actataggca tgagccactg    25920
cacctggccc cattttttaa tatatcatca gtgactgcta tcacatgtcc atggcagagc    25980
tcagcagctg tagagtggtt ggacagtagg gcccccaaag ctgagaatgt ttactatctg    26040
actcgttaca gaaaacattt ttttgtaccc ctggtatgtg gtgatgagtg agaatgagac    26100
aactgtccat ggattacagc tacacccaac catgtggctg attctcacga acatatgtta    26160
gcatagaagc cagaccccaa aaagaacata ccatacaaat ccatttatta aaaaaaagg    26220
gggccgggcg cggtggctcc tgcctgtaat cccagcactt tgggaggcca aggcaggcgg    26280
atcacaaggt caggagatca agaccatcct ggctaacacg gtgaaacccc atctctacta    26340
aaaatccaaa aaaattagcc gggcgtggtg gcaggcacct gcagtcccag ctcctcggga    26400
ggctgaggca ggagaacggt gtgaacccgg gaggcggagc ttgcagtgag ccgagatggc    26460
gccactgcac tccagcctgg gcgacagagc aagactccgt ctcaaaaaaa aaaaaaata    26520
cctaaaaata caaaaattag ccaggtgtag cggcaggtgc ctgtaatccc agctactcgg    26580
gatgctgagg gaggagaatc gcttgaacca agaggtggag gttgcagtga gctgaaatca    26640
tgctactgca ctccagcctg gcaacagag agagactccg tctcacaata atgataataa    26700
taataaatga aatacaaaca aaactaattt atgctgtcgg aaatgacgat ggaagagtcc    26760
tggggaatca gagatagtgg tgataaaagc ataccaggaa ggcccctagt gaggggggaa    26820
ttttgtaaaa gttttcagct gtaactctca tttgcacaat tttctctatg tatttatatt    26880
tcaatcaaca tgatgcatgt gtattaaagc cctgtgtaaa tgcaacggtg cacacaggtt    26940
caaagcgcag gcaatattta ttgagcaact attatgttcc atatgctgtg ttaaacacca    27000
tgcatacact aagaagcaga gggatgctgc ccttgcccgg gacgagttgg cccttgtcag    27060
tcagggaaag gcagacacca acagaacagc aataaaaagg ccgggcaatg gccaggcgc    27120
ggtggctcat gcttgtaatc ccagccttt gggaggccga ggcgggtgga tcacctgagg    27180
tcgggagttc gagaccagcg tgaccaacat ggagaaaccc cttttctact aaaaacacaa    27240
aattagccag gcgtggtggc acaccaggtg ggtagctgta atcctagtta ctcgggaggc    27300
tgaggcagga gaattgcttg aacccgggag gcggaggttg tggtgagcca aggttgtgcc    27360
attgctttcc agcctgggca acaaaaagca aaactccatc tcaaaaaaaa aaaaaaagt    27420
ccgggcgcca tggctcacac ctgtaatccc agtgctttag gagaccgagg tgggtggatc    27480
acttgagccc aggagttcaa gaccagcctg gccaacacag tgagaccctc cctctgtaca    27540
aaacgtaaga aaacattagg cagggatggt ggtggcttcc tgtagtccca gctactcagg    27600
aggctgagac agaagtaccg cttgagtcca ggagttggag actgcagtga gctatgatcg    27660
caccactgca ctccagcctg gacaacagag caagacccca tctctaaaaa aagaaaaca    27720
aaaaacaac aacaaaaaac accaatgaaa tgctcaatca gccatcagcc tcaaggaccc    27780
ttccatctcc caaggagagg aaccctttc cgtgagaacc tctgacctaa aaatcaaccc    27840
```

```
cacatggggg aatccagaaa gtattttggg gggaggaaaa gatgtttgaa gggagggtgg   27900
aggatgcaga agggttaacc aggagaggca gttagggagg gccttctggg tggagggaga   27960
ggactgcatg ttccaaggac ctgaggcaga atggagtgtg tgtatttaga ggaactgaaa   28020
gcaaatttgt gggacagggg atctagaggg gaaaagtgaa ttccacaggc tccctgtctc   28080
ttctggtcct agcaggaact ttcaagtccg tttttgtcca gatatttccc catgctcaag   28140
tcccagctca tcctgcctcc ttgaagacat gacttctgtc tcttcttgag ctactctttg   28200
acacaccctg gacaaagggt agcttgaaaa gagacagaaa ccatgttatt gccaggtgca   28260
gtggctcacg cctgtcatcc ttgtgctttg ggaggctgag gcaggaggat cgcttgaggc   28320
caggagcttg agaccagcct ggacaacata acaagacccc atctctacaa agataaaagg   28380
gaaaaagccg ggcgcagtgg ttcacgcctg taatcccagc actttgggag gccaaggtgg   28440
gcagatcacc tgaggtcagg agttcgagac cagcctggcc aacatggcga accccgtctc   28500
tactaaaaaa tacaaaaatt agatgggcgt ggtggcgggc acctgtaatc ccagctactc   28560
gggaggctga ggcaggaaaa tcacttgaac ccaggaggtg gaggttgcag tgagctgaga   28620
ttgcaccact gcactccagc ctgggcgaca gagtgagcct tggtctcaat caatcaatca   28680
atcaatcaat ggaaaaaaat tagctgggtg tggtggtcca tgctggtagt cccagctact   28740
gaggaggctg gggtgtgagg atcacttgag cccaggaagg ctgagactgc aatgagctat   28800
gatggcatca ctgcactcca gcctggacaa caaagcaaga tcccgtctca aaaaaaaga   28860 agaaaaagaa aaatcatttt ttgagagctc tgattttcaa accctttgtt ctcagaactc   28920
ttcgggtaaa accttttgaa cgacacaaaa ggagtgggca gctgtgatga cagattgagg   28980
agaaagcagg gtaggcatgg aacctctagg gttccctagg gacccagttt gaaaactctt   29040
ggttcagtag caggaaaagg caatatgccc cttaattctc ttctaaaaca taaaatcctt   29100
taacttcctc tgatttctac cagtaaaact gagctctact gacctcaatt ttgtaccaaa   29160
tgctatctaa taaaatccca gaaacagtga tttttgaaaa atccattttg ttgatgtgta   29220
atttacatac agtagaatgt gcctatctta tgtgtttggt ttcatgcatt gttttctttt   29280
ttcaactttt taaattttt tttttttttg agacagggtc tcactctgtt gcccaggttg   29340
gcgtgcagtg gcacaatctc ggctcactgc aaccttcgcc tctcgggttc aagcaattct   29400
cctgcctcag cctcctgagt aggtgggacc acaggcacgc gccactacac ccagctaatt   29460
tttgtatttt tagtagagac agggtttctc catgttggcc aggttggtct cgaactcttg   29520
acctcaagtg atccacccac ttcggcctcc caaagtgctg ggaccacagg cacacaccac   29580
cacgcccaac taattttgt attttcata gagatggggt ttcaccatgt tgcccaggct   29640
ggtctcaaac tcctggcctc aagtgatctg cctgccttgg cctcccaaag tgctggaatt   29700
acaggcataa gccaccatgg ccagccctct ttatcaactt ttattatt ttcattttt   29760 ttgagacgga gtctcgctct gttgcccaaa ctggagtgca gcgtgcgac ctcagctcac   29820 tgcaacctcc gcctcccggg ttcaagcgat tctcctgcat cagcctccca gtagctggg   29880 attacaggtg cccgccacca cgcccatcta atttttgtat ttttagtgga cgggtttt   29940 caccatgttg cccaggctgg tctcgaactc ctggcctcaa agcgacctgc ccgccttggc   30000
ctcccaaagt gctgggatta cagttgtgag ccgccgcgcc cgggaccctc tttatcaact   30060 tttatttag attcagggga tacctgtgcc agtctcctac ctgagtatat tgcatgatgc   30120
tgaggtttgg ggtatgagcg actctgtcac ccagatggtg agcacagcac tcaacagtta   30180
gattttcaac cctcatgccc cttttcctca cccctccctg gcaatcccca ctgttcatta   30240
```

```
ttgccacctt tatgtccatg agtacctgaa gtttagatcc cacttataag tgagaacagg   30300
cagtctttgg tctgctgtta ctgagtttga tgcattttga caaatgtgtc tacctgcctg   30360
ctgcacgttt tggttttccc aagaattatt ttctaaaaat cagttttat taaggtggca    30420 tttatataca ctaaaattct gcacacgatc ttgtaaccat caccaccaaa tacgtattta   30480
tttatttatt attatttttt agagatggcg tctcactctg tctcgatctc ccacgccggg   30540
gtgcagtggt gccatcagag ctcactgcat cctccaactc ctgggctcaa gcgatcctcc   30600
tgcctcagcc tcctgagtag ctaggactac aggcacccac caccacccac agttaattga   30660
aaaaattgat tcttctttgt agagacaggg tctcatatgt tgccaggatc cttggtcttt   30720
gacctcccaa agtgcagaga ttacaggcat gcaccactaa tgccgggcca aatacttgta   30780
atttaaatta tcgctgggct gggcacgtgg gctcacgcct gtaacccagc actttgggag   30840
gccgaggggg gaagttcacc tgaggtcagg agttccagac cagcctggcc aacatgctga   30900
aaccctgtct caactaaaaa tacaaaaatc agccggacat tgtggcagac gcctgtaatc   30960
ccagctaatc gggaggctaa gacaggagaa tcgcttgaac ccgggaggca gaggttgcag   31020
tgagccgaga tcgcaccatt gtgctccaac ctgggcaaca gagcgaaac tccatctcaa    31080 aaataataa taaaataaat tatagttgga aaaaggggt ttcctaaaga cccaagggaa     31140
atggcctctt tgttcctgaa gccacagaga ggattttcct gctccccaca actagttttc   31200
cttgtgaaaa ttcataattg ctaccagctt gttctcctct ctgtcactat acatctgtcc   31260
ttgaagcctt atttgaacaa agagttctgg tatcactcgg atgcctagaa actgttgccg   31320
ttctgtgaaa ccgaccacca gaggaaaccc atgcttctca ttggctgcct tactaagatg   31380
gtgacttgtt gccctggtga caagttgcaa tgacaggtgg ctctgccaaa tcagaacaca   31440
gtgatacttg cttcccctcc cgggtgaagg atggaaaata aaagtaaaag ccttggcggc   31500
tgtcaggctt ctttaccaaa gagctggaga gcactccttg gccccattta tgcaaacact   31560
tcccatctac agatgatcca gcttcggagt gggagtctaa gcagctgcca ggaccaccgc   31620
ttggcagagg acaggctggg ggctctggca tgacctgctg gggccaggct gtgacttgga   31680
gcaagaggta gcaagaacct cgaggcagtg aacatcaaaa gagagatttc cggggctaaa   31740
caccctaggt ttttccttcc tcctgaaccc taaccctaac cctctcggct cactgcaacc   31800
tccacctccc gagtgcaagc aattctcatg cctcagcctc ccgagtagct gggatcacag   31860
gcgtgcgcca ccacgcccgg ctaactttgt atttttatta gagacggggg tttctccacg   31920
ttggtcaggc tggtgtcaaa ctctcgaact caggtgatct gcccgccttg gcctccaaaa   31980
gtgctgggat tacaggcgtg cgccaccgtg cccagcttat ttttgtattt ttagtagagg   32040
tggggtttca ccctgttggc caggctggtc ttgaactcct gaactcaagt gatctgcctg   32100
cctcagcctg ccaaaatgct ggggttacag gcgccaggcc aagtatctta ttttaaaagg   32160
ttacaaagaa tatagatgtg gataaaataa aagtttcttt gcattaccac tttcctgcaa   32220
gaaatgaggg ggaggggctt atgaaacaac tcacaccccc ccaattgagg aactgtagat   32280
gaaagggaag gtgctgacag gcccgtctgg ccacggtttc ctggaataaa actgagccac   32340
acacctccac aaatccccag cctccggcaa gtaccccaga agtactcaca ctccaccacc   32400
ttctgtgatc gcaacagccc tacgcaacat tacagagggc aaaacccacg ctggggaagg   32460
cggggctact gtcaaaaggt caccagggcc aggcacagtg gctcacgcct ataatcccag   32520
ctccttggga gaccaaggca ggaggatccg ttgagctcaa gagtttgagt tcagcctggg   32580
caacacagga aaaccccgt ctttacaaaa acttttaaa aattagctgg gtgtggtggc     32640
```

```
atgcccgtgt aatcccagcc actacttagg aggccgaagg gggaggatct attgcttcag   32700
cccgggagtt tgtggctgca gtgagctatg attgcaccac tgcactccag cctaagtgac   32760
agacagagac tcttaaaaaa aaaaaaaaaa gggcagggca cggtggctta tgtctgtaat   32820
cctagcactt gggaggccg aggcgggcag atcatctggc gtcaggagtt cgaggccaac   32880
ctggccaata tggtgaaacc ctgtctctac caaaagtaca aaacttagct gggtgtgatg   32940
gtgggcacct gtaatcccag ctactcggga ggctgaggtg ggagaatcgc ttgaatctgg   33000
gaggtggagt ttgcagtgag ccaagattgc gccactgcac tccagcctgg gtgacagaat   33060
gagactctgt ctcaaaaaaa aaaaaaaaaa gtggggcacc tatattccca gcactttggg   33120
aagctgaggc aggaggatgg cttgaggcca aaaattcaaa acccggcctg gcaacatag    33180 caagacccca tctctatgaa aaaaaaaaaa aaaagtcac caggccagct agcctagatt    33240
tcagagccag aatttgtctg atgccattgt ctttactttt tcttttttctt tttttttttt   33300 ttgagacaga gtctcactct gtcacccaag ctgcagggca gtgggacaat ctcagctcac   33360
tgcaacctct gcctcccagg ctcaagcgat tctcctgcct cagcctcctg agtagctggg   33420
attacagaca tccaccacca tttccagcta attttttgtat ttttagtaga ggtgaggttt   33480 ccctttttg tcaggctgg tctccaactc ccaagctcag gtgatctgcc cacctcagcc    33540
tcccaaagtg ctgggattac agttgcgagc caccacgcct ggactgctct tcattctttt   33600
ttcagaactt tcccagctgc caacagagac agaaactgaa tcatctcaga agtgaatgaa   33660
ggaggctgag ggcgggtgga ctgcttgatt aggagttcga gatttgccta ggcaacatgg   33720
aaaaagcctg tctctgctaa aaatacaaaa attagccggg cgtggtggca catgcctgta   33780
atgccagctg cttgggaggc tgaggcagga gaatcacttg aacccgggag gcagaggctg   33840
cagcgagccg agatcgcgcc actgcactcc agcctaggta acagggcgag actccgcctc   33900
aaaaaaaaaa gaagggaatg aaggacaccc aaaatggagc ctctgtctgc cagggctttg   33960
ctatcctggc ctgcctatcc cagccctgga cacctcatct ctgatcccac cagagcggaa   34020
ccttcccatt cgcagggcca tttccttacc cagaaaccttt ttcacaatgt tcttggcagc   34080
agctgttggt caactgtgtt ttaaggtttt tgagcaactt tacagaaaat aaaagggaag   34140
ctaccctcaa tgtctgggtc tcccccctggg tggcctctct ttgtcacctt actcatttcc    34200
acgagatttc cttgcttcgt tgagttacat cacctccttt tcctgtctgg gtccaggacg   34260
cctcctctgc aggtctccag cactgattcc tttgtccccg atttctctgc tagggtcgct   34320
ggcttcacca tccaccacc actgctgctg gcccagcccg cagctttaat ttctctggac   34380
cctcacgttt ttgttatttg tgttttttttt ggagatgagg tcttgctctg tcacccaggc   34440
tggagtgcag tggtgcaatc acagctcact gtagcctcca cctcccagac tcaagtgatc   34500
ttcctgcctc agcctcccaa gtagctgggt gtgtgccacc aggtgcagct acatttttg    34560 tagaggcagg ggtcttgcta tattgcccag gctggtctca aactcccagc tttagatgat   34620
cctttcacct cggcctccca gagtgctggg attaccagca tgagccactg cacccgtcct   34680
ctcatgtatt tttattaat cgatttatct atttacttat tttgagacag agtcttgctg    34740
taccacccag gctggagtgc agtggcatga tctcggccca ctgcaacctc cactccctgg   34800
gttcaagtga ttctcctgcc tcagcctccc gagtagctgg gattacaggt gcccgccacc   34860
atgcctggct aattttttgta tttttagtag tgacgaggtt tcaccgtgtt ggccaggctg   34920
gtctcgaatt cctgacctca ggtgatccac ccaactcggc ctcccaaagt gctgggatta   34980
caggcgtgag ccaccgcact cggcctccct catgtatttt taagcggaac aggttcaaga   35040
```

```
tcacaaatgt tttcctctca ctctttcaat gagtttctat tctagaatct cctgcacgcc   35100
acaggaagga gaactctcac cctgtaatgc acataaatac atgagatcac cattgttctc   35160
acccagtaat cagaatcgtt agtgataatt agtaataaat ttatttttac tatatctaat   35220
aaattagata gtaattacta tggcagccaa tcgttcctgg gtgctcccta gatgcttcca   35280
agggagccac acgtgaccct cagggctgtg cccattccag gctcttctgc tgagctcatg   35340
taaccgcttg cctcaaggca ttccacaaat aatacataag tcaatgtatc acgttgtcac   35400
tttctgtaca aaccagctag ttccggaggg aagcagaaag ccttttttcag aagaaccaca   35460 gctaattcca gtagcaggaa tgataaagtt ggacataatc ctcaagagag taatgaatca   35520
aaaatggatg gcgggccagg cacggtggct gatgcctgta atcccagcac tttaggagga   35580
tgaggcaggt gaatcatttg aggtcaggag ttcaagacca gcttggccac catggtgaga   35640
ccccgtctct actaaaaata caaaaattag cctggcatgg tggctcatgc ttgtagtccc   35700
agcttcttgg gaggctgagg caggagaatt gattgaaccc tggaggtgga gattgcagtg   35760
agccaagatt gcatcactgc actccagcct gggcaacaag agcgaaactc tatctcaaaa   35820
acaaacaaac aaacaataac aacaacaaaa ttgatggctg ctaatgactt ttttttctttt   35880 cttttccttt ttatttttat tttttatgag acagggtctc actctatcgc ccaaactgga   35940
gtgcagtgcc gagatcataa ctcagtgcag cctcaacctc ttggactcaa gtgatcttcc   36000
cacctcagcc tcccatgtag ctgggactac aagcaattgc tgccacatct ggctaattat   36060
tttattttgt tgtattttat ttatttattt tttgagacag agtcttactc tgtcacccag   36120
gctggagtgc aatggcatga tctcagctca ctgcaacctc cgcctcctgg attcaagtta   36180
ttctcctacc tcagcttcct gagtagctgg gataacaggt gtgcaccacc acgcctggtt   36240 aattttggt tttttggtag agacggggtt tcatcatgtt ggccaggctg tcttgaact   36300 cctgacctca gtgatccgc ccatctcagc ctcccaaagt gctgggatta caggtatgag   36360
ccaccgtgcc cggtctttat tttattttta gtagagacag ggttttgcta tgttgcccag   36420
gctggtctca aactcctggg cctaagtgat cctcctgcct tggcctccca aagtgctggg   36480
aactacaggc gtgagccact gggcccagct cctgttaaca tctttatgtg gagagttact   36540
ggggaccagg gacattcccc aaacccaccc atcaatcgta gtgacatgac gttatggacc   36600
ccctgatgtg atgtaccagg aagtacccgg ccctaccagc atgatattat tctggctgca   36660
actgaccctt attccaatag agcatgtggt tctaagccat ttatagggta aacattgggg   36720
cagggatggg gagagaggaa gcaacctgcc aaatccagaa tgaggatcat tcctcggtac   36780
cagaagagaa ccagaaagaa agcaccctaa gtggggatac cacaaggaag taaagcaggg   36840
gcctctccca gctggggaag ggaaggagga aggagtacaa tagcttgcaa ggcacagcat   36900
tgcggatgat gggaatagca ggtgcaaagg ttctggggca gggacagtgt ggtgtgtttg   36960
aagaacagca gccaggttca ccatgagatg ggaaatggac ttgggggaag ggatctcaaa   37020
ggataatttt tttttttttt ttgagacagg gtttcgctct tgttgcccag gctggagtgc   37080
agtggcatga tggctcactg caacctctgc cttccggttt caagcgattc tcctgcctca   37140
gcctcccgag tagctgggat tacaggcgcc caccaccacg cccggctaat ttttgtattt   37200
ttagtagaga cagggtttca ccatgttggc tagactggtc ttgaactcct gacctcgtga   37260
tccgcccgcc tcggcctccc aaagtgctgg gattacagac gtgagccacc gcgcccggcc   37320
ccccaacttt tttttgttt ttaacacaac ttctcgcttt ctcacccagg ctggagggca   37380
gaggcacaat catagctcac tgcagcctcg aactcctagg ctccagcgat cctcacagga   37440
```

```
gggttttgag gatctgcata aagcgtgcag agggagcttg acttcgtgct cgttaggacc    37500
cgatattgtc agctgccgcc gcccacaggg acacataaat atttgtagac tcaatatttg    37560
cctttagtgt gaagacattg catcacctgg gtataagtaa ggagcagagg cagaggcggt    37620
ttaagcaaca gacttttgtc tccgctgaga accacggaat aacccctgac ctacttcccc    37680
gtcgtgtcta attcgggtca cctcatctcc agttacagac gcggaagatc aaagaaaccg    37740
ggaaattgcg ccgcagcgcc ccctggcgtt cgcagcgcgt gcctacacaa gccactcccg    37800
gcgcaaaact gcggcttccc aggaaattga gtttaaatgt ttttttttct tttttcttaa    37860
tctagaaaag atcatttatt gtatcaagta actacccagt taggcgtgaa tacattttaa    37920 aattttatt aaaacgagta ttggccgggc gcggtggctc actcctgtaa tcccagcact    37980
ttgggaggcc aaggcaggtg gatcacggcg tcaggagttc gagaccatcc cggccaacat    38040
ggtgaaaccc cgtctctact aaaaatacaa aaattagctg ggcgtggtgg cacgcacctg    38100
tagtcccagc tactcgggag gctgagacag aagaatcggt tgaaccgggg aggcggaggt    38160
tgcagtgagc tgagatcatg ccactgcact ccagcctggg cgacggagcg agactccatc    38220
tccaaaaaat aaataaataa ataaatataa tataatataa aataaaataa aaagagtatt    38280
gtagagattg gctgggcaca gtggctcaca cctctaattc ctgcattttg ggaggctgag    38340
gtgggaggtc ttcagcccag gagttagaga ccagcctggc caacatggca aaaccccatc    38400
tctactaaaa gtacaaaaat tcgctgggca tggtgtcgca cgtctgtgat cccagctttt    38460
tgggaggctg aggcaggaga atcgcttgaa cccaggaggc agaggttaca gtgaatcgag    38520
atcgcaccac tgcactccag cctgggcaac agagtgagac cttgtctcaa aaatacatat    38580
atttaggaat ttgctatgtt gcccaggctg gcctcaaact cctggcctca agcaatcctc    38640
ccacctcgcc ctcccaaagt gctgggattg caggcgtgag ccactgtgcc cgaccttgag    38700 cttaagttttt aaacattaaa accacctccc tcccactccc tgcacctccc gtaagttaaa    38760
acgcgtccct gctgaggccc tgcaaaggca tatccagggc aggcggaccc caggggtcca    38820
cagccgaccc actttcttcc ccacacctca tcccttcac aactctcctc atccatctcc    38880
ctgccctggt gggagattcc gataaatcct aattgtggaa ctgctgaatc agagggggct    38940 gcatttttcct tagcccccac ctgcaaattg tgtgtgcagt ttttctggga tgagtgtcct    39000
tagatttccc tgaattctca aaaggatctg tgacctcaaa atcaggagag aggccgggca    39060
cggtggctca cgcctgtcat cccagtactt tgggaggccg aggtgggcag atcgcttgag    39120
cccaggagac cagcctggc aacatagcca gacccagtct ctacaaaaaa ttaaaagatt    39180
aactgggctt ggtgatgtgc actcatggtc ccagctactc aggaggctga ggtgggagga    39240
tcgcttgagc acaggcggta agagaggctc tacctctgaa gaggatgctt ccccacccttc   39300 tgccccctcc ccaggcaccc actccagcag tgagaatttc actgccaaca tgagacatgg    39360
gtccctacct gtcccaactc agaccctgtc tatgatgtcc tatggcctca gcagggacca    39420
aaaccctcac catggcctca ccagaacctc cacgtggttc tcagattggg ttgcaggtca    39480
gtaccctccc ctccagctcc tcaggggcct cctgcattct ctggccttgg cttctgctct    39540
gccctcccct cccttccctt cgcccccttc attttcattc tctatgcaaa tgctgcctcc    39600
tctaggaagc cttccctgat tgcccccagt ctgggtggat tagatgtgat atgggctccc    39660
acagcccctt ttgcctcaga ttactcatgt ggctggctgt atatctgtgc cccagagagg    39720
tttcttttcc ttttttcttttt tttttttttt tttgagata gggtgtcacc ttgccaccca    39780
ggctggagtg cagtggcatg atcatagctc attgcagtct caacctcccg ggctcaagca    39840
```

```
atccttccac ctgaaagtcc tgagcagctg ggactacagg cgtgtgccat cacgtgcctg    39900 actaatttt  cttatttttt gtagagatgg ggtcttgcta tgttgcccag gctggtctta    39960
aactcctagc ctcaagcgat ctcccacctc agtctcctga gtaaactgga ccccaggtgc    40020
aagacaccat gcccataaaa aaattttaaa aaaatttaat tttaaaattt ttttgtagag    40080
ataggatcgt gttatgccgc ccaggctggt ctcaaactcc tgggcccaag cgatcctccc    40140
acctaggcct cccaaagcac tgggattaca ggtgtaagct acctcgcccg gcctctcctg    40200
ttctattggt gctgtgagat tcacacctca cttgagtgct atgggctgaa ctgtgtcctc    40260
tccacaaatg tctatgctga agtcctgccc cgcaactgcc tcagaaagtg actatacttg    40320
gagatagaat cttaaagaa ataattaagt aaaaatgagg tcatatgcgt gggccctaat     40380
ccaacatgac cagtttcctt gtaagaagag cagattagga cacagacatg cactggggcg    40440 ggggaggag actgtgtgaa cacacaggga aaacacagct gtctacaagg aaggagaga     40500 agcttcagaa ggagtcacac ctgtggacat cttcatcttg gacttccagt ctctagaaac    40560
agaagactat aaatgtgttt gctttgagac agagtcttgc tctgttgccc aggctggagt    40620
gcaacggtgc gatctcagct cactacaacc tccgcctccc gaaggaggcg tagtgtaatt    40680
ctcctgcctc agcctcccaa gtagctggta ccacaggtgt ccaccaccac acctggctaa    40740
tttttgtatt tttagtagag acaaggtttc accatgttgg ccaggcttgt cttgaactcc    40800
tgacctcagg tgatccacct gcctcagcct ctcaaagtgc tgggattata gttttgtttt    40860
tgagatggag gtctcgcttt tgtcacccaa ggctggagtg cactggcacg gtcttggctc    40920
actgcaacct ctgcctccca ggctcaaatg atcctcccac ctcagcctcc tgagtagctg    40980
ggaccacggt gcacaccact acattcagct aattctattt ttttgtagac acaggatctc    41040
actatgttgc ccaggctagt cttgaactcc tggcctcaag tgatcaacct gccttggcct    41100
cccaatgtgc gactacaggc atgagccacg gtgcctggca atttctgtta agtcacctag    41160
tctgtggtac tttgttatga cagccctagc aaacagatac acccaccgaa ggccctgata    41220
agtcctgcag tcaggagtct ctgtgaaccc cgtggggctg ggaggagaaa gcagggagcg    41280
tttgctgtgt gcctcacatg aatacagcag aagctgaaca caactcctgg catcgtatgc    41340
ctacaggtcc ccttggaaca gttctagggg ggttggagtt ccagggtcca ttctgcttaa    41400
taacaatatt aacggagcag ccaaaatggt tccagtgaaa atgggggtagc agcagctgtc    41460 atgcttgcac gccaccagcc ttcctgcgct atctctgttc tctcctctgc aaagcagctg    41520
ctattttggg ctccctgttt ttagattggg aaccccggaa gttggtcagg gcctcaccgc    41580
tagaatatct tagagctgat attcaaatga gagtccaatt ttttttttt tgagacggag     41640 tctcgctttg ttgcccaggt tggagtgcaa aggggcaatc tcggctcact gcagcctcca    41700
catcctgggt tcaagtgatt ctcctgcctc agcctcccaa gtagctggga ctacaggtgc    41760
acaccaccac acccagctag ttgttttgta tttctagtag agatgggttt tcaccatgtt    41820
ggccaggctg gtcttgaagt cctgacctca agtgatcctc ccgccttggc ctcccaaagt    41880
gctgggatta caggcgtgag ccaccgtgcc ctgccaaaag tccaagttct aacctccat    41940 gagggcttga gatgccctca ggggcaggga gaggctaatt ctccttctga gaggataata    42000
ggggttggtg gggcctgggg cacaggcctg gctcagcaca actcccaggg actcccttga    42060
taagaaggtg aggtaggcac tggctggcag agcgacggga agagtttatt tctctggaaa    42120
ggggagggta gggggcgggg ccaggggtca gggcagggca atgtcctcca gcttcttgtc    42180
cagtgccttc aggtcatcca ggaagcgggt cggggtgagg atgtgtgagg agcctgtgca    42240
```

```
ggggcagagg tttggggaag atgttggggg gcgctgcctt cgtctttgac aggctcccgg   42300
tcccggctgg tgtggggctg tccctgtccc tcagcaaacc aggtccctga ctccaaggac   42360
tctggagtcc agacacctag aaggtacaag cccaggcccc gggaacccaa gccccagacc   42420
ccagggtccc agtcctggtg acttaccaat gagcacctcc cacttgccct cggtggccct   42480
ggtcacctcg taggcggccc tcatctctga catggccaca ccgcccatga catacacgat   42540
gagccggggg cccgcccggg cttctatgcc agccttgttc ttgtgccagt gaccgaagcg   42600
ggcactgtgc agggcagggg cagaaagtcc aggcaggagg ccctcaccgc cgccaggccg   42660
cccacctaac acagacccag gcgtgggcgg gggcggcccc ggggcctcac ctgacacgcgg   42720 cctgggagct ggccgtgggg gcggggtcgg atacgaaggg ccacaggttc ctgtccagcc   42780
ggtcctccac ggcgtcctgg cggccgagag gcaggttagg ggaggaaccc caggcatggg   42840
gtccggggtc aggagtgccc cccacggggt attcagggg caagatcctg gcagacagga    42900
accagcatct ccacctcctg cctctggggg acccaggagt ctaggcctct agtccattgg   42960
ggacctagaa atctagatcc ataactcact ggggacccac gaatctaatt ccataactcc   43020
ttgggtaccc agaagtctaa acccacagtt cctcggcaac ccagtagtct gggcctccag   43080
gcccttgggg accatcagtc aatacccca gcccctttggg gaacccagtg tctgggctct    43140
cagcccctca gagccccaga agtccaggta ttcaaggtcc atggggatga ggaggcccag   43200
gtctctggcc cccacgcaga aagaggggcc ggggctctta gagggacaag gaggaagcca   43260
ggaagccgcc ccaggcccat tgccattgga tggtgctgcc ctgggatcct gggaaggcca   43320
gggctggggc tcagggcac tcctgcggga caggggaaca gactagagag atatagcgga    43380
ggcagccggc aggtggggag gaagtgaggc tccccagcac aggccccgct gtcaccccaa   43440
ttcctcagct gcgggcttgg cgtgccccc tcagcagagc agatcggtgc caagggaatg    43500
ccagcaatga gcattttccc ctaagccctg aggcttagca cctcagcagg agggaggctg   43560
agccgccagc cgatgcggag ggctggcccc caccctgacc tgccacccag tacctccatt   43620
acatccttga tgaccggggt ccagcgggac agctgatagg tgggctccat gcgttctctc   43680
ggctccagcc ggctggaggt ccccgagccc tacaggcagg gcagggaggg cagcaggggg   43740
attgagggga aggaggctgg tcacagaggg gctgcgcctg gtgtggctgg tagggtgggg   43800
gatggcaggc aaagatgggg aagtggaaca gagagcgaga gagagcgaga gacagcaaga   43860
aagcgagaga gagaaacagt gagccagaga gagacggaga gagaaagcca aagggagaga   43920
gagcgagcca gagaaagaca aagacagagg cagagatagg caaagagata agaagcagtg   43980
agacaaagta tgaaggcaaa gagagagaca agagatgaag caggaaacag agagaggaag   44040
atggggacag aaggggacg gagaggggag gggagcaaga cagagaacag agagaaaggg    44100
gaaggcagag agaagggtga gagagagaga tatggagaaa cagtgcacag cgagatggat   44160
gagggatggg ggagagatgg ggacggggtg agggcaccct ggaggggggac gcacagggcc   44220 agagagagac aggagaggct gacccaagag tcaagcacac acatggctgt gtgtgggtgc   44280
tggatgggtg cggggaccc tcagagaccc ctggagccc agatagacaa tgtggtgtag     44340 ccccccatgct ggggacccta ctccctgcct ctagcactca gaccacccgc tcccaactgc   44400
accactgcca ggaccagcct ggcagcgacc atgtctcact tcccctgcct attgtgtaag   44460
ctgggactgg gagaggcccc agtgtcctct gggcccaga ccagaccga aacactgctt      44520 ttggcctccc agcaaccaca ccacgccagg aaccacaccg tgcctgtgca ccaatgcccc   44580
tctgccttgc agagccccgg ctgtgatccg caccctctcc cagggtcccc ccatgcccgc   44640
```

-continued

```
tcctggcgta ccccgggggtt ggtgacagtg cctcccagct gctccaggtt acggatgagg    44700
ctgctgtgcg cctgtacatt ggcatgctgg atcagcttgg ccaggttctc ctcactcaca    44760
cctgggggac gggaatgggc agggtggagg cggcggccag gtgagctccc aggtttaggg    44820
gagtttgggg tgggctgagg agctcccagg actctgatga gagaaccttg cagtggggag    44880
ggcctcagta ccctgtgcta gtgtgagcaa gagtgggaaa cctggagggg gtagatcagg    44940
ggctcctcca gatgagctga gggagcccca catctatagg aatcacagat gtgagggttt    45000
ctacgttagc agggagccct cacctcagtg gaggaatccc caagccaatg gaggagggtt    45060
cccgggtcca gaggggtagc tgtgggggtt ggtgagcccg tgagtgcaa atgacccaag    45120 gagagctgtg gggttcagca gttcccagga tcgtgggaga cgctggcaaa tggggacgtt    45180
ccaactccct gcagccccca cccaccattc cgaaggagga tgtagagcag caggacccgg    45240
atcttgtcgt aggcgggcac cgccgcgtcc agcagcaccg gaacgatcag cttcatggag    45300
tccttgatct tctccccctc tgcgtcgag cccatggcca ggtcctgcgg gcatggggtc    45360
agccgtccac cggccgctat gtgtcaggga aggggatggg agaggcgggc caaggacatc    45420
cccaggatcc tcggcaagag gacatttggg tcctacctca tctcagcacc aggtctctca    45480
aggtcccacc cctgtccagg gacagtctct ccacaggccc tgctcctcac ccaggtccca    45540
cctttccagt gccccacccca cctacacaca ggtcacacca ctatcctgag actacctctc    45600
caaggctcca ccccctcaccc aggtcccagc tctccaaggc tccaccctc acccaggtcc    45660 cagctctccg aggctccacc cctcacccag gtcccacctc tccgaggttc cacccctcac    45720
ccaggtccca cctctccgag gttccacacc tcacccaggt cccacctctc cgaggctcca    45780
cccctcaccc aggtcccacc tctccaaggc tccaccctc acccaagtcc cacctctcca    45840
aggctccacc cctcacccag gtcccagctc tccaaggctc caccctcac ccaggtccca    45900 cctctccaag gctccacccc tcacccaggt cccacctctc cgaggttcca ccctcaccc    45960 aggtcccacc tctccaaggc cccgtgcctc acccagatcc cacctctcca tggctctacc    46020
tgtctcccag ctcctacctc tccaaggccc caccctcac tcaggtccca cctctccaag    46080
gctccgcccc tctcccaggt cccacctctc ttaaggctcc acccctctcc caggtccac    46140 ccctccaagg ttccaccct catccaggtc ccacctctcc aaggttccac ccctcaccca    46200
ggtcccacct ctcaaggct ccgcccctca cccaggtccc acctctccaa ggctccgccc    46260
ctctcccagg gcccacctct caaggctcc attcctctcc caggtccac ctctccaagg    46320 ctctgccccc tcacccaggtc ccacctctcc aaggctccat tcctctccca ggtcgcacct    46380
ctccaaggcc ctgcctacct ctccaaggtc ccacccacct atgaataggc cacattcctg    46440
tcctgggacc acctgtccaa ggctctgccc ctcacccaag tctgacctct ccaagcccca    46500
tccacctatg cacaggccac accctcatcc taggaccgtt tctccacaag acccactcct    46560
tccccaccag gtcccacctc tctccaaggc ccctccacct ctcacaagc cctgcccctc    46620 ccccagaacc cccatctct acagttcagc ccctccccaa taccccgcct ggcaggacc    46680 atcacccctg ccccccgcaa gccctgcccc acctgctcca cactacacag cttctccacc    46740
gagcccttga agtgcttcat acaatcatct gctagatgca ggtgcgtaga atactgcagg    46800
gtgcagggtg ggggttgggg gataacaaag gctgagtcaa ggcagaacgc agacagagca    46860
tggggttgag gggccgaggt gtccccgctc cctgcccacc cgagcacacc ttattcagct    46920
ccttctggta ctgcggcatc tttttcagga tctgggatag gtctttgatg ttcgcctggg    46980
gaagtagggg gaagagggta gggattgggg ggcgaagcca ggcagtgccc acctgggtct    47040
```

```
cagtccaggc tcgaaatcca ggctgtggcc ctgcgcccat ggggaggggg gcttccttcc   47100
accagcgcct ttggtgacct gggtccgccc taccttgtc cgtggtcagc ctcttgctct    47160
cacagaaggt cctcaggagc tccgtgacct tcctggccat gagggtgggc ggggtgaga   47220 gtgaggggag aggagccaca ggccatgggt gagcccactc aggggggaca gggagaggtg   47280
gggtgaaatt ggaggccagt ctggagtcac acgaggggtg ctcatgaggg ccaaagactt   47340
ggcagcagcc agggatccca aggccgctac caggcccaca gtgggcggtg ggggggggat   47400
ccggtccccg tgtgcacgca cttggacaca tctgcgatat gcatgtggcg aagctccacc   47460
cacaagtcat cgtcctcgtc cagcaagacg gccttctccc gcgcctcgct cagcccggtg   47520
gtctcatacc tggggaggaa ggagggagcc tggggtcag gggagctgag gactggggaa    47580
ccaggtcagt ggcaagggtg gggacgggtt ccaagtctgc agacctgtat gtgtcctgct   47640
ctatgtccag cagatcatac gccatggcct ggaacgtgag ctcatgcagt agtggggaca   47700
cggggtcagc tgcccggtcc attatcagca gctgggagcg ggttttctct gggccctggg   47760
gtggggttta gggcaggaat gaggcactga ccctgagccg gttgggctg cccctcacct    47820 cccaagcacg cccctcacc tcgcccagac tgggagtgtc tgccttgaag gcgttcagct    47880
tggccaggac ggcgtgggcc aactgggctg tgtcctctgg gccctggcg gggaggtcag    47940 acacggggga catcatcagg ggatgggtc aaggatgggt ttgaaggtga gagtcagggg    48000
ccagggtagg gccggggctg gggtcacaag agaggttaaa ggttaggtgt tgcacgcggt   48060
taaggggggg tcggcatcgg ggtgggctg ggtggggtcc ccacttgcgg tagcggatgg    48120
ccgggtactc ctgcagggtg gcgcacagcg tggcaatctg ctgggccagc acctcgagct   48180
gccgcgtgcg ctcctctgcc cggaagggc agtagaggtt gtaggtgctg tggggagcat    48240
cgagggagaa cacctgggcg aggagggac agaagcacca gggttgccgc tgcaggtgca    48300
cacctgcccc gcttcccgct gccgccacct gcacctcctg ggagccgtcc ctggtccctg   48360
aagcctgctt tgccgaattg gaggcaggcc caggtcaacc ctaaacccat gcctgcagga   48420
gtcagtggat aaataccca gcccgtgtcc cttaagctgg ctggacaacc ccgcggtgcg    48480
ctctacgctg ccccctgcaa gggcctagtg ggatagaact caaggcaaga gctccttgga   48540
ctctgtgggt acctcccctt tttaaaattt tactttatgt atgttttga cacaggatct    48600 cgctctgtcg cccaggctgg agggcagcag tgcaatcata gctcactgca gcctcgacct   48660
cccgggctca agcgactctc ccaccccagc cccatgagta gctaggacta caggtgcacg   48720
ccaccacgcc aagctaattt cttttctttt cttttttaa gagacggggt cttgctctgt   48780
acccaggctg gtctcaaact cctggcccca agtgatcctc ctgccctggc ctcccacagc   48840
gctgggatta caggtatgag ccactgcgcc cagcctcagt gtctgtttct gagggaacag   48900
gggacatttg gtcacaaacc cccacccccct gcccaggatg agcccgggcc gtacctgggc   48960
ctcgtagggg aggaaggcaa ggtgaatctc cttcaacgtc ttcaccacct ttgccagacg   49020
agagcggcct agctcactga acaggggctc ggggcaggct ggggtgaggc aggagtgggg   49080
catcaggcca gagcagcccc cacacctcct tgccccaccc accaacaccc taggctctcc   49140
tcactcactg tcggtgaaga agatatgggc cgctttgtag gtgaaagtcg gggtcccctg   49200
gaagtctttg atcagggcct gaaccgactg gggaaggtgg atcactctct gggcctgagc   49260
ctgcacacct aggctcattg gctgcctagg cctcccagcc accccccatc tgccaccatg   49320
tgcaaacatg gacggacggg gacatgtata tgtgcaaatg cacactagtg tcgcacccac   49380
atgggcacac gcgcacacac acagatgcac gcacgcacac acacatacac acgcatgcac   49440
```

```
acatgcacac acacacagat gcacacacac atacacacat gcacacacag agatgcacac    49500
acatacatac acacatgcac acacacagat gcgcgcgcac acatacatac acacatatac    49560
acacatgcag acactgatgc gcacacacac gcatacacac atgcacagac gcatacacac    49620
acgcatacac acgcacacac agatgcacac acatacatag acacatgcac acagatgcac    49680
atacatatac acgcatacac acatgcacac acagatacac acagacgcac acacagacgc    49740
agacacatac atacacacgc atacacacat gcacacagac agacgcacac acacacatac    49800
agatgcacac agatgcacac acacatacat acacacgcat acacacatgc acagacacaa    49860
atgcacacac agacccacag acacacacgc atacacacat acacacaaat gcacacacag    49920
acgcacacac atgcacatgc acacagacac atacatagac acacatgcaa acacgcacac    49980
acatgcatac acagatgcac acacacatgc acacacatgc acacacatac acatggacac    50040
atgcacacgt atacacatgc acacatgcaa tcacatgcat gcagacatac acacacatgc    50100
acatgtacac gcatgcacgc gcatacacac acgctcactc atgtaggcac cttctccgtg    50160
gggctcagca aataaatggc ctccagactg ggaatgggtt cccgccgttt gttgatgtct    50220
tcaacaacta gtaggaacag aggaagggac acaggtgggt ggcatccagg cagggccacg    50280
tggggagtct caggtgtggg gggttggagg cttggggagg aggggtggat gcttaggagg    50340
gactgcagga gaaacccact tagggaccac cagctaagag ccacacgaca gggttctgca    50400
ggggttgtgc agccaactgg gttccccaaa tttacagaca gggagactga ggttctgaga    50460
ggacaggctc cctcagcacc tatccctcaa tggcaaagtg actgggacac cacctggggt    50520
cacccataga aggctctgca ttcttgggac cccacatcca gagtccaccc tgggagtccc    50580
acacagggct ccacgaggga gctgcacggt caggaagggg ctgcagccag ggagtgctgc    50640
aggggaggcc tgcaatccat gggctcccgc agtcagcttg caaggtttaa gaatggattt    50700
ggtcacatga tccgggctgt ccgtgcaggg agctgcgtac ttgggagttc tggacgattt    50760
gaggggatcc tacactcaag ggctgaaccc tgggagaggg gcacagtcag gggttcccac    50820
gctcaggtcc catctcactg ggacgcgtt cactcactgg tgatgccctc agccaggata    50880
tctgacattt gcagcagga agacaagatg cgcatgcttg ggtgatccat gataagcacc    50940
tgtccagatg gatggacaga tggatggagg agcaggcgga agaggccaca gctggcccca    51000
gaaggggcca aggcagtggg aggggcagtt tcaaggggctg gctgggtggg aggacccaga    51060
acccattcac ccaactccac ccatgtggac aggcagttct tgggggtccc acattcaggg    51120
tcttccccat aggcctgatg atgagctgcc tctgggtacc cagccatctg cctcacccct    51180
accttccact ccccatcctt cttgacactc cgaataactc cgctcagaat ttctgcaggg    51240
aagggagggg aggggtcaga atgctggttc tctggtccca ccactgcccc aagccttctc    51300
agccttgggg ctgaaccccc atcttaattc ccatttactt tttttttttt tttaagagag    51360
gaggatctca ctctgtcacc taggctaaag tgcagtggtg tgatcataac tcactgcggc    51420
ctccaactcc tgggctccag cgatcctctt gcctcagcct cccgagtagc tgggactaca    51480
ggtgcatgta ccacccacag ctaatttatt tttatttctg tatagatggg gtctcgctat    51540
gttgcccaag ctggtctcaa acttttggcc tcaagcagtc ctcctgcctc ggcctcccaa    51600
agtgctggga ttacaggtgt gagacacggc acaggaatca tttattttta gccccagtt    51660 ctgcaaattg gcttctgggg tcaccccaa tttacagaca gggaaacaga ttcttaggca    51720
acatgtaact cacctacgca tcctgagtgt ctaagtggca gagtgctggg gcaaaaggtg    51780
ccactcgata aacatgtttt aggtgaatga aaagaggaga accgggatca tctacagctc    51840
```

```
tatctgcctc tagcgccagg ctctcggctt ccccacctgc tacctcaagt attcctgctg   51900
tgagggtttc agccagtccc cccaacctgg tctaaaatgt aggacccctg gttcccagct   51960
ctgaggcatg cctagctgag gctatcccac tgacctccgg tctcagtttc ctcatctgta   52020
aaatggaatc acttttttct aatctccccc aattaaaggg gtttgagcta cagaccgccc   52080
tgcctagagg agagagtgga gagaagtaac ggggtggccc cgcccagcca cgtccactgt   52140
gtcatgtcca ctgttatcaa gacgccagg gcggaaggag cagctgaggc cggaactccc   52200
cggggtggag gaagaggcgc cctccaccct tcccccaaga accggggccg gtgaggcctg   52260
gacgcctgcg tcctccagct gcaaggcgct cctggaaatg gggcaaggag gaagacatcc   52320
cctacaccac ccctgtgggg cctggacacg tcccctgagc gctcacagca cctagggtcg   52380
ctgaccagag ccctaggagg ccccaagaat ccagcccctg aactttgccc ggcttaagag   52440
atcctagagt gtgggcatcc agctgtgccc tcctcccccg gcaggcaccc taggaggccc   52500
aggagtccgg gccccagcct ccgccacact ctacccgtcc cctttgggtc cccggagtcc   52560
ggccccccaa ttttgttctg ttctggcacc ggagagcagg ggcgtccagc tgggaacccg   52620
tccccgcccg ccccctcgag ggtcaggtgc tcggacgccc agcccggccc ccaactccca   52680
gccgccatga aacccaggat cccagagccc gtgcgtcccc gacccccgtc ccacaccgga   52740
cgccagagcc cggccccgga gaggcactca ctttccсccca ccaccgcctt cagccccgag   52800
ggcgccatct tccccgaggg gcgccgccgc cgcttccggg tgtgtcccaa ggtgggggcg   52860
tggccgcgcg tcacccacgt ggaccсccgcc ccgcgccctg tccccgcccc ctgcgcacct   52920
ggcccctccc cgccgtcggt tctcgcccag gcccaggaag ttgagtccct ggcggggagg   52980 acggcaggt gcgtccgcgc tgccgagcac gaagtcgctg gaggtgcaca cctcgacgac   53040
acgctcacag atgggagttc agacacacac ttcctggctt gcgtgcgaag caggatcgca   53100
gggcaataat ccctccatct tccccggagg gttctgtgcc tgcaagatac acggcaccca   53160
ctcgatgcca ccgggccgcc actgtctggg cctgggatct tgacccactt gccttctgta   53220
cttcagggtt tagaggcagc agcagcagca gcagccgtct tggataactt ttgatggatt   53280
caggaggcct ggagacctct tgtgtgcagg cacctggaca taattttcat tcagtcctgc   53340
ccaatgttcc gacctggact gcggtgccga cgaggaaacc gaggcttagc gggatcccta   53400
atccaaggcc acgacgagtg agcctgctgg gttcaagcca ggagcctgtc cccaggggc   53460 atttgtcaca gccttaccct cttccgggag ggcgcaacgc ttaccctcgt ggaccaacaa   53520
tcgaattaac atgctgatac acacatgggg tgagtgacgc cctcaaatgc ttgcaaacac   53580
agacacacac tcggaatttc agaagctgct tctgctgtgt gtcctgtcgc ttggaaggca   53640
cagccccagc agcacccata caaaatgagg tctccgattt aaggtgcgag gtatgtgtgc   53700
aaacagactc ttgctggtct gagctggttc cttcgctcgg ccgtgttgat gaaggtacca   53760
agccccctgc cacttacatg ggacataggg agtgaatcag acccgaaggt ctggggaga   53820 taggaaagga tccatgctgc cctaaaggaa ataaactaat gtgacaacaa gtgccacaga   53880
aggtaggggt gggagggac tttactgagg atgacccccg agggcctctc tgaagaagca   53940
gccttttgac attatсссcta aatggattct agaagcagcc acacagcatg tccaggtaga   54000
gaagggagga gccccgagct taagaaggct ggagggtggg ggcagcaggg gccagacttc   54060
tgtaggacaa ggtcagactg acccatccca gtgccaggat gcaggacttt cagtgctaaa   54120
aataggacag tcacaggcaa accaggacgg ttggcaaccg taggtaggag tttgagctat   54180
ttcttccttt cctttccttt tcccttcctt tcttccttct tctccctcct ccccattttt   54240
```

```
gtttgttttt gttttgtaaa gagacgggtc tcgctctgtt gctcaggctg gagggcagtg   54300
gcacgatcat agctcactgc agcctcgact tcctgagctc aagggattct tccacttcgg   54360
ccacccaagt agctgggact acaggtgcac gccaccgtgc ccggttgatt ttgttgttgt   54420
tgttaagaga caggatctcc ctatgttgcc caggctggta tcaaactcct gggctcaagg   54480
gatcctcctg ccttggcctc ccaaagtgtt aggattttag gtatgagcca ccgcacgctg   54540 cccttcctc cttttgtaac agctttactg agatataatt cacataccat acaactcgct    54600
gacctaaggt gcgtaagtca atggctttca gtattttgg agttgtgtgt ccattaccac    54660
aatccatttt agaacatttc cacaacccct aggtgtttgg gttttgtctt ctcaagagtt   54720
ttgagcaggg gaaggcgggg aaccctccag atcctggggg gatggaagcc aggaccgcct   54780
ccagcttctc agcctgaccc cttgggggga cagagagctg ttagggccag ccacccacc    54840 actaaccccc aaaagatatg aagtactaat ccccaatacc ccacaatagg atcttatttg   54900
aaatggggtt agtatagata ttagcagtga gcatgaggtc acactggagt agagtaggcc   54960
cctaatgcaa tatcactggt gtccttgtaa gatagttata tgtctgcctg ttctgtgta   55020 ggtggttggg ggggtgggga aatgggtata tgaagactgg gacacagagg gagaatgcca   55080
tgtgaccacg gaggcaggga gtgaagagct gcagtgacaa gccaaggaca tcaaggacgg   55140
caggccactg ccaaaagcca gggaggggca aggagggctc ctgagacctg gttttcagag   55200
ggagcacagc tctgccaaca ccttcatttc aggctgtggc ctctggaacg ttggctcaat   55260
aaatttgtta aaaaaaaatt ttaaaggctc agcatggtgg ctcatgcctg taatcccagc   55320
actttgggag gcccaggcag gaggatcaca tgaacccagg agtttgagac tagcctgggc   55380
aaaatagtga gacctcatct ctatataaaa atatataaca aaagtcaact tatgtgtttt   55440
aagccatctg gtctatgaca ctttgttctg gcaggcctag gaaagggata cacgtactga   55500 ggaggggac acttcattgg catagaggga gagagtgtga acttggcctt ttgtggaaca    55560
gaggaggctc gggcagaggt ggtgatagtg cagcccattc attctgagat gaaacttcca   55620
ctggtttccg taaaggcgtc ttggggaggg aagggaaggg gatggggacc tcccagtggt   55680 atccctgct tgggcactga gggaaagcca cagtggctcg ggggaaaagg cagggacgtc    55740
ctctccccgc ctgcctctgt ccccaggag tctcgcctcc tgttcccacc tggggctagg    55800
gtgatagagg agaggagata gctcaacctg gcatttaggt ggtgtgggaa caggagaccc   55860
cagactttct tgttttgggg tctggggcag gcaaccaggc tccagggaca gtgagttgaa   55920
ggaagggtgg ctgggagacc ccttgacttg ctgccaagga gacagagctg gagctagggt   55980
ggccggtggt gtctgaggca ggtgcagaga gggagggagg gaaggggcct ttgactccaa   56040
cctccttttt ctgtaccgac tgcaggtggc agctgccctt tcaggagcca gtgggggaac   56100
ctgggtggct gggtgggac acctgcaagt cctccctaag ccagctacca ccctacactg    56160
ttggcctccc ttctccaact gtgggatgc tgctcaggcc ttttgtgaca tcacacctga    56220
gagtccctgg ggtccagtca ttgctgctgg gcacagcgag gtccaagctc aggtcgccct   56280
gccccctacc caccatgcca gatccagcat cgttgtgggc aaacaattat ctggatgatc   56340
tttatggggc ttaagcttgg gtgggagcag atggggcatg agctggggat ttggggatgg   56400
ggggaatcca caccccacg tcctggacgt ttaaaaggcc ctctctggca ctgggccggg    56460
gcagaggcca gcagaaaagt gactggagtc cagggacatg atggatcagg aggagaagac   56520
ggaggaaggc tcaggcccct gtgccgaggt gagagggccc tgcccccacc ccaccccag    56580 ctcaaggtct cagagcccat gattgacaag actagtttgt agggcaccta attaacgagt   56640
```

```
gagtctccta ggacccoctg acccagttgt ggctgtagaa aggggctggt gggcttgggg   56700
gtctgagtgc caggccccag ggcagagggc agggctctcc gtgtggaccc ctattgatgg   56760
gagatgctgg gacctggggg tagctcctgg gccatgtttc cctgattcgt gtcccagctc   56820
ccaggccaca ctcatcaggc cccaatctag gacggcggga cacgcatcgg agcctgtccc   56880
ttgaagcggt accacgtgaa gtggcactgc tggccagggc ccctggggcg ggggccggga   56940
ttgggaagga gactcatgtc tcattcagaa cagctctgca gagaggatcg gcggggacca   57000
tggtgagagc tgaggaagtg gggacggcag gccccggggt cagggtgtga gcaagctggc   57060
taggaagttt ggggagggc ccccaagctg aagggccaac cagactgagc gagtctgtcc   57120
ccaggcgggc tccccagacc aggagggctt cttcaatctg ctgagccacg tgcagggcga   57180
ccggatggag ggacagcgct gttcactgca agccgggccg ggccagacca ccaagagccg   57240
tgagcatggg cacggggtg ctgtccatgg ggcgtgaacg gggtgggagt gcagggcaag   57300
tggtcatctg gagggcctgg gggcacggga tgtgggaggg ggttgtgcac cctgaagcat   57360
ctgtgtgggg gtgaaggggt agggttgggg gccccactc cggctgtgtc ctcccaagtc   57420
tgtgaacgtc cacgcagaga gcgacccac cccgagatg gacagcctca tggacatgct   57480
ggccagtacc cagggccgcc gcatggatga ccaacgtgtg acagtcagca cgctgcccgc   57540
ttccagcccg tggggtccaa ggtaggtgat gttctggcga tgtcgaggag aaacccgcca   57600
ggcagtgctc tccgatcctg ccctccaccc cagccaggag ggaacagggc ctgccccatc   57660
tctgtccatc cgctgccctg acttcagatg ggaggaccaa ggcccaggca gtggctagag   57720
gggcccaagg ttatacaggg gccatgctag tgtaagaccc atggctggaa cttgtggctc   57780
ctgcccccaa gtctgaaggt tctggggagg ccaaagggag aaaataggac cccttcctag   57840
gaaagtatcc caggaggaa gtcacgtaag ctcacacata ggatatatac atctgtatac   57900
tcacatctgt tgacttcaca catacacgaa gcttgggttc tgatcaagat cccagcgagg   57960
gccccaagac ctgccacctc acactcaaat gccaccctaa atggcagata ttgagggtaa   58020
acatagacca gtgctcacaa tgaggtggga cacggtggct acctgcaccc tctctccatt   58080
gttcgccacc tgtggccggc actgcccttg agccctcccc ctggctgacc cctcttcatc   58140
cacaggacgg agcacagaaa cgagctggga ccctcagtcc ccaacccctg ctcacccctc   58200
aggacccgac cgctctcggc ttccgtcgga acagcagccc ccagccccg acacaagccc   58260 cctgagggcc tgaggcatcc tgggtctcac tcggccccca aaaactgata aaagaataaa   58320
acacttaaat gaataacaag gaactgagta tatgtatatt tcatcagggg agggctagg   58380 actcccactt ggaggcctca ggagttctgc tgggcgtcgc gaaggagctt ctcctcccgc   58440
cgcttccgta acctctcttt gaattcctct atctcttgaa gctaggggtg gagaagcggg   58500
tgggacagga aggggggagg ggcacacacc tcagagccgg gaccccccc cccgcccac   58560 ctctcccacc accctgcccc agaccacggc ttcagggttc agtgtcttca ctggaagccc   58620
cctgccaatt acaaagggt ccgcgtggga tccgcttcac tcttccagga gaaggcaata   58680
aggaaaccat ctactcctct gctctcggtt ccttactcat ggctgagagt aaaatgtttc   58740
tttttgagac aaagtctcac tctattgccc aggctggagt gcagtggcgt gatcttggc   58800 tcactgcaac ctccacctcc tgggttcaag tgattcttct ccctcagcct cccaagcagc   58860
tggaattata ggcgcctgcc accatgcctg gctaagtttt gtatttctgt agacatgggg   58920
tttcgccatg ttggccaggc tggttttgaa ctcctgacct caagtgatct acccacctca   58980
gcctcccatg ccctgggatt acaagcatga gccactgcgc ctggcctaaa attttcatct   59040
```

```
aaaacccatc ccggatacaa gaatccagcc tcctccatcc ctctggcagg aagaagagat   59100
cacttacctt ctcaggtggc cacagctccc tctgtaagga aaagtcacaa atgggacacg   59160
agccaaaggc ctccagagcc ccacatcagg gcagggtcgg cttatgggag gcagacatta   59220
gtccccagca gactgctgcc ccacaccctc tcccacccct ggaatgaacc ctcaaacact   59280
cctcttatgc ccaccttgcg ctgtatgaca tcgtcctcaa accactcggc ctgattggaa   59340
acccagaaca tagccacagg gaaagtgagg tagattatca tctggaatgg cagagggtgg   59400
gtgaggtgag ctccccccaa gcaatgtgca gaggctcctc agagcctggg ggacccatcc   59460
tactgcagag tccagaagcg cctcgttacg gccgacccaa gaatcccaga actcccacca   59520
agggtacaga aacctcgcac cctaaaacct aactcctata atccaggagg cctcattcct   59580
gaaagttccc tctgagctgg agtcttcctc tcaaacacag acagacacac agacgcccca   59640
gctacaatca aaagcatctc ctcgagacct cattacccat ccccacttaa gatcccggga   59700 gcaccccccaa acccaggagg cgtcactctt caactccact tctcgaagtc taggaatctc   59760
cctgtcatag acacccaccc accacgagcc cgagagctcc ccagggatct taagtcttcc   59820
ttctttagag ccccccttctc agctcacccc tctctgaggt ccttcctcgg accagccctc   59880
tcacagcccc caaaatcaga agcacaaatc cgagaacccc cccagcccag cgtcccctct   59940
cctggatttc caaccagaaa ggtcctctca aatcttaaga gctttctcct tggagctccc   60000
tcttcctttg aagtcccccc atttccaacc tcatcttcag atccaggaag atcccctgcc   60060
cagcctccca acccactcct gtgtccactg acccgaaata tctccagctt caccccccatc   60120 tcgtttctcc cggtcaacaa agccagttcc gcccaaagcc gaccctccag caagacagaa   60180
gctcactggt gttttgcacg ctccattgct gaagctgatt ggccaatgtg tatcctcatg   60240
gcgcatcttc tggcgcctct attctgcttc cggtcgctgg cgtcgtcgaa aagaagtcaa   60300
taacgtgggc ctgtccgtca aaaatgattt aaccaataga aaacgggtct ggctcggagg   60360
ggcgggccgt cagtggtaga cgtcataagc gcgcgactct ctcctgtacc tgggcatcca   60420
gaaaaatggt ggtgatggcg cgactctcgc ggcccgagcg gccggacctt gtcttcgtga   60480
gtccacagag gagccggggg tggcctgcgt tggggcattg gacctggac gccgcagggg   60540 atcgaggctg ggtcggcaag gagatttagg ccgaaactgc caggccaagg tctgggaacc   60600
ctaatgggcc agagaccgga tcgtcatgtc cgcaccgaac tgtccaggag taaaaatatg   60660
gtgttgtatc ttcgggtctg agtagaaaac cactgtcgaa gggaagcgtc tagcctcccg   60720
aaccaggggc ggaaatgggg gcgtgcaggg aatgggagag gaggaagatc gcataactga   60780
accttgagag gtgaagatcg gtgtctgaag taaaggcttg cttacgaggc cagggttctg   60840
gtttctggga tgaaggcttg gttttctgga tagcggtctc taggcctgga ctgcagcatg   60900
acagtttctg gggtggtggc caggctagaa gaaccctggt gatgtggagc ttgtcaggcg   60960
atggccagta aaatacttac tctctggagt agaggcgtga catcttcacc agattcttgg   61020
tgtgcagagt taaaggcttg gcttctggtg tataactcct cctgtgagat aaaggcctag   61080
cttttaattt ctggggcaga gttgagctag acgctggcta gtgggatcct ggggcgggg   61140 ctagtggctt ggaatctgga cctgagagcc ctggtggctg gggtaaagat ctggtcatct   61200
gggcctgggg tggagatggg tcagatggtg acagtgggag tctgagggc aaaggcctgg   61260 tgtctgggaa gaggcacgtt ttgaagaagt ggggtctggt gtccaggact ggcatctggg   61320
ccagggcctt ggtatctaag gagtctgacc atctggggca gaaagcgagt ggtgatgcgg   61380
actcattcct ggcccagagc cctaatgact gagaagtctg atgatttggg ttcgattttg   61440
```

```
ggtagttgaa ttctgagggg taaaggtctg ggccactgtc ttggtgtcgg gcatctggtt      61500
tggtgcctgg gcatctggtg acctgacttc cttggtgggt ggtgggatct aggtaaaagt      61560
ccggagtttg gacctgagcc ccagcagtgg gatggtgctg cacacaggct ctgagggtag      61620
gcctctcttc ttcccattcc ctggcccctgg caggaggaag aggacctccc ctatgaggag      61680
gaaatcatgc ggaaccaatt ctctgtcaaa tgctggcttc gctacatcga gttcaaacag      61740
ggcgccccga agcccaggct caatcagcta tacgagcggg cactcaagct gctgccctgc      61800
aggtgggaat ggctccagct gccctgccca ccagccccca ccccacctgg tccagttata      61860
acaaaactgc caagtgggtc ccgggtcccg ggtgattgct tcgtgtttca tcactgacct      61920
gtacatccct tgatgggtca gcacaccttc tctgatgtcc cagtctgtcc ctgtcattgc      61980
tgagacatgt caccccctccc acaccccttc ttcccacatt tgccaactgg ggcagggcaa      62040
atggttctgg gggtgtccat aaagctgacc gatcagcatc tgtcccctcc tattcccag       62100 ctacaaactc tggtaccgat acctgaaggc gcgtcgggca caggtgaagc atcgctgtgt      62160
gaccgaccct gcctatgaag atgtcaacaa ctgtcatgag agggcctttg tgttcatgca      62220
caaggtttgg ggctcggcga ggggatgaat cgggaagtgg agctcagtcc atggtggtgg      62280 gtgggcggg gacaggggct gggctcagca tgttagggat gggggcttgg attcctgttg       62340
cttctttgca tgggaagttg ggctggactc agtcctggag ctgggggttt ctgggtcccg      62400
ccgcatttat gtggtggccc caggtgtggc tcagccacag gacatcgagt gtctgtggcc      62460
aggccatgga gtccgtggct tagccccagc cgcctctccc cacaccccca gatgcctcgt      62520
ctgtggctag attactgcca gttcctcatg gaccagggc gcgtcacaca cacccgccgc       62580
accttcgacc gtgccctccg ggcactgccc atcacgcagc actctcgaat ttggcccctg      62640
tatctgcgct tcctgcgctc acaccccactg cctgagacag ctgtgcgagg ctatcggcgc     62700
ttcctcaagg tgagcctagc aggtgcgctg gttccccagg ttagtttcca gaaacggcct      62760
cactgtgaca ctagctccgt gtaggatgtc acccagcaga cgggatgtgg gaagaggctc      62820
ctggagatgc atgtgttttg ttgttgtccg tgattcatgt cttttatttttc caaatagttt    62880 gttcacactg gtttcacatt aggcatagcg atgggtgctg aggacagtgt gactaagaca      62940
ctccctgcct gcacggagct tttagtctaa ctaggaagac agatgcatat gagctgatgg      63000
catgaactag agtaaaacca cagccatgaa gagggccagg aataagggtg gggagaagca      63060
ggcagggtgg agagtggaag caccagccgg gcgggagtgg ggcatggttt gctcaaactt      63120
aaagtatctg ttttatgacg tttggattct aagctggacc agtcaggact gaggctggac      63180
ccgtggggcc caggctggac actatagtca aggctggacc catgggatca aggctgaccc      63240
aaaggggcca aggctagacc agtcaggact gaggctggac tagtgagcc aaggctggac       63300 ccattgtggg ttgggggtca attctaaccc aaaaggacca aggctggacc attggggctg      63360
agactggacc accgcagtca aggctgtgcc cttgcgggtc aaggctaacc caaaaagtcc      63420
acagctggtc tagtcaggac tgaggctgga ccagtggagc caaggcagga cccacagggg      63480
gttgagccta acccagtggg gccaaggcta gaccagtagg aaccgggctg gaccagtggg      63540
gctgaggctg gttttgacagg gcttgctttt gcccaagaca ctcataaatg ggtgggggggg     63600 gacgccccga agccactgaa tcgggaggtg gcgtagcccc tgccacccca ctgactgcct      63660
gaggggtggc tcggtcccca gctgagtcct gagagtgcag aggagtacat tgagtacctc      63720
aagtcaagtg accggctgga tgaggccgcc cagcgcctgg ccaccgtggt gaacgacgag      63780
cgtttcgtgt ctaaggccgg caagtccaac taccaggtgg gcctgccggg agccggcaac      63840
```

```
tgggtgggag ggccacccec tccatgactg agcctgagac tctcccccac tgcccatgc    63900 cctgcagctg tggcacgagc tgtgcgacct catctcccag aatccggaca aggtacagtc   63960
cctcaatgtg gacgccatca tccgcggggg cctcacccgc ttcaccgacc agctgggcaa   64020
gctctggtgt tctctcgccg actactacat ccgcagcggc catttcgaga aggtgcatgc   64080
tggcacacgg ggctctgggt tcggggcggg gtctccctcc gacactcggg gacacatgtt   64140
gacacatgca cagacagaaa acatgccatt tatggctggg tgtggtggct cacacctgtc   64200
atcccagcac tttgggaggc cgaggcggta ggatcacttg aggtcagcag ttcaagacca   64260
gcctggccaa catggtgaaa ccccatcact actaaaaata caaaaattag tcagacatgg   64320
tggtgcgcgc ctgtaatccc agctactcgg gaggctgagg caggagaatc gcttgaactt   64380
gggaggtgga ggttgccgtg agctgcgatc gcgccacgga agtccagcct gggtggcaga   64440
gcgagactcc atctcaaaaa aaaaaaaaaa aaaaaaaagt gccattttg acagacatgc    64500 atatccctgc acacgattac tatcctgctg agggtgggg agcactcctg cccgcaagca    64560
cgtcagcctt tggagttcag ccacattttg cgttcagggt ttcaccctct tggctctgcg   64620
gcctttgccc caactaaggg tggtttgttc tttcatttgt aaaaatcagg gtgacagttt   64680
actgccttgt caccaatcag                                              64700
```